(12) United States Patent
Chen et al.

(10) Patent No.: US 10,092,201 B2
(45) Date of Patent: Oct. 9, 2018

(54) ACCURATE ECG I-POINT AND J-POINT DETECTION AND MEASUREMENT

(71) Applicants: Guangren Chen, Acadia, CA (US); Rong Yang, Porter Ranch, CA (US); Zhongnong Jiang, Richardson, TX (US)

(72) Inventors: Guangren Chen, Acadia, CA (US); Rong Yang, Porter Ranch, CA (US); Zhongnong Jiang, Richardson, TX (US)

( * ) Notice: Subject to any disclaimer, the term of this patent is extended or adjusted under 35 U.S.C. 154(b) by 0 days.

(21) Appl. No.: 15/961,952

(22) Filed: Apr. 25, 2018

(65) Prior Publication Data

US 2018/0235497 A1 Aug. 23, 2018

Related U.S. Application Data

(63) Continuation-in-part of application No. 15/904,543, filed on Feb. 26, 2018, and a continuation-in-part of application No. 15/393,135, filed on Dec. 28, 2016, now Pat. No. 9,999,364, and a continuation-in-part of application No. 14/749,697, filed on Jun. 25, 2015, now Pat. No. 9,538,930, which is a continuation-in-part of application No. 14/662,996, filed on Mar. 19, 2015, now Pat. No. 9,339,204, which is a continuation of application No. PCT/US2015/020828, filed on Mar. 16, 2015.

(60) Provisional application No. 62/489,540, filed on Apr. 25, 2017, provisional application No. 62/463,662, filed on Feb. 26, 2017, provisional application No. 62/271,704, filed on Dec. 28, 2015, provisional
(Continued)

(51) Int. Cl.
*A61B 5/04* (2006.01)
*A61B 5/0402* (2006.01)
*A61B 5/0245* (2006.01)
*A61B 5/00* (2006.01)
*A61B 5/044* (2006.01)

(52) U.S. Cl.
CPC ........ *A61B 5/04023* (2013.01); *A61B 5/0245* (2013.01); *A61B 5/044* (2013.01); *A61B 5/04014* (2013.01); *A61B 5/6823* (2013.01)

(58) Field of Classification Search
CPC .............. A61B 5/04023; A61B 5/0245; A61B 5/04014; A61B 5/044; A61B 5/6823
See application file for complete search history.

(56) References Cited

U.S. PATENT DOCUMENTS

2005/0115561 A1* 6/2005 Stahmann ............ A61B 5/0031
128/200.24

* cited by examiner

*Primary Examiner* — George Manuel
(74) *Attorney, Agent, or Firm* — John R. Kasha; Kelly L. Kasha; Kasha Law LLC

(57) ABSTRACT

An ECG system measures and annotates the I-point of in an ECG waveform from harmonic waveforms. Electrical impulses are received from a beating heart. The electrical impulses are converted to an ECG waveform. The ECG waveform is converted to a frequency domain waveform, which, in turn, is separated into two or more different frequency domain waveforms, which, in turn, are converted into a plurality of time domain cardiac electrophysiological subwaveforms and discontinuity points between these subwaveforms. The plurality of subwaveforms and discontinuity points are compared to a database of subwaveforms and discontinuity points for normal and abnormal patients. A discontinuity point is identified as the I-point of the ECG waveform from the comparison. The ECG waveform is displayed along with a marker at a location of the discontinuity point.

20 Claims, 58 Drawing Sheets

Related U.S. Application Data application No. 62/271,699, filed on Dec. 28, 2015, provisional application No. 62/017,185, filed on Jun. 25, 2014, provisional application No. 62/008,435, filed on Jun. 5, 2014.

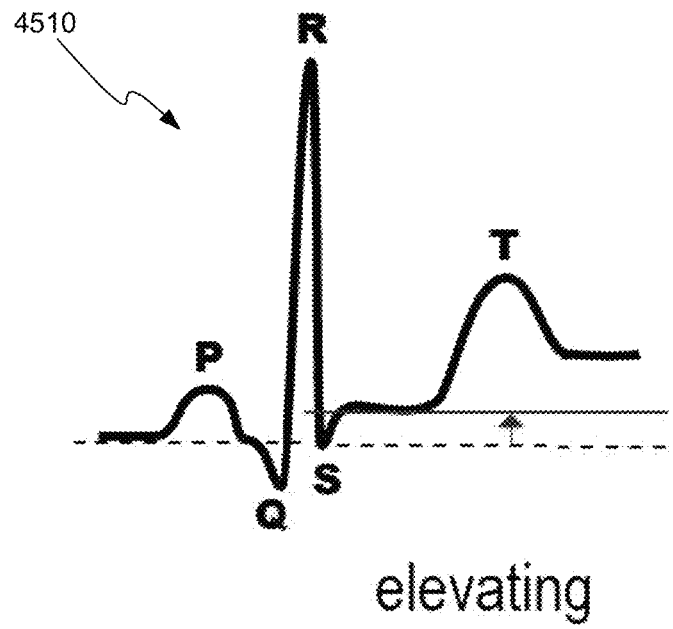
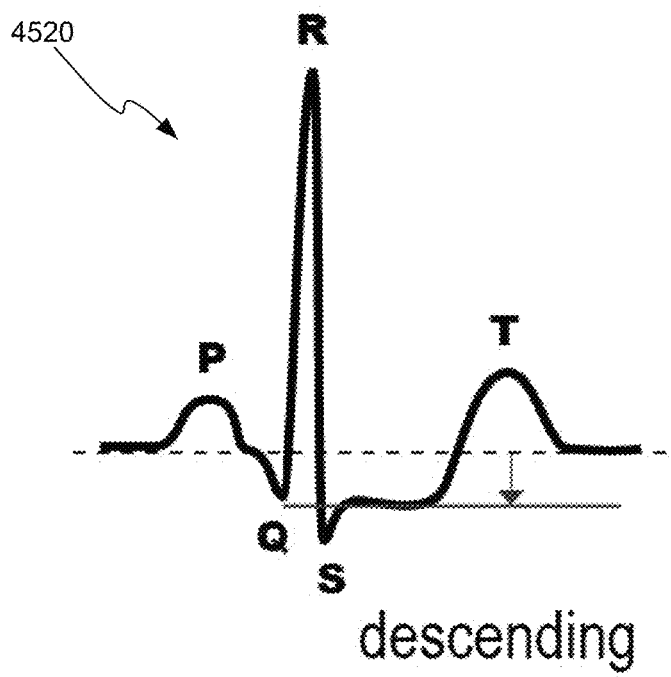
FIG. 45

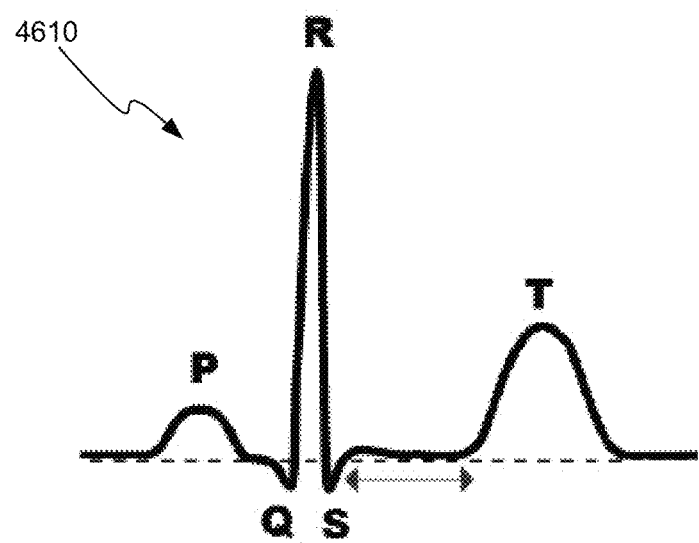
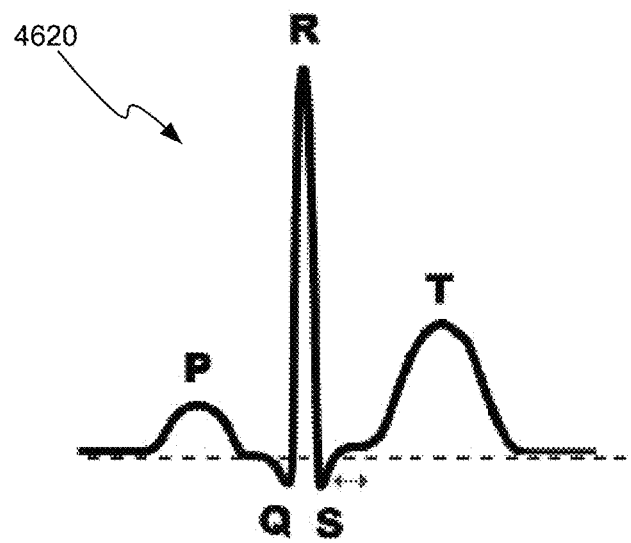
FIG. 46

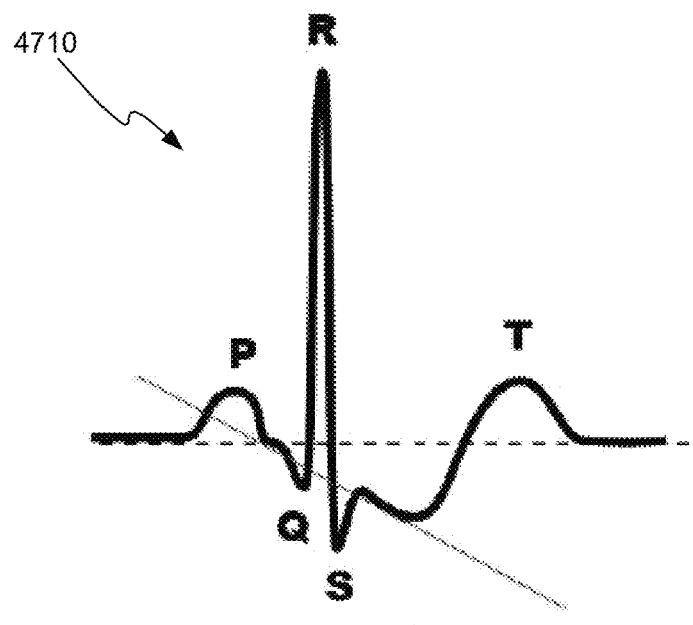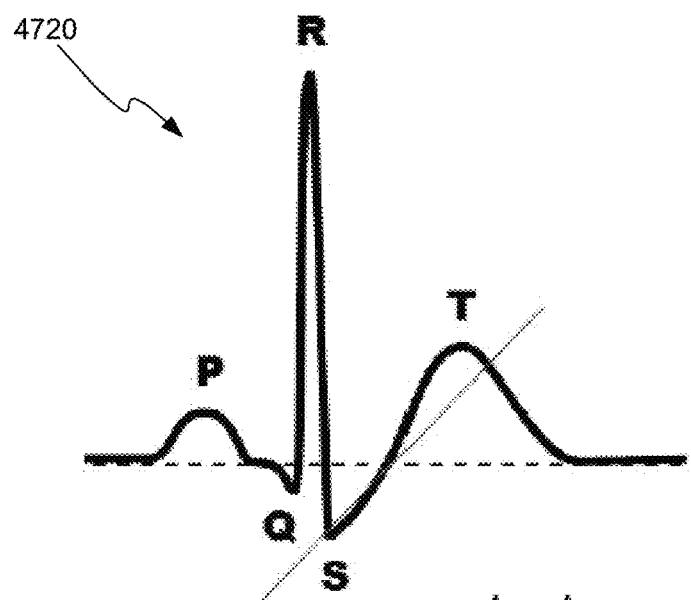
FIG. 47

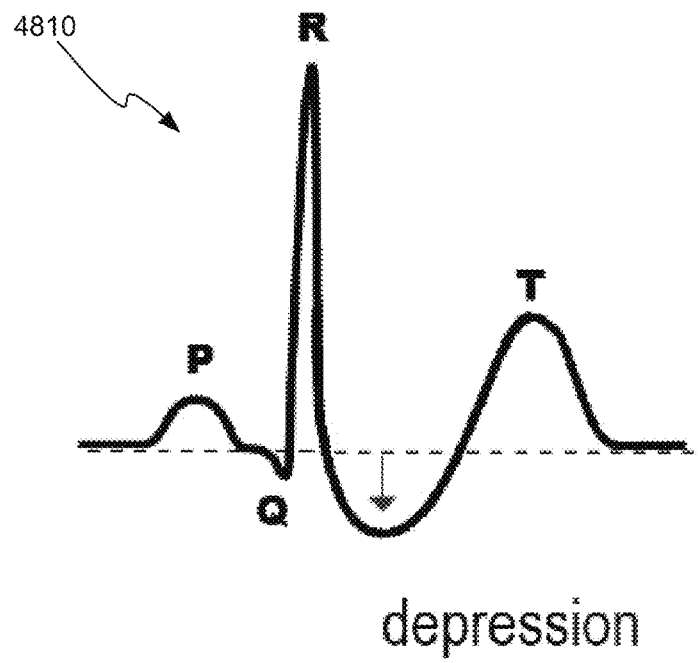
depression
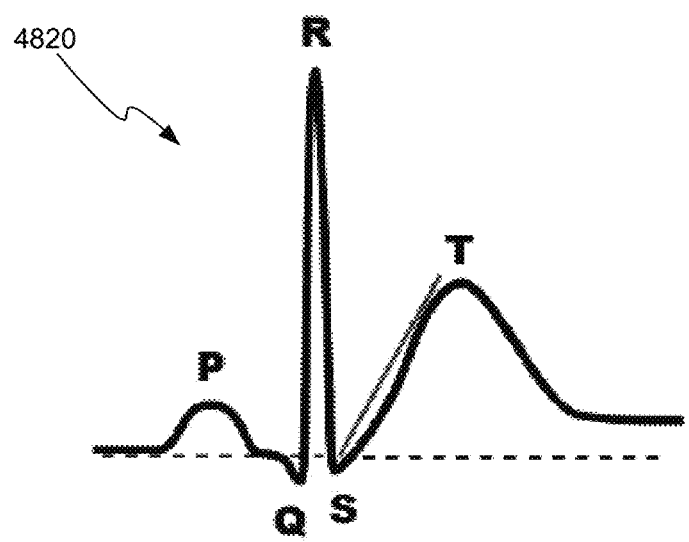
ST Vanished
FIG. 48

ACCURATE ECG I-POINT AND J-POINT DETECTION AND MEASUREMENT

CROSS-REFERENCE TO RELATED APPLICATION

This application is a continuation in part of U.S. patent application Ser. No. 15/904,543, filed Feb. 26, 2018, which is a continuation in part of U.S. patent application Ser. No. 15/393,135, filed Dec. 28, 2016, which is a continuation in part of U.S. patent application Ser. No. 14/749,697, filed Jun. 25, 2015, now U.S. Pat. No. 9,538,930 (hereinafter the "'930 Patent"), which is a continuation in part of U.S. patent application Ser. No. 14/662,996, filed Mar. 19, 2015, now U.S. Pat. No. 9,339,204 (hereinafter the "'204 Patent"), which is a continuation of PCT Application No. PCT/US15/20828, filed Mar. 16, 2015, which claims the benefit of U.S. Provisional Patent Application Ser. No. 62/008,435, filed Jun. 5, 2014; this application also claims the benefit of U.S. Provisional Patent Application Ser. No. 62/489,540, filed Apr. 25, 2017; U.S. patent application Ser. No. 15/904,543 claims the benefit of U.S. Provisional Patent Application Ser. No. 62/463,662, filed Feb. 26, 2017; U.S. patent application Ser. No. 15/393,135 claims the benefit of U.S. Provisional Patent Application Ser. No. 62/271,704, filed Dec. 28, 2015, and U.S. Provisional Patent Application Ser. No. 62/271,699, filed Dec. 28, 2015; and U.S. patent application Ser. No. 14/749,697 claims the benefit of U.S. Provisional Patent Application Ser. No. 62/017,185, filed Jun. 25, 2014, the content of all of which is incorporated by reference herein in their entireties.

INTRODUCTION

The teachings herein relate to an automated electrocardiography (ECG) analysis system. More particularly, the teachings herein relate to systems and methods for measuring and annotating the I-point of an ECG waveform during measurement of the ECG waveform. The J-point of an ECG waveform is also measured and annotated. These systems and methods use the harmonic signals of a conventional ECG waveform and previously recorded data from normal and abnormal patients to measure and annotate the I-point and the J-point of the ECG waveform.

The systems and methods herein can be performed in conjunction with a processor, controller, or computer system, such as the computer system of FIG. 1.

BACKGROUND

ECG Accuracy Problem

Since the first ECG instrument was invented in 1903, its accuracy rate for diagnosis has always been a problem in clinical applications. For people with abnormal conditions, ECG waveform variations are not the same for the same person and are not completely identical even for the same disease. They are at most self-similar. Self-similarly, for example, refers to an object having a shape that is similar to the shape of one of its parts. As a result, ECG science is one of the most complicated disciplines in medicine.

It can be seen from numerous signal processing methods that, during a lifetime, each beat of a person's heart has different specific signal variation, and the difference is significant. However, generally one is unable to observe this from a conventional linear ECG waveform with the naked eye.

Since computers started to be widely used in ECG analysis the 1970s, people have been consistently exploring, searching, and studying how to automate ECG analysis and diagnosis. In the past half a century, thousands of scholars have made efforts in studying algorithms, exploring pattern recognition, and applying those in ECG mapping and automatic diagnosis.

However, wide clinical use of such systems has yet to be achieved. There are at least three technical reasons for this.

1. The ECG waveform is morphological, and generally no consistent mapping points can be found. In other words, the information in the ECG waveform is conveyed through its structure or form. Also, the waveform is abstractly self-similar. In particular, there is no rule for abnormal variations, the time axis signals interfere with each other on left and right sides of as well as above the x-axis, non-linear variations are invisible, and the same disease may have hundreds of millions of variations, but they are not clearly displayed on the ECG waveform. As a result, all ECG parameters are, in general, not accurate, and it is almost impossible to measure these parameters after the waveform changes. Therefore, the highest accuracy of automatic diagnosis by existing ECG software reaches around 38%. Also, this accuracy is only achieved for simple ECG waveform variations and not for many complex waveforms. This is because no mapping point can be found due to the loss or disappearance or deformation of the P-QRS-T waveform.

2. The second reason systems for automated ECG analysis and diagnosis have not been adopted clinically is related to how a conventional ECG waveform has been measured. As described in the '204 Patent and below, the conventional ECG waveform is a single time domain waveform that represents a combination of many different frequency domain signals from different parts of the heart muscle. As a result, information specific to these different parts of the heart muscle are generally lost. In addition, the conventional ECG waveform is a linear waveform, while the heart is a nonlinear system, and the vast majority of variations as a result of abnormality are nonlinear.

3. The third reason systems for automated ECG analysis and diagnosis have not been adopted clinically is related to the high number of false positives found in normal and abnormal populations. For example, in many cases, conventional ECG waveforms show abnormal results in tests of normal people and also show normal results in tests of abnormal people, which makes it extremely difficult for clinical reading and understanding and makes it impossible to determine whether a result is normal or abnormal.

However, the heart is an electrified organ, and there is no doubt that the electrophysiological responses of a heart organ are the fastest and most sensitive measurements to diagnose heart problems. ECG remains one of the most extensively used clinical tools used at present along with blood tests and imaging, despite the lack of accurate systems for automated ECG analysis and diagnosis. As a result, there is a significant need for such systems.

Recent advancements have addressed one of the three technical problems. This is the conventional ECG waveform measurement problem. As described in the '204 Patent and below, an ECG device has been developed that uses signal processing to detect one or more subwaveforms within the P, Q, R, S, T, U, and J waveforms of a conventional ECG waveform and/or within the intervals between the P, Q, R, S, T, U, and J waveforms of a conventional ECG waveform. In other words, the device of the '204 Patent can provide information (subwaveforms) about different frequency domain signals from different parts of the heart muscle. A waveform displaying these subwaveforms is referred to as a saah ECG waveform, for example. In FIG. 30, described below, portions of a saah ECG waveform 3030 and a conventional or traditional ECG waveform 3040 are compared. FIG. 30 shows that saah ECG waveform 3030 relates ECG signals more closely to the anatomy of self-conducting system 3020 than traditional ECG waveform 3040.

As described in the '930 Patent and below, one way the different frequency domain signals from different parts of the heart muscle can be measured is through multi-domain ECG. In multi-domain ECG heart signals are measured using different frequency bands. These multi-domain ECG heart signals can be displayed in one diagram as an electrophysiocardiogram (EPCG) waveform. FIG. 32 shows EPCG waveforms before and after percutaneous coronary intervention (PCI), for example.

As a result of the systems of the '204 Patent and the '930 Patent, the technical problem of measuring the different frequency domain signals from different parts of the heart muscle has been addressed.

ECG Parameter Measurement Problem

The heart beats day and night from the first day of a human life to the last day of life. In a whole life, the heart beats about 2.5 billion to 3 billion times. In this regard, it could be calculated that the heart each time pumps 80 ml blood. Accordingly, based on the fact that the heart beats about 70 times per minute on average, the heart hence pumps 8,000 liters of blood per day, which is equivalent to the volume of 40 barrels of gasoline, and the total weight would be 8 tons. Therefore, the heart pumps 3,000 tons of blood per year. If a person lives for 80 years, the number will reach 240,000 tons. It is noted that after the age of 60 years old, a person has a 45% chance of having the condition of arrhythmia, and about half of those cases become life threatening. According to a variety of different scientific predictions, some scientists believe that it is reasonable to predict that the average lifespan of a person is about 80 years old.

The heart is a charged elastic mucus organ, so an ECG instrument is the only instrument that is able to scan and record the physiological and pathological signs of the cardiac electrophysiology (heart ultrasound provides hemodynamic data, CT & MIR provide histological imaging data). ECG provides electrophysiological signals, in particular noninvasive electrophysiological data. It is able to scan and record cardiac electrical conduction signals. By far, it is the only tool that can record the scanning image of "bioelectric conduction," the identifier of a living heart.

On the other hand, however, in the medical field, ECG is also only a morphological signal. It needs to be read and analyzed to determine its various waveforms. In this regard, it is an area that highly relies on a practitioner's experience. In the history of ECG, there are many data-based parameter gold standards, such as P-R interval, Q-T interval, ST segment, QRS complex, P-J interval, J-T interval, VAT.

However, due to the fact that ECG waveforms are prone to certain issues such as deformation, instability, standard point loss, and so on, conventional ECG instruments are unable to accurately measure these ECG parameters. As a result, many established standards cannot be applied in clinical practice.

Furthermore, as for the data measured manually, a very small variation can result in a difference of tens of milliseconds. Clinically, only simple standards can be used at present, such as: HR, RR interval, PP interval. As a result, only a few very simple standards can be used in current clinical practice, including HR, RR interval, PP interval, etc.

As described above, the ECG systems of the '204 Patent and the '930 Patent have addressed the technical problem of accurately measuring the different frequency domain signals from different parts of the heart muscle.

Additional systems and methods, however, are needed to accurately measure ECG parameters such as the P-R interval, Q-T interval, ST segment, QRS complex, P-J interval, J-T interval, and VAT so that these standards can be used in clinical practice.

ECG History

Electrical signals produced by a human heart were observed through electrodes attached to a patient's skin as early as 1879. Between 1897 and 1911 various methods were used to detect these electrical signals and record a heartbeat in real-time. In 1924, Willem Einthoven was awarded the Nobel Prize in medicine for identifying the various waveforms of a heartbeat and assigning the letters P, Q, R, S, T, U, and J to these waveforms. Since the early 1900s, the equipment used for electrocardiography (ECG or EKG) has changed. However, the basic waveforms detected and analyzed have not changed.

An ECG device detects electrical impulses or changes in the electrical potential between two electrodes attached to the skin of a patient as the heart muscle contracts or beats. Electrically, the contraction of the heart is caused by depolarization and repolarization of various parts of the heart muscle. Initially, or at rest, the muscle cells of the heart have a negative charge. In order to cause them to contract, they receive an influx of positive ions $Na^+$ and $Ca^{++}$. This influx of positive ions is called depolarization. The return of negative ions to bring the heart back to a resting state is called repolarization. Depolarization and repolarization of the heart affect different parts of the heart over time giving rise to the P, Q, R, S, T, U, and J waveforms.

FIG. 2 is an exemplary plot 200 of the P, Q, R, S, and T waveforms of a conventional ECG waveform of a heartbeat from a conventional ECG device. The P, Q, R, S, and T waveforms represent electrical conduction through a heart muscle. P waveform 210 represents the propagation of depolarization from the sinoatrial node, to the right and left atriums, and to the atrioventricular node. The sinoatrial node is also referred to as the sinus node, SA node, or SAN. The atrioventricular node is also referred to as the AV node or AVN. The right atrium is also referred to as the RA, and the left atrium is also referred to as the LA.

FIG. 3 is an exemplary diagram 300 of the depolarization of the muscle tissue of a heart that produces P waveform 210 of FIG. 2 as detected by a conventional ECG device. P waveform 210 of FIG. 2 is produced as depolarization propagates from SAN 310 to AVN 340 in FIG. 3. As depolarization propagates from SAN 310 to AVN 340, it also spreads from RA 320 to LA 340. P waveform 210 of FIG. 2 typically has a duration of 80 ms, for example.

PR segment 220 of FIG. 2 represents the propagation of depolarization from the AVN to the Bundle of His, and then to the Bundle Branches. PR segment 230 may also include depolarization to the Purkinje fibers of the inner ventricular walls. The Bundle of His is also referred to as the His Bundle or His. The Bundle Branches include the right bundle branches (RBB) and the left bundle branches (LBB). As shown in FIG. 2, in a conventional ECG, PR segment 220 shows up as a flat line or waveform with no amplitude.

FIG. 4 is an exemplary diagram 400 of the depolarization of the muscle tissue of a heart that produces PR segment 220 of FIG. 2 as detected by a conventional ECG device. PR segment 220 of FIG. 2 is produced as depolarization propagates from AVN 340 to His 450 and then to Bundle Branches 460 that include RBB 461 and LBB 462. PR segment 220 of FIG. 2 typically has a duration of between 50 and 120 ms, for example.

Waveforms Q 230, R 240, and S 250 of FIG. 2 form the QRS complex. The QRS complex represents the propagation of depolarization through the right and left ventricles. The right ventricle is also referred to as RV, and the left ventricle is referred to as LV.

FIG. 5 is an exemplary diagram 500 of the depolarization of the muscle tissue of a heart that produces Q waveform 230, R waveform 240, and S waveform 250 of FIG. 2 as detected by a conventional ECG device. Waveforms Q 230, R 240, and S 250 of FIG. 2 produced as depolarization propagates from Bundle Branches 460 through RV 571 and LV 572. RV 571 and LV 572 have the largest muscle mass in the heart. The QRS complex formed by waveforms Q 230, R 240, and S 250 of FIG. 2 typically has a duration of between 80 and 100 ms, for example.

ST segment 260 of FIG. 2 represents the period during which the ventricles remain depolarized and contracted. As shown in FIG. 2, in a conventional ECG, ST segment 260 shows up as a flat line or waveform with no amplitude. ST segment 260 typically has a duration of between 80 and 120 ms, for example.

The point in FIG. 2 at which the QRS complex ends and ST segment 260 begins is called J point 255. A J waveform (not shown) can sometimes appear as an elevated J point at J point 255 or as a secondary R waveform. A J waveform is usually characteristic of a specific disease. The J waveform is also referred to as the Osborn wave, camel-hump sign, late delta wave, hathook junction, hypothermic wave, prominent J wave, K wave, H wave or current of injury.

T waveform 270 of FIG. 2 represents the repolarization or recovery of the ventricles. T waveform 270 typically has a duration of 160 ms, for example. The interval between the Q and T waveforms is referred to as the QT interval.

FIG. 6 is an exemplary diagram 600 of the repolarization of the muscle tissue of a heart that produces T waveform 270 of FIG. 2 as detected by a conventional ECG device. As shown in FIG. 6, RV 571 and LV 572 are repolarized.

Not shown in FIG. 2 is the U waveform. The U waveform sometimes appears after the T waveform. The U waveform is thought to represent repolarization of the interventricular septum, the papillary muscles, or the Purkinje fibers.

As shown in FIGS. 3 through 6, as a heart beats, electrical signals flow through all the different muscle tissues of the heart. As shown in FIG. 2, for the last 100 years conventional ECG devices have been able to detect some of these signals in the form of the P, Q, R, S, T, U, and J waveforms. These waveforms have aided in the diagnosis and treatment of many heart problems. Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

Artificial Intelligence

Artificial Intelligence (AI) generally refers to languages, algorithms, and operating systems that relate to how a computer system can carry out tasks that were previously only completed by relying on human intelligence. It is a general term and often does not include implementation or application. The definition of AI has evolved over time, however, and this phenomenon is referred to as the "AI effect." The AI effect can be summarized as the prescription that "AI intends to complete a collection of all tasks that cannot be implemented without relying on human intelligence at the present." In the 1940s and 1950s, a group of scientists from different fields (mathematics, psychology, engineering, economics and politics) began to explore the possibility of manufacturing an artificial brain. In 1956, AI was established as a discipline. The organizers of the 1956 Dartmouth Artificial Intelligence Conference were Marvin Minsky, John McCarthy, and two other senior scientists, Claude Shannon and Nathan Rochester, with the latter coming from IBM. At the 1956 Dartmouth Artificial Intelligence Conference, the name and tasks of AI were determined, and at the same time, initial achievements and the earliest group of researchers appeared. As a result, this event has been extensively acknowledged as a sign of the birth of AI. It is clear that AI is now a technological field, a second revolution since the invention of the computer, and a certain trend in the future. It is being applied in all industries, exists everywhere, and is used on almost everything on the earth. In the medical field, AI is now used in the following: medical imaging, sensor-based data analysis, conversion of bioinformatics, and development of public health policies. AI is also used in the clinical applications. These applications include cancer treatment: recognition of mitosis of cancerous tumor cells, identification of disease types and degrees of aggravation, shortening chemotherapy time, and mitigating damage caused by chemotherapy for cancer patients. These applications also include ophthalmological diagnosis: recognition of early signs of eye disease, such as senile macular degeneration, and diabetic retinopathy and surgical treatment: AI surgical robots, etc. Google has also formed a team called DeepMind Health, which cooperated with the Imperial College London and the Royal Free Hospital in London, UK. They released a mobile application called Streams, and medical professionals can use Streams to observe treatment results in a faster manner. Overall, in the medical field, the AI system can be used on any job that previously required human thinking.

BRIEF DESCRIPTION OF THE DRAWINGS

FIG. 45 is an exemplary comparison of two ECG waveform plots exhibiting ST segment changes that can be identified using the STy standard, in accordance with various embodiments.

FIG. 46 is an exemplary comparison of two ECG waveform plots exhibiting ST segment changes that can be identified using the STx standard, in accordance with various embodiments.

FIG. 47 is an exemplary comparison of two ECG waveform plots exhibiting ST segment changes that can be identified using the STs and STy standards (STs+STy), in accordance with various embodiments.

FIG. 48 is an exemplary comparison of two ECG waveform plots exhibiting ST segment changes that can be identified using the STj, STy, and STx standards (STj+STy+STx), in accordance with various embodiments.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DETAILED DESCRIPTION

Computer-Implemented System

Figure 1:
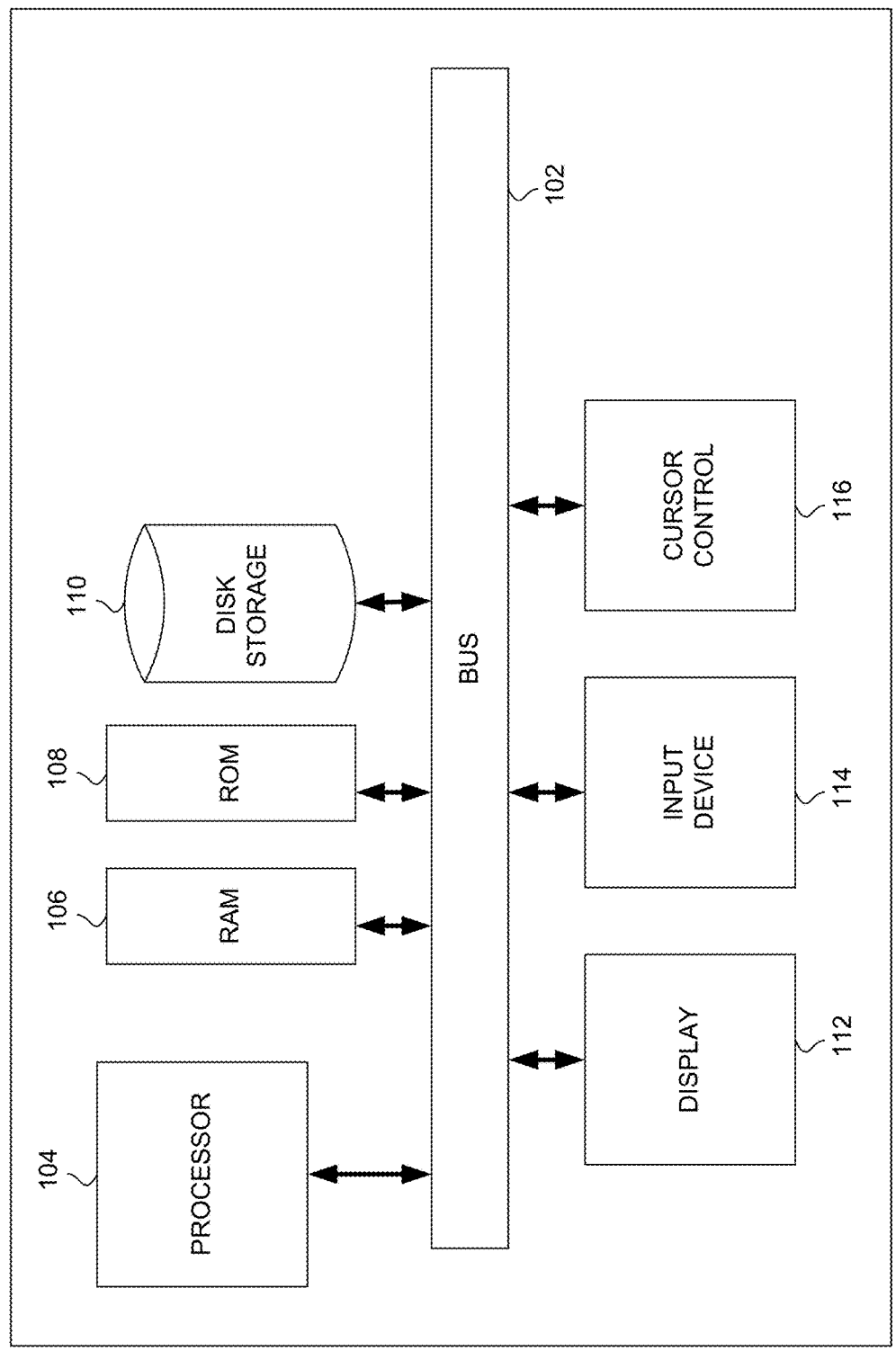
FIG. 1 is a block diagram that illustrates a computer system, in accordance with various embodiments.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer-readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Subwaveform Detection of the P, Q, R, S, T, U, and J Waveforms

As described above, electrical signals flow through all the different muscle tissues of the heart. For the last 100 years, conventional ECG devices have been able to detect some of these signals in the form of the P, Q, R, S, T, U, and J waveforms. These waveforms have aided in the diagnosis and treatment of many heart problems.

Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

In various embodiments, additional information is obtained from the electrical signals produced by a heart through signal processing. More specifically, signal processing is added to an ECG device in order to detect more information from the electrical signals that flow through all the different muscle tissues of the heart as it is beating.

Figure 7:
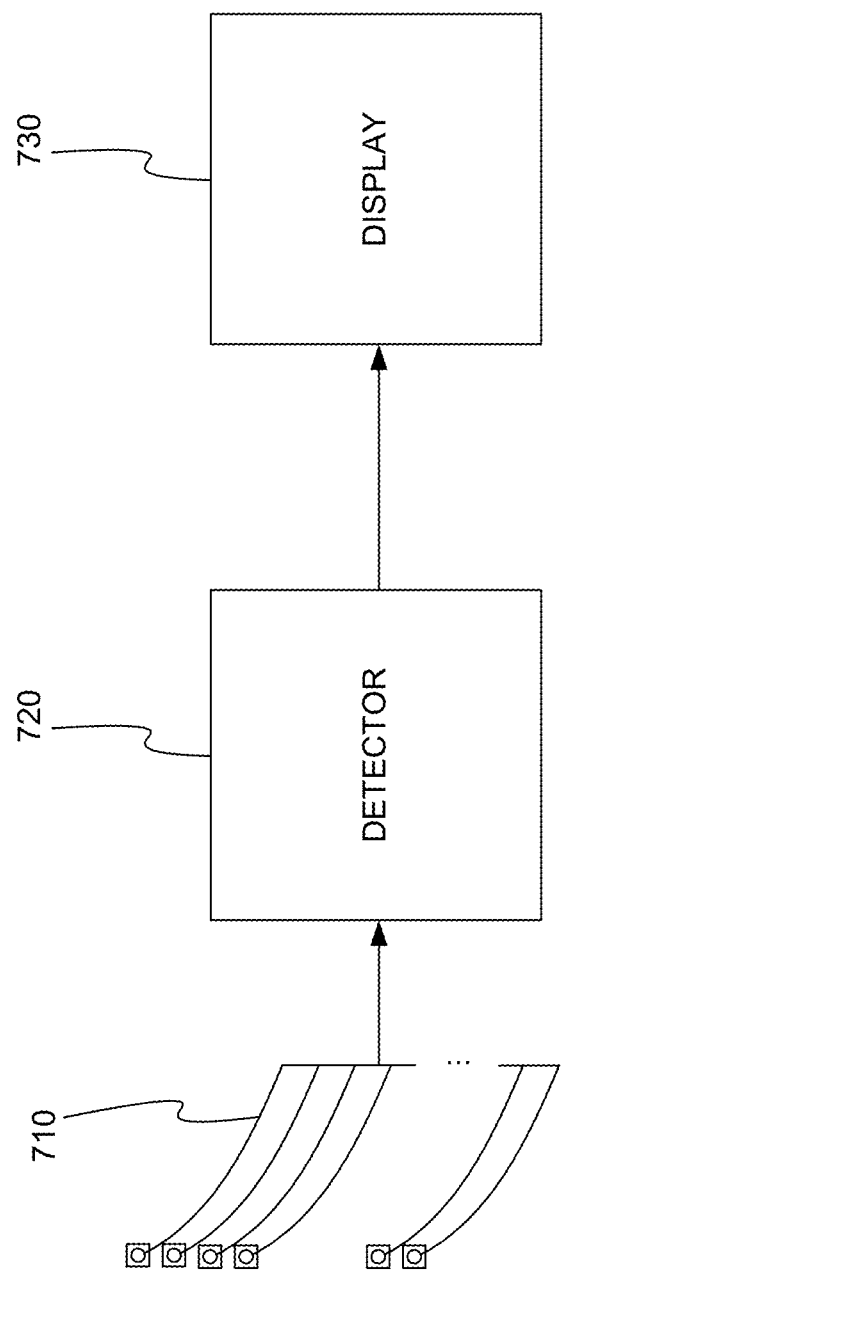
FIG. 7 is a block diagram of a conventional ECG device.

FIG. 7 is a block diagram 700 of a conventional ECG device. The conventional ECG device includes two or more leads or electrodes 710. Electrodes 710 are typically attached to the skin of a patient. Electrical signals produced by a beating heart are detected between pairs of electrodes 710. Because the heart is three-dimensional, electrodes are attached at different locations on a body to detect signals at different corresponding locations or angles from the heart. In other words, the electrodes are placed on a body to partially surround the heart. One typical type of ECG includes 12 electrodes, for example.

A voltage signal is detected between two electrodes 710 by detector 720. Detector 720 also typically amplifies the voltage signal. Detector 720 can also convert the voltage signal to a digital voltage signal using an analog to digital converter (A/D).

Detector 720 provides the detected and amplified voltage signal from each pair of electrodes 710 to display 730. Display 730 can be an electronic display device including, but not limited to, a cathode ray tube (CRT) device, light emitting diode (LED) device, or Liquid crystal display (LCD) device. Display 730 can also be a printer device. Additionally, display 730 can include a memory device to record detected signals. The memory device can be, but is not limited to, a volatile electronic memory, such as random access memory (RAM), a non-volatile electronic memory, such as electrically eras, hie programmable read-only memory (EEPROM or Flash memory), or a magnetic hard drive.

Figure 2:
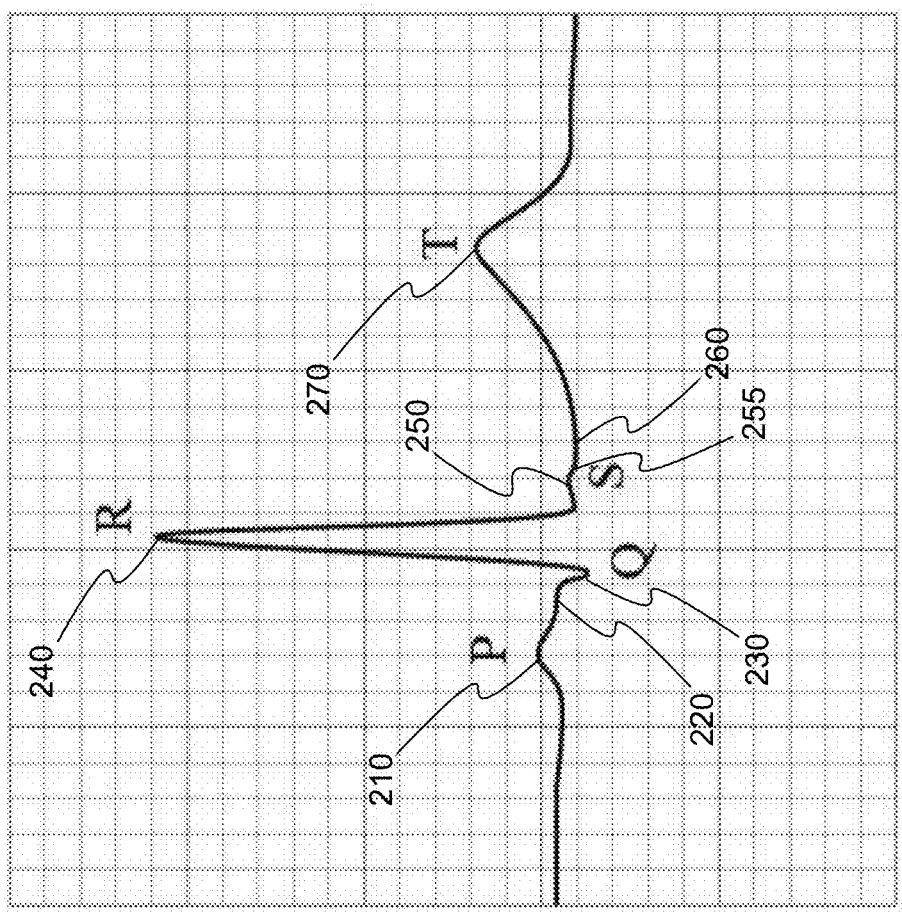
FIG. 2 is an exemplary plot of the P, Q, R, S, and T waveforms of a conventional electrocardiography (ECG) waveform of a heartbeat from a conventional ECG device.
Figure 3:
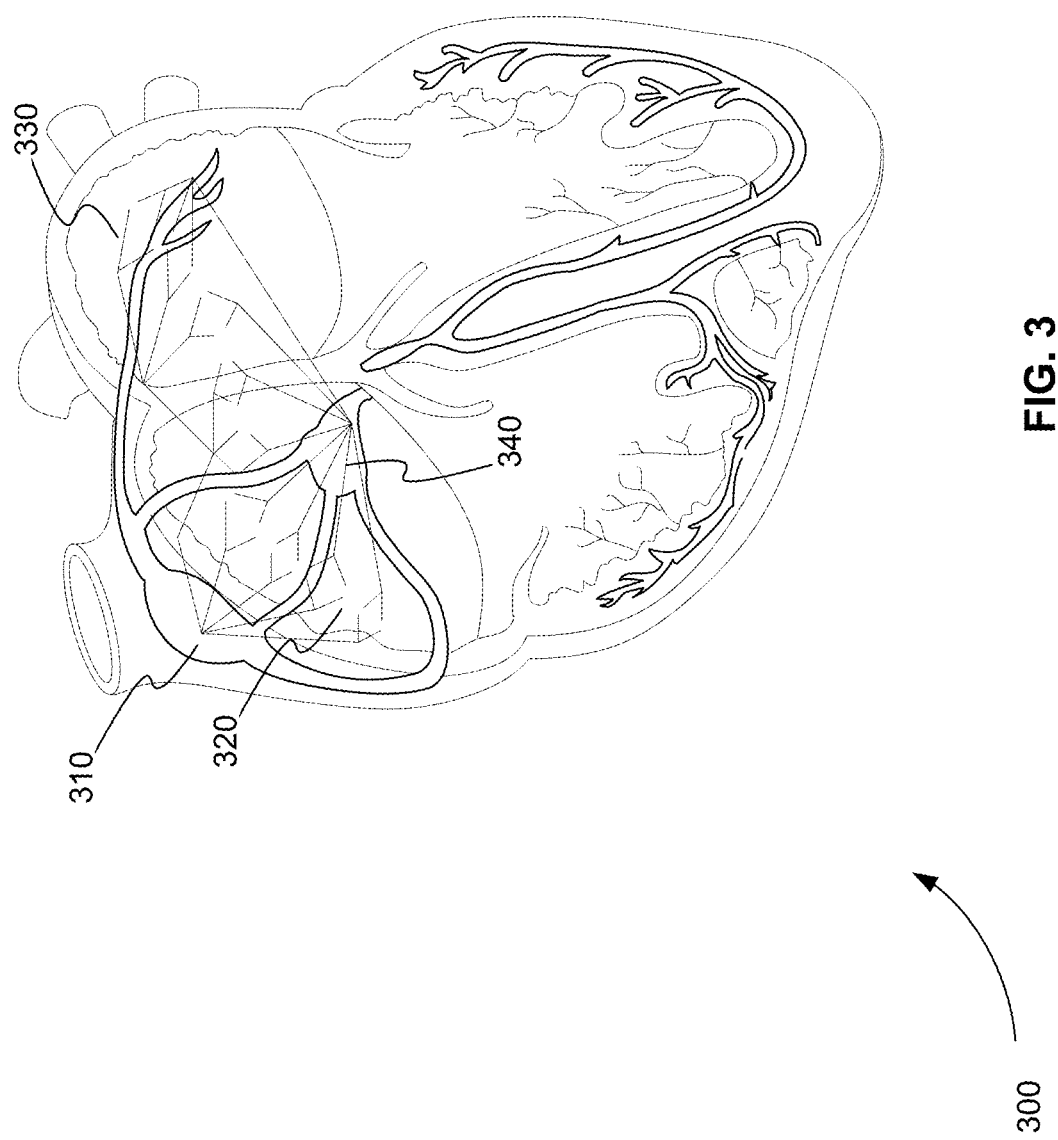
FIG. 3 is an exemplary diagram of the depolarization of the muscle tissue of a heart that produces the P waveform of FIG. 2 as detected by a conventional ECG device.
Figure 4:
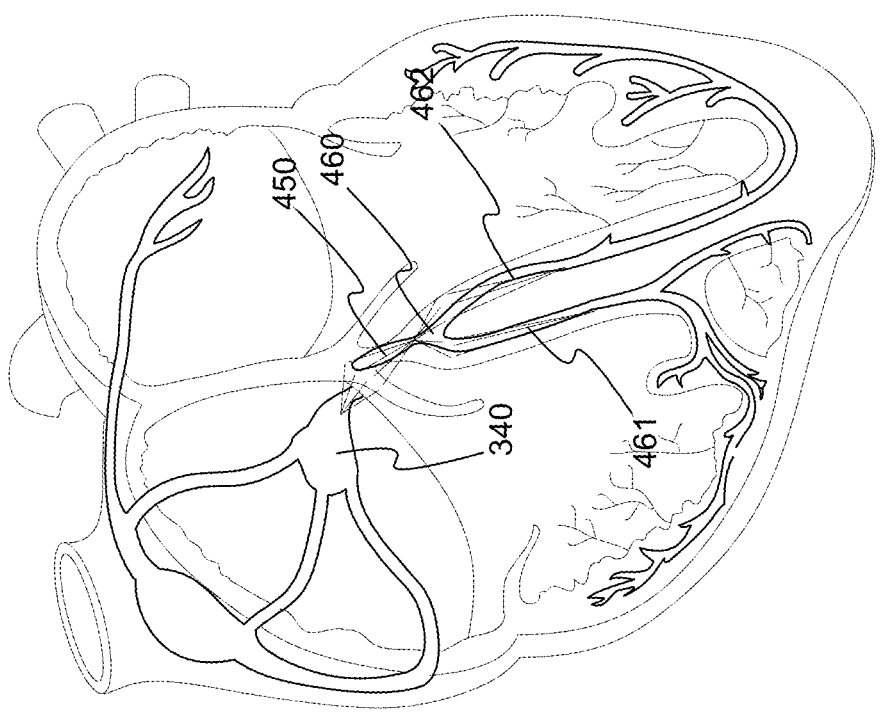
FIG. 4 is an exemplary diagram of the depolarization of the muscle tissue of a heart that produces the PR segment of FIG. 2 as detected by a conventional ECG device.
Figure 5:
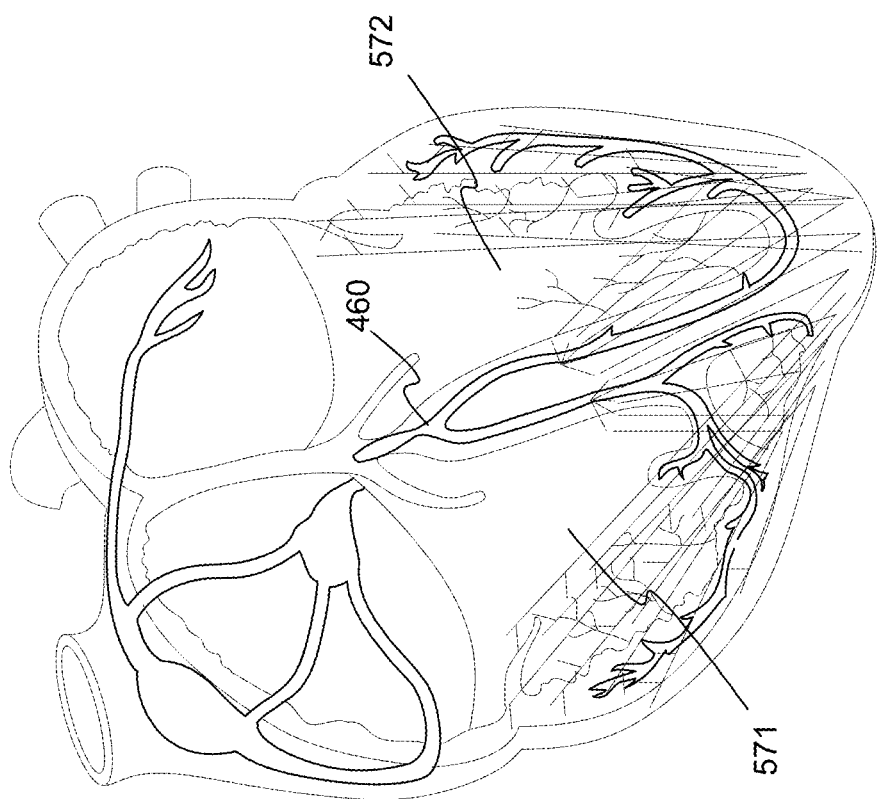
FIG. 5 is an exemplary diagram of the depolarization of the muscle tissue of a heart that produces the Q waveform, the R waveform, and the S waveform of FIG. 2 as detected by a conventional ECG device.
Figure 6:
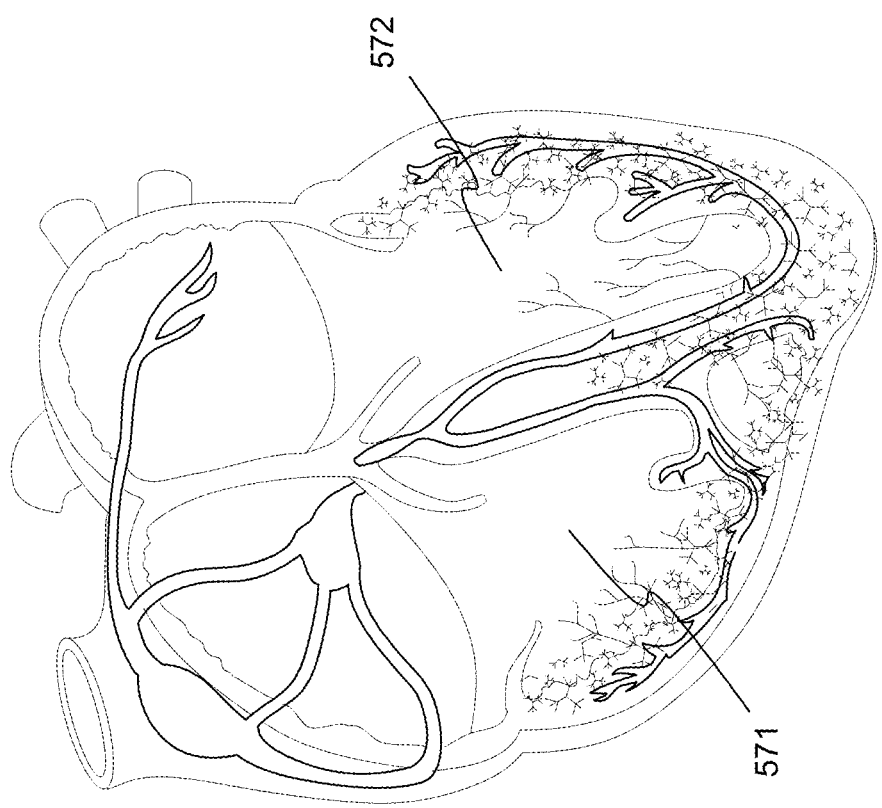
FIG. 6 is an exemplary diagram of the repolarization of the muscle tissue of a heart that produces the T waveform of FIG. 2 as detected by a conventional ECG device.

Display 730 displays a continuous loop of the detected P, Q, R, S, T, U, and J waveforms as shown in FIG. 2 for each pair of electrodes 710. Modern ECG devices can also include a processor (not shown), such as the processor shown in FIG. 1, to analyze the P, Q, R, S, T, U, and J waveforms. For example, the processor can calculate the time periods of the P, Q, R, S, T, U, and J waveforms and the times between the P, Q, R, S, T, U, and J waveforms. The processor can also compare this timing information to stored normal information. Based on the comparison, the processor can determine differences from the normal data. All information calculated by the processor can also be displayed on display 730.

Figure 8:
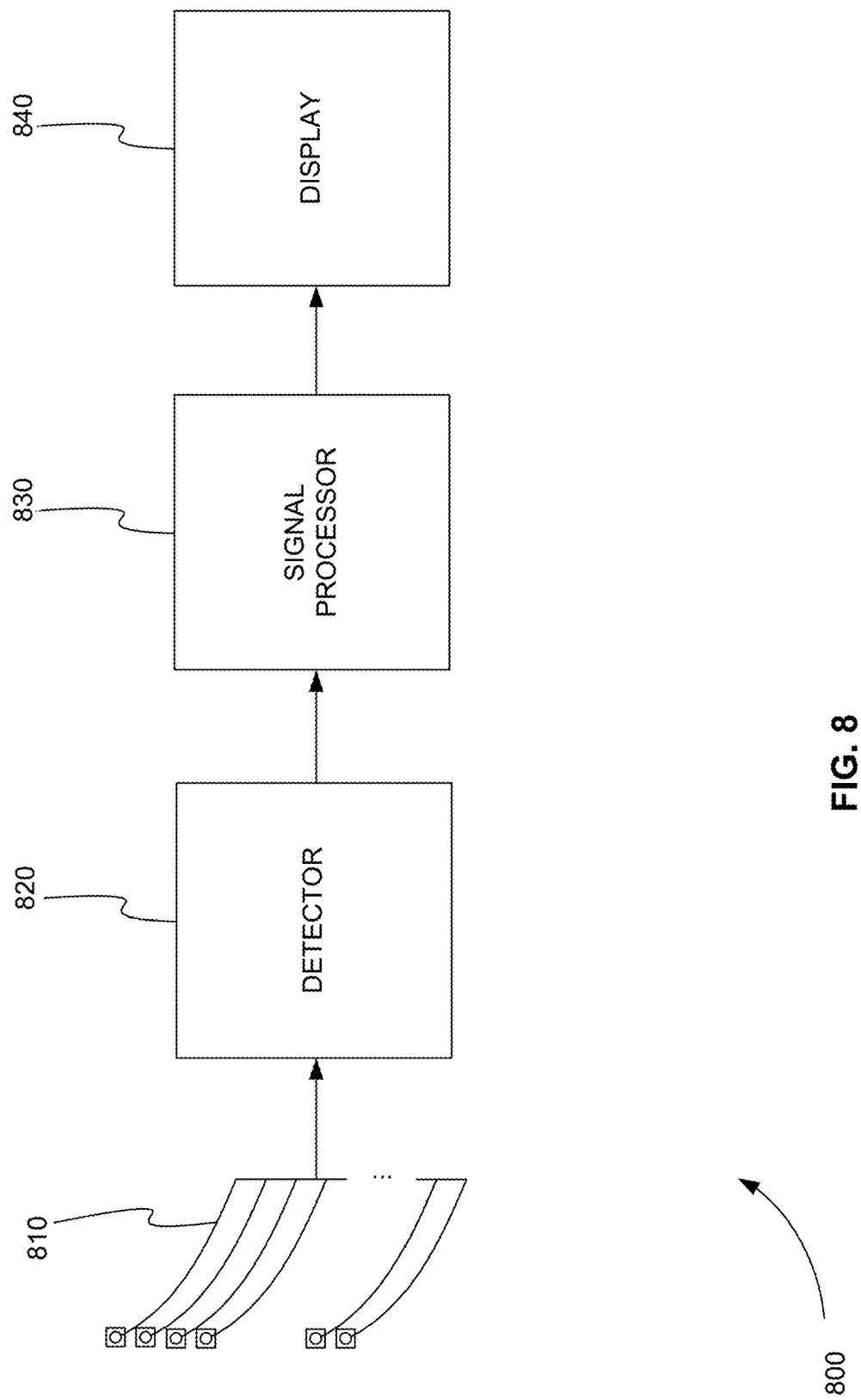
FIG. 8 is a block diagram of an ECG device for detecting more information from the electrical signals that flow through all the different muscle tissues of the heart as it is beating, in accordance with various embodiments.

FIG. 8 is a block diagram 800 of an ECG device for detecting more information from the electrical signals that flow through all the different muscle tissues of the heart as it is beating, in accordance with various embodiments. Electrodes 810 are attached to the skin of a patient, for example. Electrical signals produced by a beating heart are detected between pairs of electrodes 810.

A voltage signal is detected between two electrodes 810 by detector 820. Detector 820 also amplifies the voltage signal. Detector 820 also converts the voltage signal to a digital voltage signal using an analog to digital converter (A/D).

Detector 820 provides the detected and amplified voltage signal from each pair of electrodes 810 to signal processor 830. Detector 820 can also provide the detected and amplified voltage signal from each pair of electrodes 810 directly to display device 840 to display the conventional P, Q, R, S, T, U, and J waveforms.

Signal processor 830 detects or calculates one or more subwaveforms within and/or in the interval between the P, Q, R, S, T, U, and J waveforms of each detected and amplified voltage signal. A waveform is a shape or form of a signal. A subwaveform is shape or form of a signal that is within or part of another signal.

Signal processor 830 can be a separate electronic device that can include, but is not limited to, an application specific integrated circuit (ASIC), a field programmable gate array (FPGA), or a general purpose processor. Signal processor 830 can be software implemented on another processor of the ECG device, such as a processor of display device 840. Signal processor 830 can also be a remote server that receives the detected and amplified voltage signal from detector 820, detects or calculates one or more subwaveforms within and/or in the interval between the P, Q, R, S, T, U, and J waveforms, and sends the detected and amplified voltage signal and the one or more subwaveforms to display device 840.

Signal processor 830 sends one or more subwaveforms of each detected and amplified voltage signal to display device 840. Signal processor 830 can also calculate and send to the display device 840 the time periods of the one or more subwaveforms, the times between the one or more subwaveforms, and the times of the one or more subwaveforms in relation to the P, Q, R, S, T, U, and J waveforms and or the intervals between the P, Q, R, S, T, U, and J waveforms. Signal processor 830 can also compare this timing information to stored normal timing information. Based on the comparison, signal processor 830 can determine differences from the normal data and send this difference information and any of the timing information to display device 840.

Display device 840 displays a continuous loop of the one or more subwaveforms for each pair of electrodes 810. Display device 840 can also display part or all of the conventional P, Q, R, S, T, U, and J waveforms for comparison with the one or more subwaveforms. Like display 730 of FIG. 7, display device 840 of FIG. 8 can be an electronic display device, a printer, or any combination of the two.

In various embodiments, an ECG device using signal processing to detect one or more subwaveforms within the P, Q, R, S, T, U, and J waveforms and/or within the intervals between the P, Q, R, S, T, U, and J waveforms is herein referred to as a saah ECG device. The voltage difference signals produced by a saah ECG device are referred to as saah ECG waveforms. The term "saah" is an acronym for some of the anatomically distinct portions of muscle tissue that produce subwaveforms. Specifically, saah stands for sinoatrial node (SAN), atria (right atrium (RA) and left atrium (LA)), atrioventricular node (AVN), and bundle of His (HIS). However, a saah ECG waveform is not limited to including subwaveforms representing the SAN, the atria, the AVN, and the HIS. A saah ECG waveform can include any subwaveform the P, Q, R, S, T, U, and J waveforms and/or within the intervals between the P, Q, R, S, T, U, and J waveforms.

Figure 9:
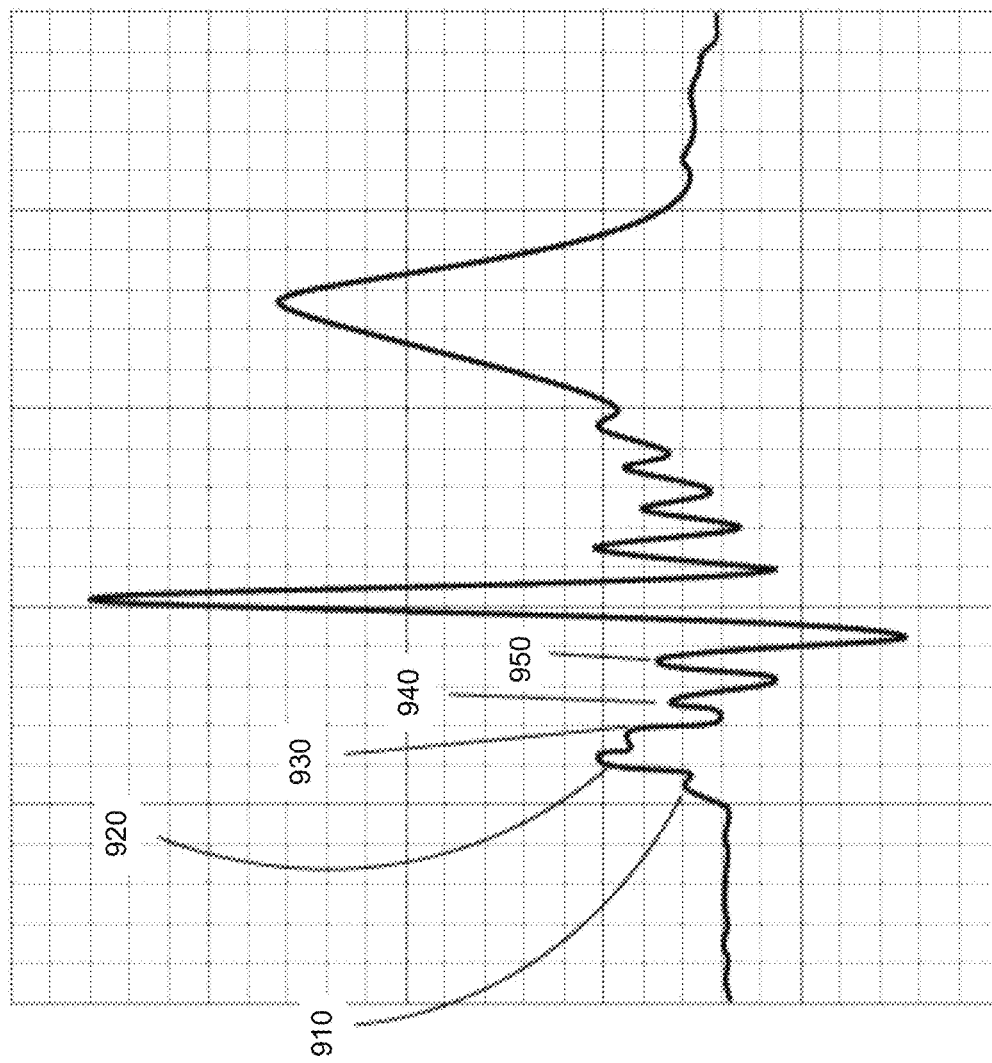
FIG. 9 is an exemplary plot of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments.

FIG. 9 is an exemplary plot 900 of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments. For example, five subwaveforms 910-950 of FIG. 9 are detected within the P waveform and the PR segment. The time period that includes the P waveform and the PR segment is also called the PR interval. Subwaveform 910 represents the depolarization of the SAN. Subwaveform 920 represents the depolarization of RA and LA. Subwaveform 930 represents the depolarization of the AVN. Subwaveform 940 represents the depolarization HIS. Finally, subwaveform 950 represents the depolarization of the bundle branches (BB).

In various embodiments, the subwaveforms of a saah ECG waveform are detected using signal processing. Electrodes 810 of the saah ECG of FIG. 8, for example, receive electrical impulses from anatomically distinct portions of muscle tissue or cells. The electrical impulses of anatomically distinct portions of muscle tissue of the heart have distinct frequencies. Through animal and human experimentation, the distinct frequency, frequency range, or frequency band of the anatomically distinct portions of muscle tissue of the heart are found. These distinct frequency bands of anatomically distinct portions of muscle tissue of the heart provide predetermined data or information for signal processing. In other words, the band pass frequency filtering of the signal processing is determined from the experimental data collected. A saah ECG device then employs one or more frequency band pass filters to detect the one or more subwaveforms.

Figure 10:
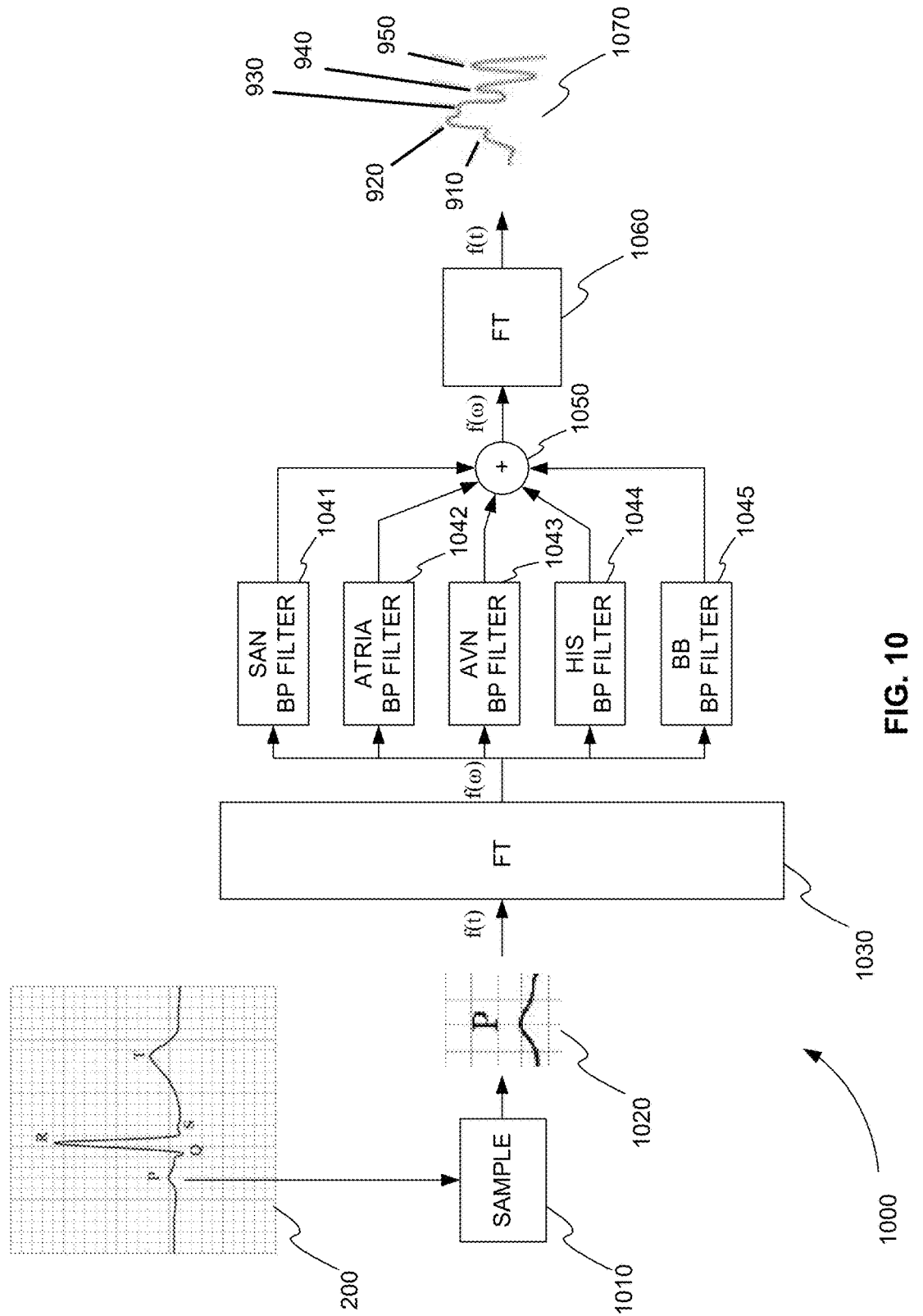
FIG. 10 is an exemplary block diagram showing a signal processing algorithm for detecting five subwaveforms within the PR interval of a conventional ECG waveform, in accordance with various embodiments.

FIG. 10 is an exemplary block diagram 1000 showing a signal processing algorithm for detecting five subwaveforms within the PR interval of a conventional ECG waveform, in accordance with various embodiments. Sampling block 1010 samples the electrical impulses in the PR interval time period of each heart. This is shown graphically in FIG. 10 by separating PR interval 1020 from ECG waveform 200. The electrical impulses in the PR interval time period are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 10, block 1030 converts the PR interval time domain signal to a PR interval frequency domain signal. The time domain signal is converted into a frequency domain signal using a Fourier transform, for example.

As described above, through animal and/or human experimentation, the frequency bands associated with depolarization of the SAN, atria, AVN, HIS, and BB of the heart are determined. Based on these frequency bands, band pass filters are created. Blocks 1041-1045 represent the band pass filters created to filter the PR interval frequency domain signal for frequency bands of the SAN, atria, AVN, HIS, and BB of the heart, respectively.

In block 1050, the frequency domain subwaveforms detected from the band pass filtering the frequency bands of the SAN, atria, AVN, HIS, and BB of the heart are summed. In block 1060, the filtered and summed frequency domain signal of the PR interval is converted back to a time domain signal. The frequency domain signal is converted into a time domain signal using a Fourier transform, for example.

The PR interval filtered and summed time domain signal 1070 includes five time domain subwaveforms 910-950. Subwaveforms 910-950 represent depolarization of the SAN, atria, AVN, HIS, and BB of the heart, respectively.

Time domain signal 1070 can be used to replace PR interval 1020 in ECG waveform 200, for example. As a result, a saah ECG waveform is produced.

FIG. 10 shows a signal processing algorithm for detecting five subwaveforms. However, similar steps can be applied to detect fewer than five waveforms or more than five waveforms. Also, the steps of FIG. 10 describe detecting subwaveforms within the PR interval. However, similar steps can be applied to detect subwaveforms within the P, Q, R, S, T, U, and J waveforms and/or within one or more of the intervals between the P, Q, R, S, T, U, and J waveforms. In addition, the steps of FIG. 10 describe converting time signals to the frequency domain and then back to the time domain. One of ordinary skill in the art can appreciate that band pass filters can be applied directly to the time domain signal to provide the same result.

Figure 11:
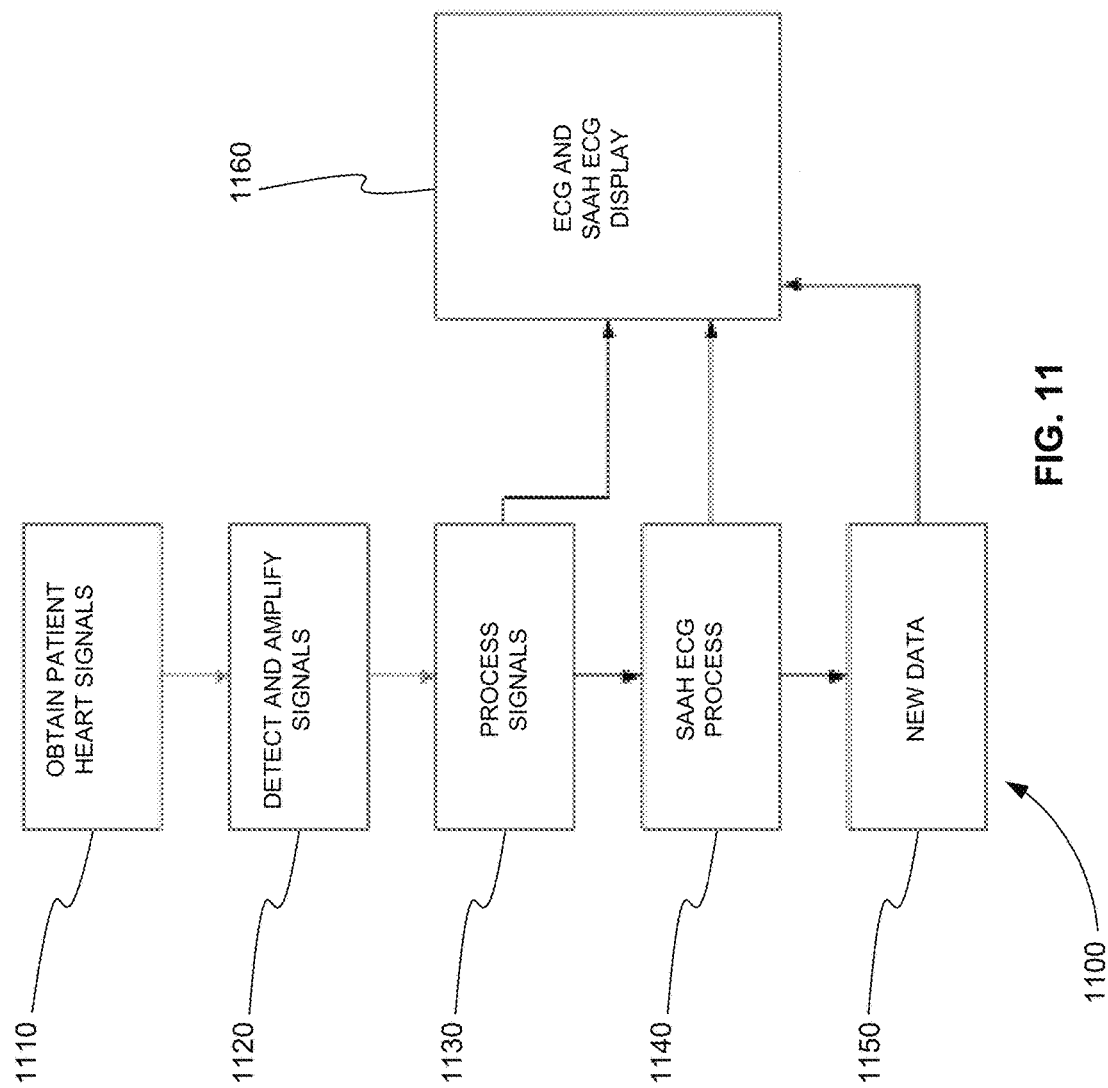
FIG. 11 is an exemplary block diagram of a saah ECG device that displays conventional ECG waveforms, saah ECG waveforms, and saah ECG data, in accordance with various embodiments.

FIG. 11 is an exemplary block diagram 1100 of a saah ECG device that displays conventional ECG waveforms, saah ECG waveforms, and saah ECG data, in accordance with various embodiments. In block 1110, patient heart signals are obtained. These heart signals can be obtained through noninvasive electrodes placed on the skin, such as electrodes 810 shown in FIG. 8. In various embodiments, heart signals may also be obtained using invasive electrodes placed directly on the heart. In block 1120, the heart signals are detected using a detector and amplified.

In block 1130, the detected and amplified heart signals are processed using a signal processor. The signal processor detects the conventional P, Q, R, S, T, U, and J waveforms and sends them to the display of block 1160. The signal processor also detects or calculates subwaveforms within the conventional P, Q, R, S, T, U, and J waveforms and/or within intervals between the conventional P, Q, R, S, T, U, and J waveforms. The signal processor sends the subwaveforms to block 1140 for further processing. The processor of block 1140 produces the saah ECG waveform that includes the subwaveforms and sends the saah ECG waveform to the display of block 1160. The processor of block 1140 calculates additional information or new data from the saah ECG waveform. This new data can include, but is not limited to, timing information about the subwaveforms, timing information about the intervals between the subwaveforms, and timing information about the subwaveforms and their relation to the conventional P, Q, R, S, T, U, and J waveforms. In block 1150, this new data is sent to the display of block 1160.

The display of block 1160 displays a continuous loop of the conventional ECG waveform, the saah ECG waveform, and the new data from the subwaveforms. The display of block 1160 can display this information on an electronic display or print it on paper. The display of block 1160 can also record this information. The display of block 1160 can record this information on any type of memory device.

Figure 12:
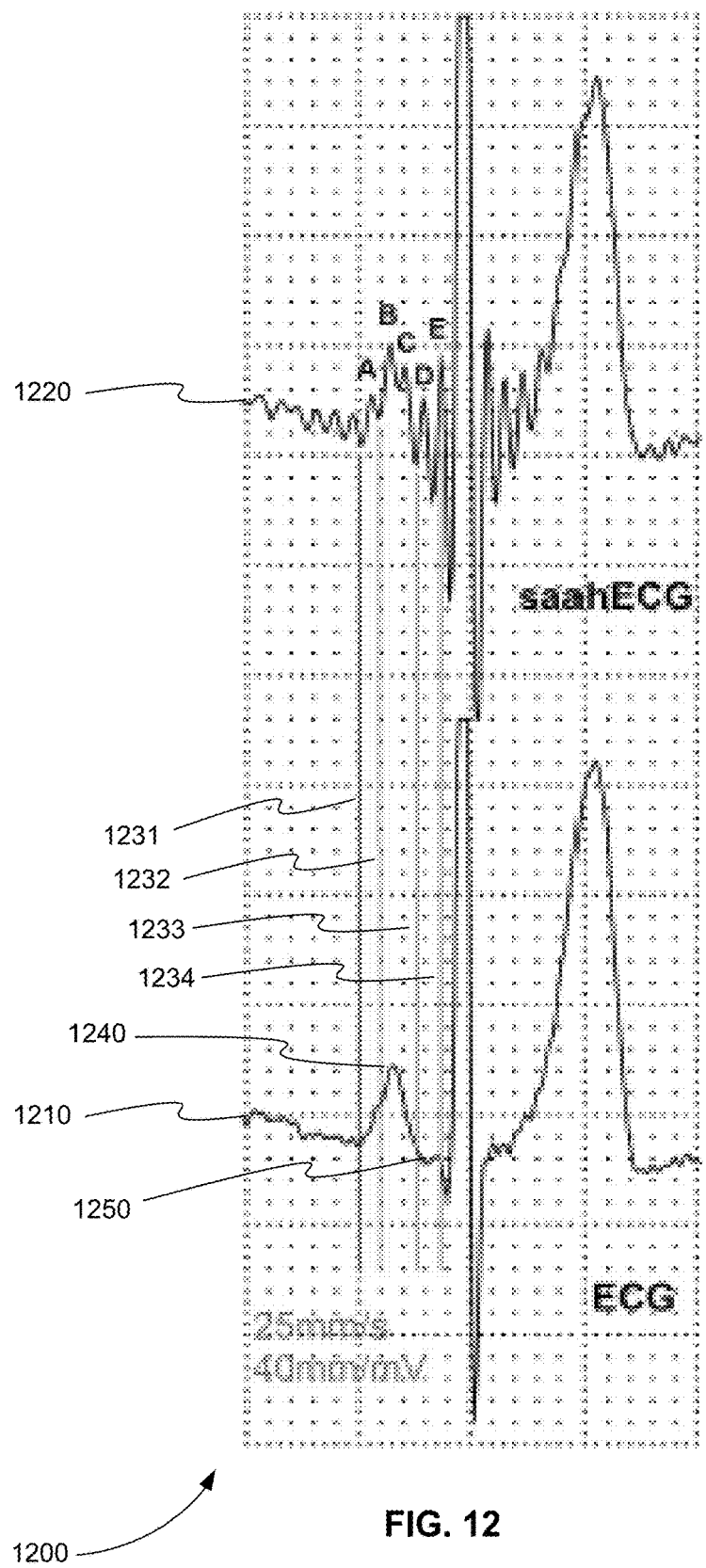
FIG. 12 is an exemplary plot of the information displayed by the saah ECG device of FIG. 10, in accordance with various embodiments.

FIG. 12 is an exemplary plot 1200 of the information displayed by the saah ECG device of FIG. 11, in accordance with various embodiments. Plot 1200 includes conventional ECG waveform 1210 and saah ECG waveform 1220. Saah ECG waveform 1220, for example, includes, among others, five subwaveforms A-E representing the depolarization of the SAN, the RA and LA, the AVN, the HIS, and the BB, respectively.

Plot 1200 also shows new data or timing information about the subwaveforms and their relation to the conventional P, Q, R, S, T, U, and J waveforms. For example, the time interval between line 1231 and line 1232 relates subwaveform A of saah ECG waveform 1220 to P waveform 1240 of conventional ECG waveform 1210. The time interval between line 1232 and line 1233 relates subwaveforms B and C of saah ECG waveform 1220 to P waveform 1240 conventional ECG waveform 1210. The time interval between line 1233 and line 1234 relates subwaveforms D and E of saah ECG waveform 1220 to PR segment 1250 conventional ECG waveform 1210.

Figure 13:
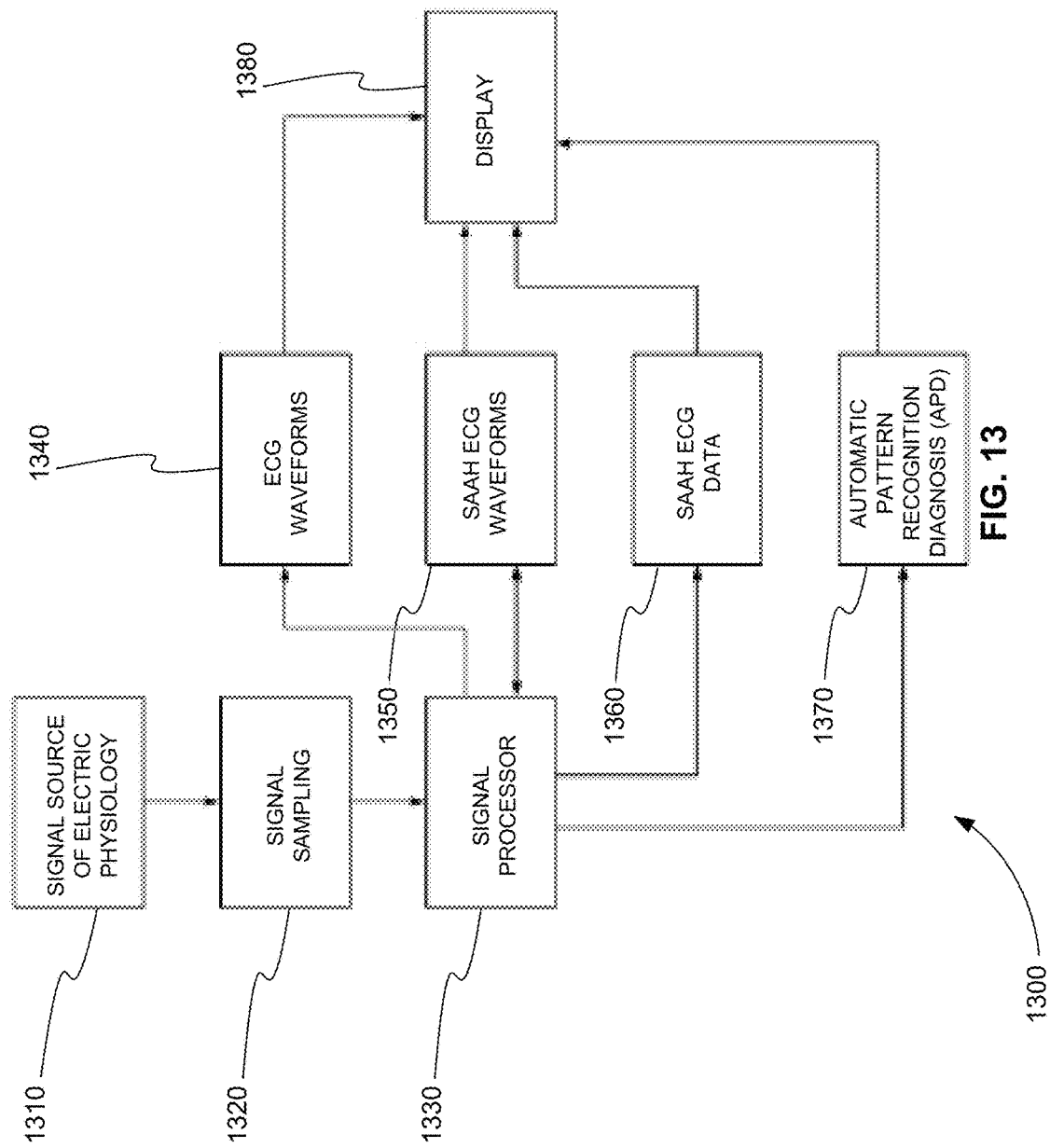
FIG. 13 is an exemplary block diagram of a saah ECG device that displays conventional ECG waveforms, saah ECG waveforms, saah ECG data, and saah ECG automatic pattern recognition diagnosis information, in accordance with various embodiments.

FIG. 13 is an exemplary block diagram 1300 of a saah ECG device that displays conventional ECG waveforms, saah ECG waveforms, saah ECG data, and saah ECG automatic pattern recognition diagnosis information, in accordance with various embodiments. In block 1310, patient heart signals are obtained. These heart signals can be obtained through noninvasive electrodes placed on the skin, such as electrodes 810 shown in FIG. 8. In various embodiments, heart signals may also be obtained using invasive electrodes placed directly on the heart. In block 1320, the heart signals are sampled or detected using a detector. The heart signals may also be amplified.

In block 1330, the sampled heart signals are processed using a signal processor. The signal processor produces four different types of information from the sampled heart signals. As shown in block 1340, the signal processor produces conventional ECG waveforms including the conventional P, Q, R, S, T, U, and J waveforms and sends them to display 1380. As shown in block 1350, the signal processor produces saah ECG waveforms. These saah ECG waveforms include subwaveforms of the conventional P, Q, R, S, T, U, and J waveforms and the intervals between them. Note that the arrow between blocks 1330 and 1350 show information following in both directions. This shows that information from the saah ECG waveforms is further analyzed by the signal processor.

As shown in block 1360, the signal processor further analyzes the saah ECG waveforms to produce saah ECG data. This saah ECG data is sent to display 1380. Additionally, as shown in block 1370, the signal processor further analyzes the saah to obtain endocardium and epicardium data. This data is compared to recorded normal and abnormal data. The signal processor then produces automatic pattern recognition diagnosis (APD) information, and this information is sent to display 1380. APD information is, for example, patterns and/or colors that allow a user to easily and quickly determine that normal or abnormal endocardium and/or epicardium data was found.

Systems and methods for detecting ECG subwaveforms are described in the '204 Patent, which is incorporated by reference in its entirety.

System for Detecting ECG Subwaveforms

In various embodiments, an electrocardiography (ECG) system for detecting one or more subwaveforms within the P, Q, R, S, T, U, and J waveforms or in an interval between the P, Q, R, S, T, U, and J waveforms is provided. Returning to FIG. 8, the ECG system includes two or more electrodes 810, a detector 820, a signal processor 830, and a display device 840.

Two or more electrodes 810 are placed near a beating heart and receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses.

In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor 830 receives the ECG waveform from detector 820. Signal processor 830 detects or calculates one or more subwaveforms within P, Q, R, S, T, U, and J waveforms of the ECG waveform or in an interval between the P, Q, R, S, T, U, and J waveforms that represent the depolarization or repolarization of anatomically distinct portions of muscle tissue of the beating heart. Signal processor 830 produces a processed ECG waveform that includes the one or more subwaveforms for each heartbeat.

Signal processor 830 can be a separate device, can be software running on a device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general purpose processor. A general purpose processor can include, but is not limited to, a microprocessor, a microcontroller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820, detects or calculates one or more subwaveforms within and/or in the interval between the P, Q, R, S, T, U, and J waveforms, and sends the detected and amplified different voltage signal and the one or more subwaveforms to display device 840.

Display device 840 receives the processed ECG waveform for each heartbeat and displays the processed ECG waveform for each heartbeat. The processed ECG waveform is called a saah ECG waveform, for example. As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record saah ECG waveforms, saah ECG data and conventional ECG waveforms and data. The memory device can be, but is not limited to, a volatile electronic memory, such as random access memory (RAM), a non-volatile electronic memory, such as electrically erasable programmable read-only memory (EEPROM or Flash memory), or a magnetic hard drive.

In various embodiments, the detected one or more subwaveforms include at least one subwaveform representing depolarization of the sinoatrial node (SAN), the atria (right atrium (RA) and left atrium (LA)), the atrioventricular node (AVN), the bundle of His (HIS), or the bundle branches (BB) of the beating heart.

In various embodiments, the display device 840 further displays the ECG waveform for comparison with the processed ECG waveform.

In various embodiments, signal processor 830 further calculates timing information about the one or more subwaveforms, timing information about the intervals between the one or more subwaveforms, and timing information about the one or more subwaveforms and their relation to the P, Q, R, S, T, U, and J waveforms of the ECG waveform for each heartbeat. Display device 840 further receives this timing information from signal processor 830. Display device 840 displays the timing information about the one or more subwaveforms, the timing information about the intervals between the one or more subwaveforms, and the timing information about the one or more subwaveforms and their relation to the P, Q, R, S, T, U, and J waveforms of the ECG waveform for each heartbeat.

In various embodiments, the ECG system further includes a memory device (not shown). The memory device receives the ECG waveform and the processed ECG waveform from the signal processor.

In various embodiments, the memory device further includes normally processed ECG waveform data. Normally processed ECG waveform data is stored on the memory device using signal processor 830 or a general-purpose processor (not shown). Signal processor 830 further compares the processed ECG waveform to the normally processed ECG waveform data and calculates a status condition based on the comparison. The status conditions are, for example, normal, suspicious, or abnormal.

In various embodiments, the ECG system includes a second display device (not shown) surrounding a rotating button (not shown). Signal processor 830 further sends a colored pattern to the second display device based on the status condition. The second display device provides automatic pattern recognition diagnosis (APD).

Method for Detecting ECG Subwaveforms

Figure 16:
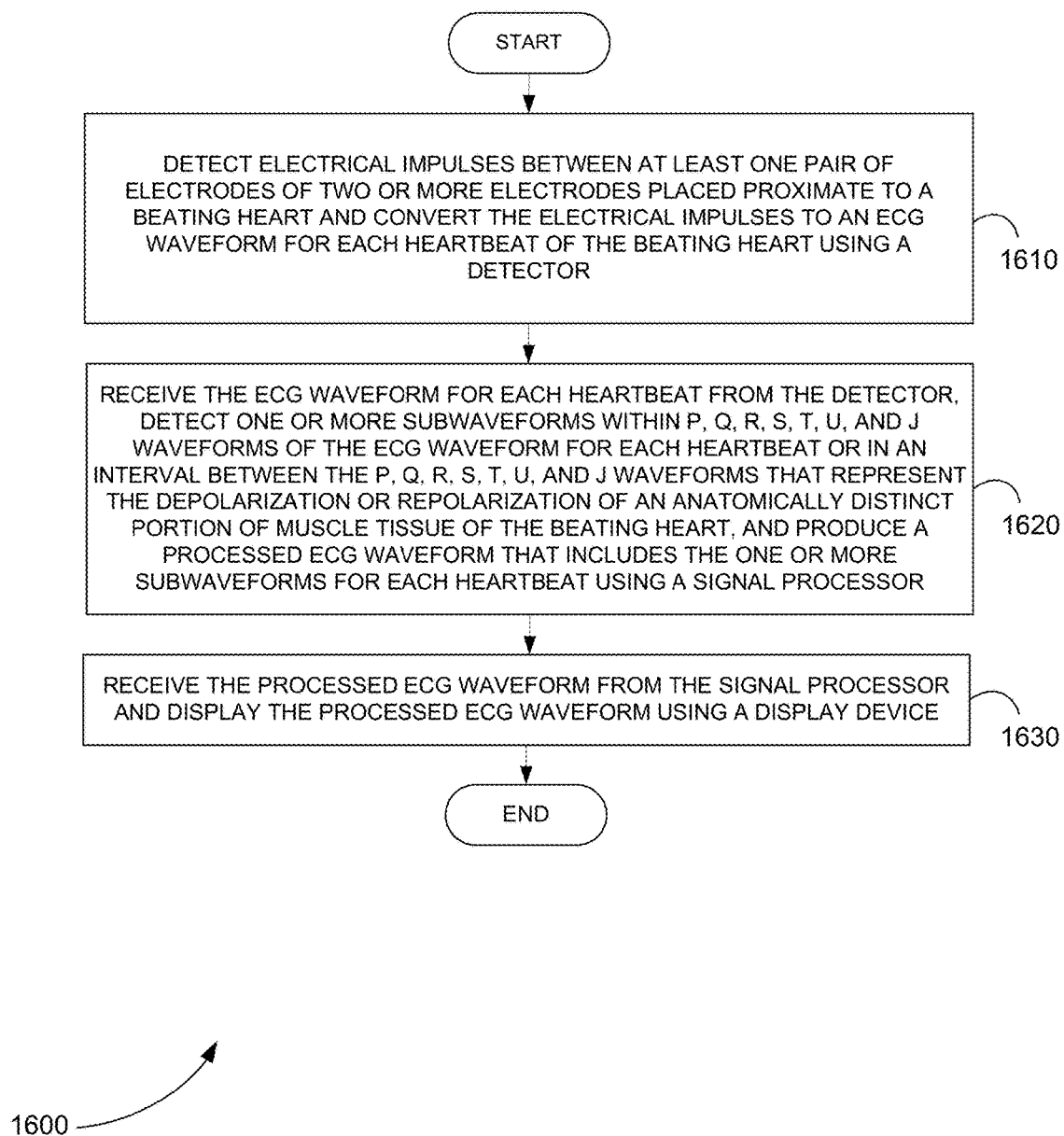
FIG. 16 is a flowchart showing a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 16 is a flowchart showing a method 1600 for detecting subwaveforms within the P, Q, R, S, T, U, and J waveforms of an ECG waveform of a heartbeat or in an interval between the P, Q, R, S, T, U, and J waveforms, in accordance with various embodiments.

In step 1610 of method 1600, electrical impulses are detected between at least one pair of electrodes of two or more electrodes placed proximate to a beating heart using a detector. The electrical impulses are converted to an ECG waveform for each heartbeat of the beating heart using the detector.

In step 1620, the ECG waveform for each heartbeat is received from the detector using a signal processor. One or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart are detected using the signal processor. A processed ECG waveform that includes the one or more subwaveforms for each heartbeat is produced using the signal processor.

In step 1630, the processed ECG waveform is received from the signal processor and the processed ECG waveform is displayed using a display device.

Computer Program Product for Detecting ECG Subwaveforms

In various embodiments, computer program products include a tangible computer-readable storage medium whose contents include a program with instructions being executed on a processor so as to perform a method for detecting subwaveforms within the P, Q, R, S, T, U, and J waveforms of an ECG waveform of a heartbeat or in an interval between the P, Q, R, S, T, U, and J waveforms. This method is performed by a system that includes one or more distinct software modules.

Figure 17:
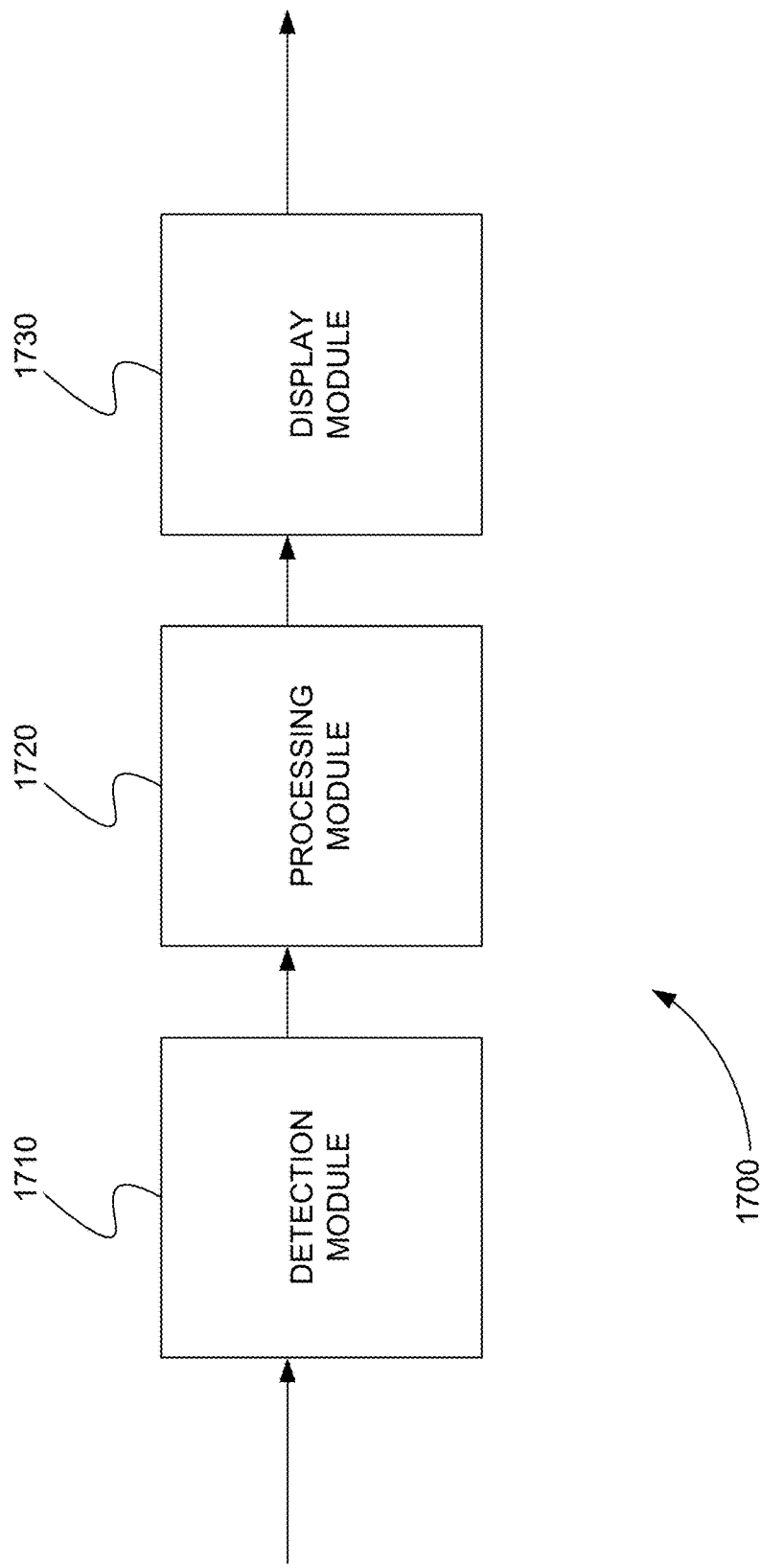
FIG. 17 is a schematic diagram of a system that includes one or more distinct software modules that perform a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 17 is a schematic diagram of a system 1700 that includes one or more distinct software modules that perform a method for detecting subwaveforms within the P, Q, R, S, T, U, and J waveforms of an ECG waveform of a heartbeat or in an interval between the P, Q, R, S, T, U, and J waveforms, in accordance with various embodiments. System 1700 includes detection module 1710, processing module 1720, and display module 1730.

Detection module 1710 detects electrical impulses between at least one pair of electrodes of two or more electrodes placed proximate to a beating heart. Detection module 1710 converts the electrical impulses to an ECG waveform for each heartbeat of the beating heart.

Processing module 1720 receives the ECG waveform for each heartbeat. Processing module 1720 detects one or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart. Processing module 1720 produces a processed ECG waveform that includes the one or more subwaveforms for each heartbeat.

Display module 1730 receives the processed ECG waveform. Display module 1730 displays the processed ECG waveform.

Multi-Domain ECG

The heart muscle, like other muscles, is activated by biologically generated electrical signals. Electrocardiography (ECG or EKG) has long been used to measure and record these electrical signals. Essentially, in ECG the electrical activity of the heart is measured from a number of different points on the body and plotted over time. As a result, ECG traces out each cardiac cycle or heartbeat as a voltage versus time waveform.

A human heart has two functional systems. The first system, referred to as a self-conduction system, is part of the atrium (including left and right atria). In a traditional ECG, the self-conduction system is represented by the P wave or PR interval. The excitation, rhythm, and conduction of every beat are completed by the collaboration of all parts of the heart, which is an axis system, including: sinoatrial node (SAN)—atrial—atrioventricular node (AVN)—Bundle of His—Bundle Branches (left and right). The Bundle of His is a collection of heart muscle cells specialized for electrical conduction that transmits the electrical impulses from the AVN to the point of the apex of the fascicular branches. Complex arrhythmias disease typically occurs in these different areas. However, ECG is only half of a sine wave.

The second system, referred to as a cardiac work system, is a pump system (one for each complete contraction and relaxation of the heart), which is done by the heart muscles. The main part of the second system is the left ventricle. In the traditional ECG, it is represented by the T wave or QT interval. There are about 10 million ventricular myocardial cells, without nerves or tracts.

Features or waves of each heartbeat waveform have been known for more than a century to correspond to electrical signals activating various parts of the heart. For example, the P wave is known to result from an electrical signal directed from the SAN to the AV node activating the atrium of the heart, to the Bundle of His to the left and tight Bundle Branches, and the T wave is known to result from a recovery electrical signal (ventricular depolarization and repolarization) sent to the ventricles of the heart after they have contracted. As a result, physicians are able to diagnose specific heart problems by analyzing the shapes and time of these waves.

It is thought that an ECG heartbeat waveform includes much more information about the anatomy of the heart that is not being used (scanning and displaying). In particular, it is thought that at least some of the waves in an ECG heartbeat waveform include subwaveforms that provide more detailed information about parts of the heart, as described above. Consequently, there is a need for systems and methods for processing biological electrical signals, such as signals read by ECG, in order to provide additional information about anatomical structures.

Also, electrocardiogram information itself contains a lot of information that has not been discovered so far, leaving numerous puzzles in a clinical application.

In various embodiments, new waveforms are created from a conventional ECG waveform. New indexes and new parameters are obtained from the new waveforms, so that it is possible to have a breakthrough in electrocardiogram diagnostics.

In various embodiments, heart signals are divided into different frequency bands, and then convolved or combined in one diagram. For example, 16 different frequency bands can be used. This procedure is based on the study of ergonomics and analysis procedures for frequently used information in cybernetics and nonlinear theory. The procedure makes use of the theory and analysis index of an "electrocardiogram multi-phase signal," and by using a new method of frequency division and dimension division, according to the display method of P, Q, R, S, T, U, and J waveforms P-QRS-T in a conventional ECG waveform. Heart diseases are also related to and/or complicated by different other diseases. Therefore, different numbers of frequency ranges are required to be displayed as a diagnostic requirement, because the frequency shifts of various diseases are different. In the multi-domain frequency division method, 8, 9, 10, 11, 12, 13, 14, 15, or 16 roots of multi-domain linear waveforms are displayed, and a total of 12 leads are individually displayed. If each lead is divided into 16 waveforms, there are totally 192 ECG waveforms, providing much more information. In various embodiments, multi-domain ECG (mdECG) can be used as a very valuable and new diagnostic technique for combined heart diseases. This technique can be applied in electrocardiograph, monitor, echocardiography, and invasive electrophysiological instrument.

Since the invention of ECG, the linear waveform shaped like a rope has been used. Its frequency response range is 0-150 Hz and all subwaveforms are convolved or combined together. However, heart signals are formed by combining different ultra-low frequency, low frequency, intermediate frequency, high frequency, and ultrAHigh frequency signals. Because in ECG all frequencies are convolved together, many fine, weak, and very valuable signals are usually submerged or overlapped by the high frequency; especially at ventricle (ECG at T-wave, ECG 'T' wave duration) and atrium (ECG at P-wave, ECG 'P' wave duration), and numerous signals accumulate within a very small time axis range, causing problems and confusion in the accuracy of the ECG diagnosis rate. As a result, the detection rate of ECG for acute myocardial infarction (AMI), acute coronary syndrome (ACS), coronary artery disease (CAD), myocardial infarction (MI), heart failure (HF), etc., with the highest incidence of cardiovascular disease is only 17%-25%. Based on a large number of research reports, for the CAD/MI/ACS patient, ECG begins to change only after ischemia reaches 70%, and only about half of the electrocardiograms show abnormality. There are 7 billion people in the world, and the percentage of people who die of cardiovascular diseases or complicated cardiovascular diseases is about 42.86% (3/7). An electrocardiogram is the most fundamental clinical assessment instrument, and it is simple, fast and economical.

Therefore, it is important to improve the clinical ECG diagnosis rate, which is possible only by improving the waveform display rate of ECG.

In various embodiments, systems and methods improve the waveform display rate of ECG and clinical diagnosis rate using a 16 linear multi-domain electrocardiogram. Because the heart signals are separated according to different frequency bands with frequency bands being recombined, many high frequency signals, ultrAHigh frequency signal, low frequency signals, and ultra-low frequency signals are displayed with the raw heart signals at different frequency band according to the heart transduction pathway and electrophysiological rule, without the electrocardiogram being altered, i.e., at X-transverse axis and Y-vertical axis of P-QRS-T. Because the frequency bands of ECG are combined signals, mdECG separates the signals, i.e., separates them into independent waveforms consisting of different frequency bands. In this way, those frequency bands with the one linear waveform invisible and obscure in traditional ECG can be displayed clearly with different frequency bands one by one, assisting the doctor in reading, analyzing, judging and basic clinical assessment.

Figure 18:
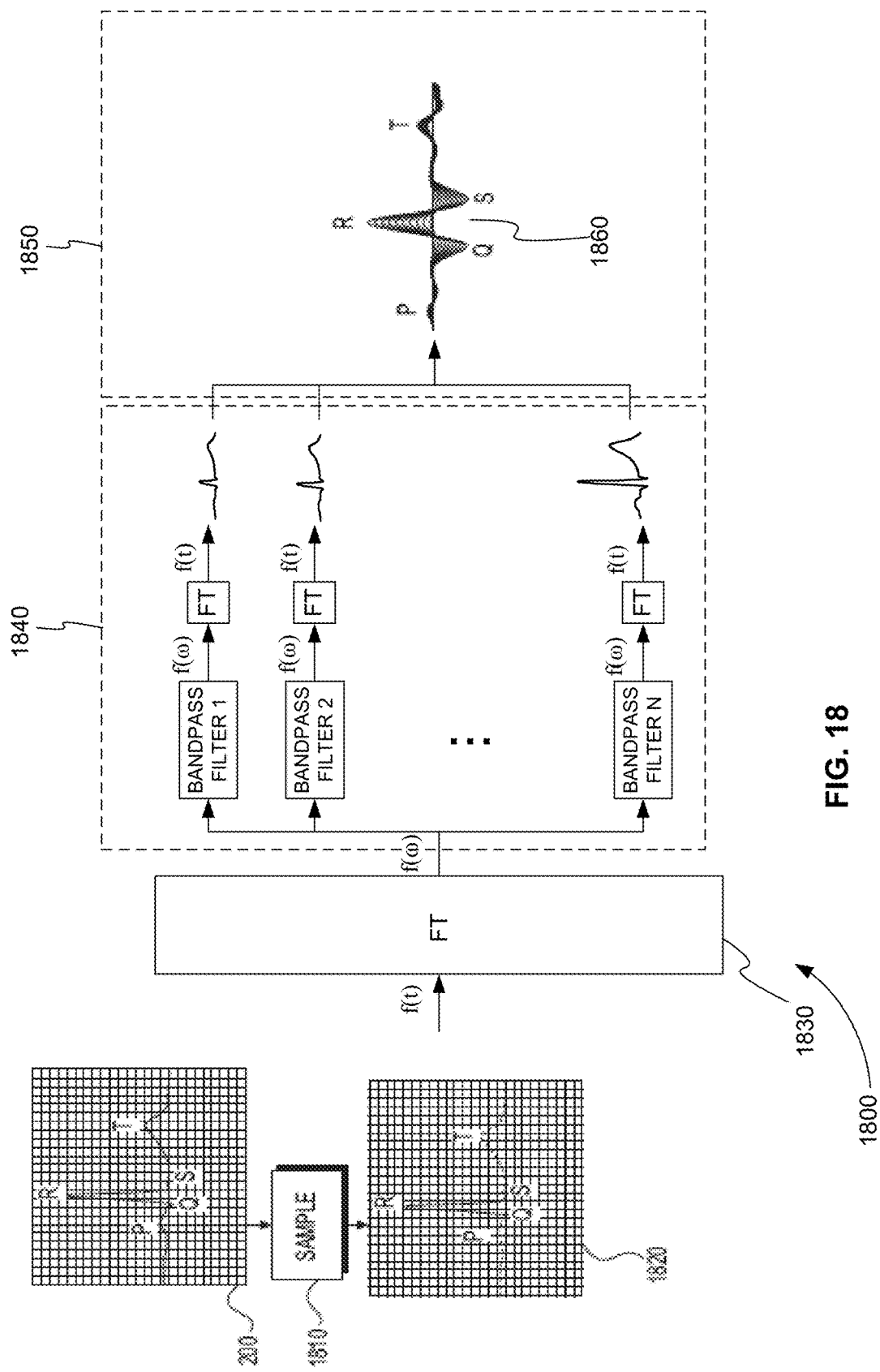
FIG. 18 is an exemplary block diagram showing a system for performing multi-domain ECG using 16 different frequency bands or domains, in accordance with various embodiments.

FIG. 18 is an exemplary block diagram 1800 showing a system for performing multi-domain ECG using 16 different frequency bands or domains, in accordance with various embodiments. Sampling block 1810 samples the electrical impulses at one electrode for one heartbeat, for example. This is shown graphically in FIG. 18 by converting ECG waveform 200 to sampled ECG waveform 1820 using block 1810. The electrical impulses for the entire ECG waveform 200 are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 18, block 1830 converts sampled ECG waveform 1820 to a frequency domain signal. The time domain signal is converted into a frequency domain signal using a Fourier transform, for example.

As described above, through animal and/or human experimentation, the frequency bands associated with different muscles of the heart can be determined. The frequency bands used here can be based on those bands determined experimentally, for example. Alternatively, the 16 frequency bands can be found by dividing the total frequency bands 16 ways. The different band can have the same bandwidth or can have different bandwidths.

In block 1840, 16 different band pass filters filter sampled ECG waveform 1820's frequency domain signal into 16 different frequency domain signal. These 16 different 16 different frequency domain signals are then converted back to the time domain. The result of block 1840 is 16 different time domain signals.

In block 1850, the 16 different time domain signals are combined or plotted together in the time domain as one multi-domain ECG waveform 1860. In FIG. 18, a conventional ECG signal from one electrode is processed into a multi-domain ECG waveform that includes 16 different time domain signals. In various embodiments, a conventional ECG signal from one electrode, however, can be processed into a multi-domain ECG waveform that includes any number of different time domain signals.

Figure 19:
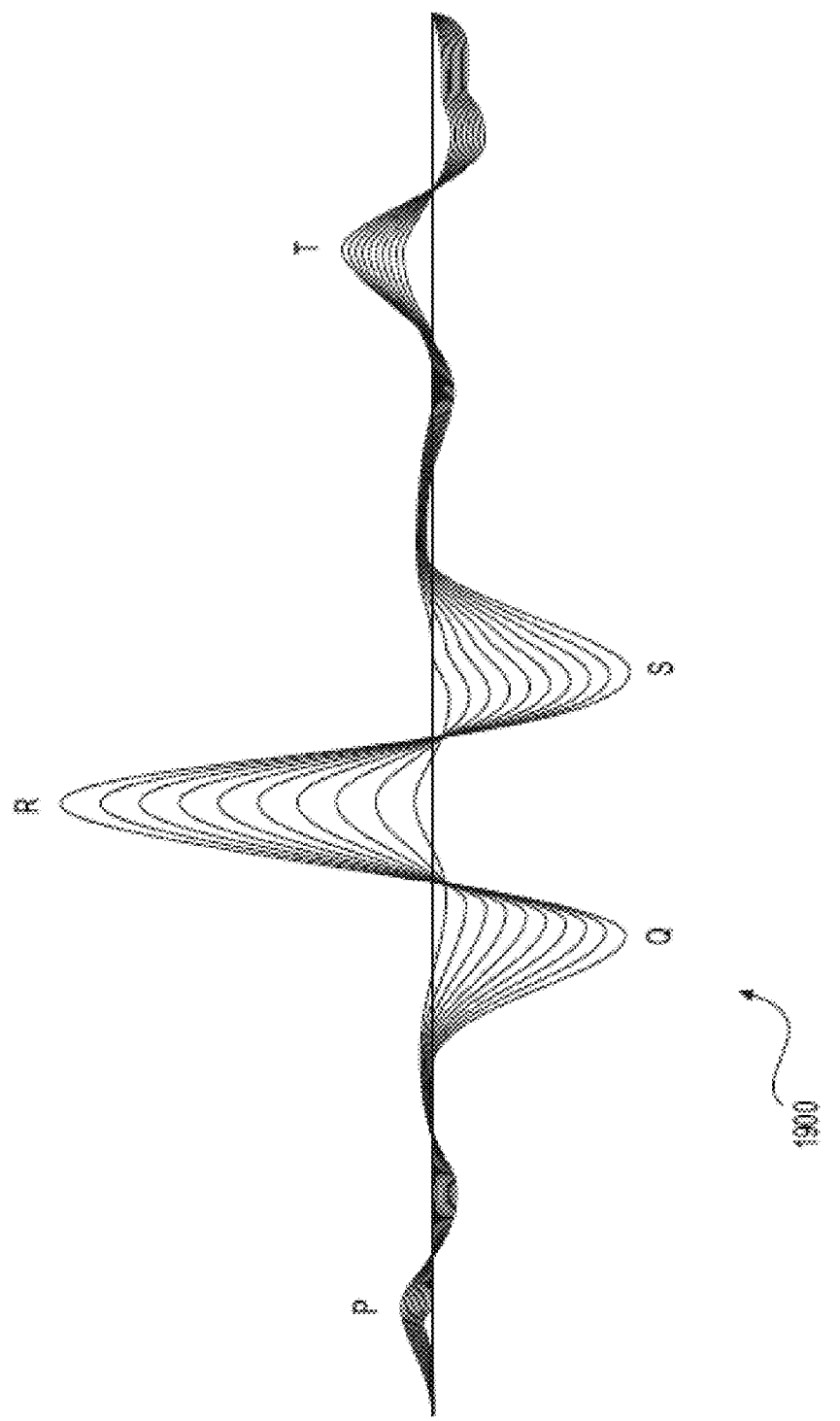
FIG. 19 is an exemplary plot of a multi-domain ECG waveform that includes 10 different time domain signals, in accordance with various embodiments.

FIG. 19 is an exemplary plot 1900 of a multi-domain ECG waveform that includes 10 different time domain signals, in accordance with various embodiments.

Figure 20:
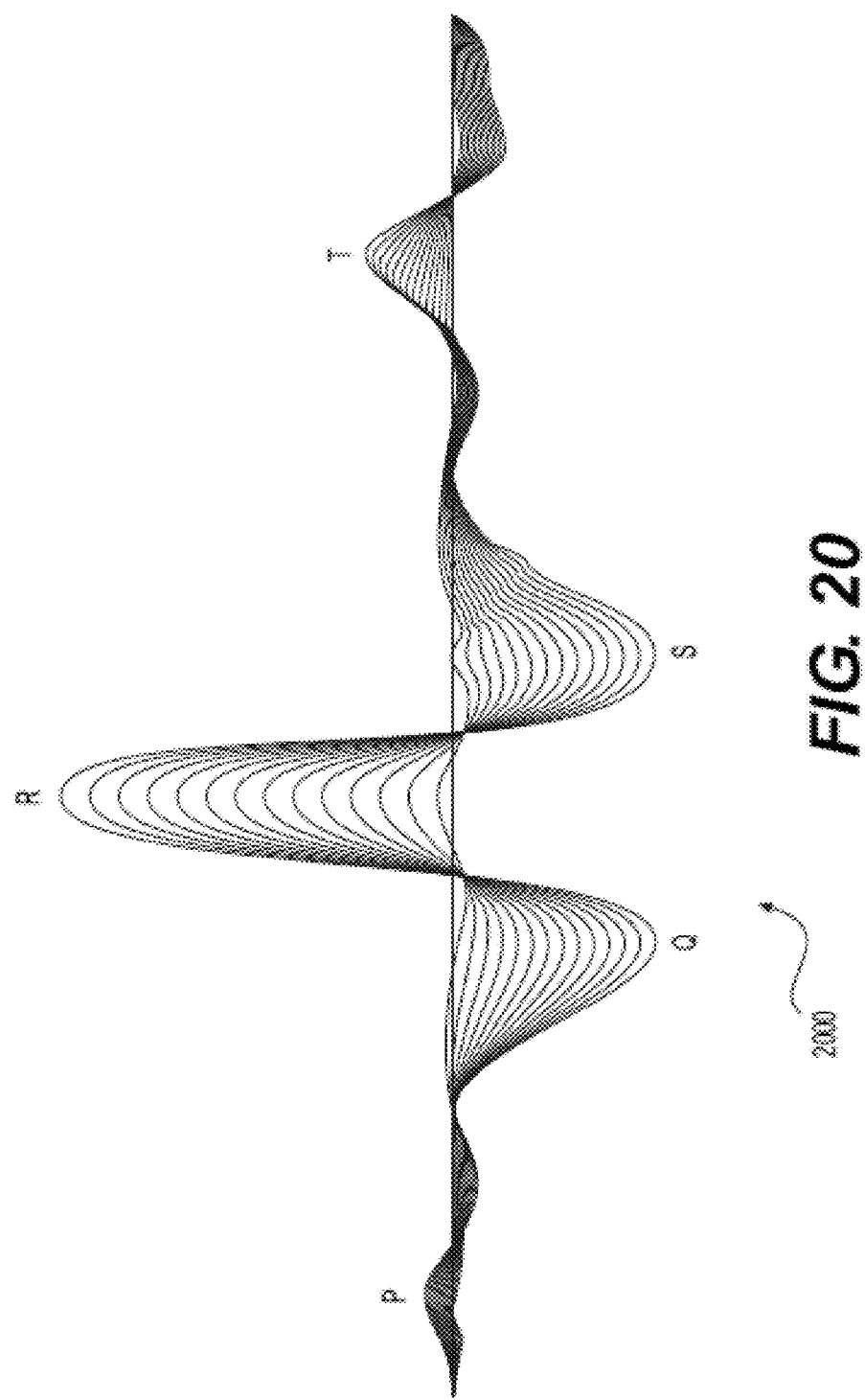
FIG. 20 is an exemplary plot of a multi-domain ECG waveform that includes 14 different time domain signals, in accordance with various embodiments.

FIG. 20 is an exemplary plot 2000 of a multi-domain ECG waveform that includes 14 different time domain signals, in accordance with various embodiments.

Figure 21:
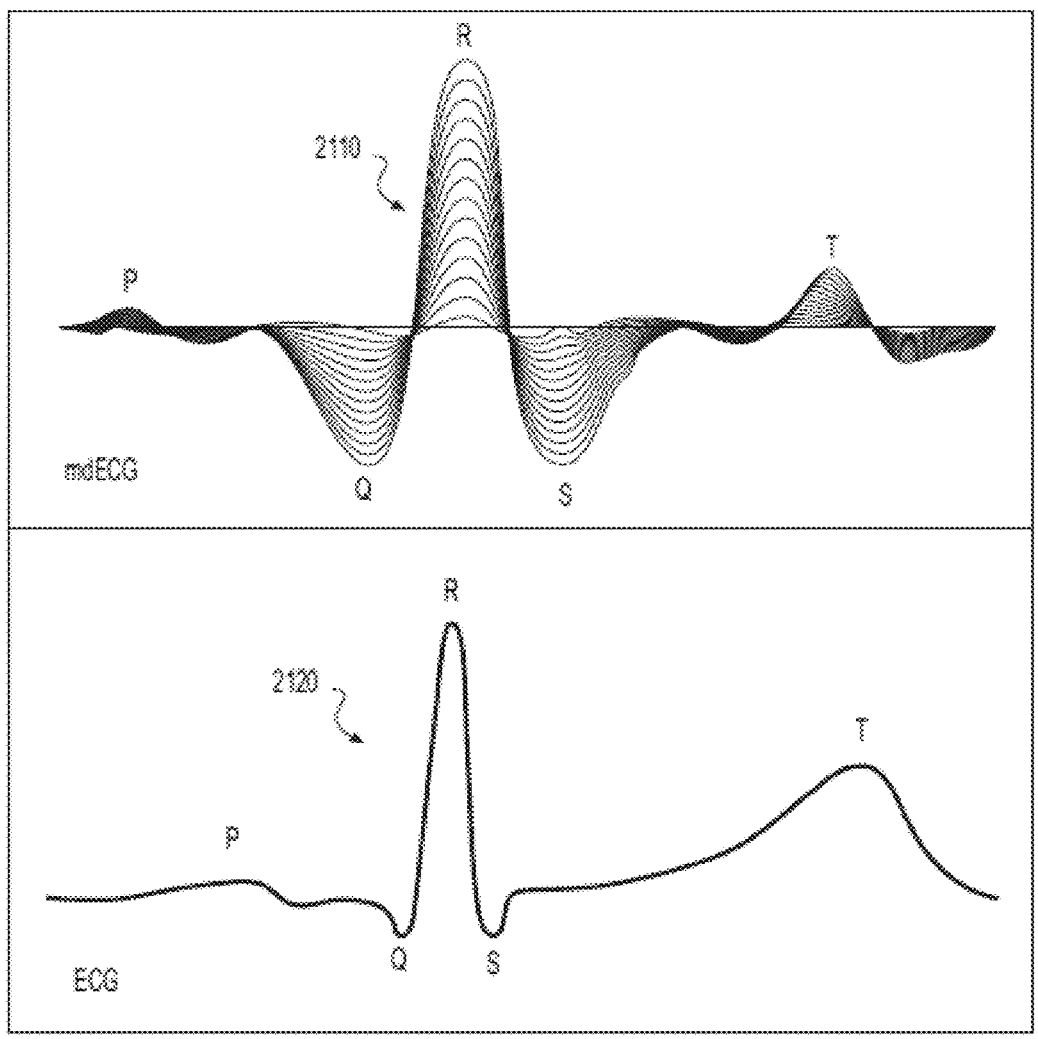
FIG. 21 is an exemplary alignment of a multi-domain ECG waveform that includes 16 different time domain signals with a conventional ECG waveform, in accordance with various embodiments.

FIG. 21 is an exemplary alignment 2100 of a multi-domain ECG waveform 2110 that includes 16 different time domain signals with a conventional ECG waveform 2120, in accordance with various embodiments. Multi-domain ECG waveform 2110 is produced from conventional ECG waveform 2120 using the system depicted in FIG. 18, for example. As shown in FIG. 21, multi-domain ECG waveform 2110 can display data with negative values while conventional ECG waveform 2120 cannot.

Systems and methods for detecting multi-domain ECG waveforms are described in the '930 Patent, which is incorporated by reference in its entirety.

Example Saah ECG Waveforms and EPCG Waveforms

Figure 29:
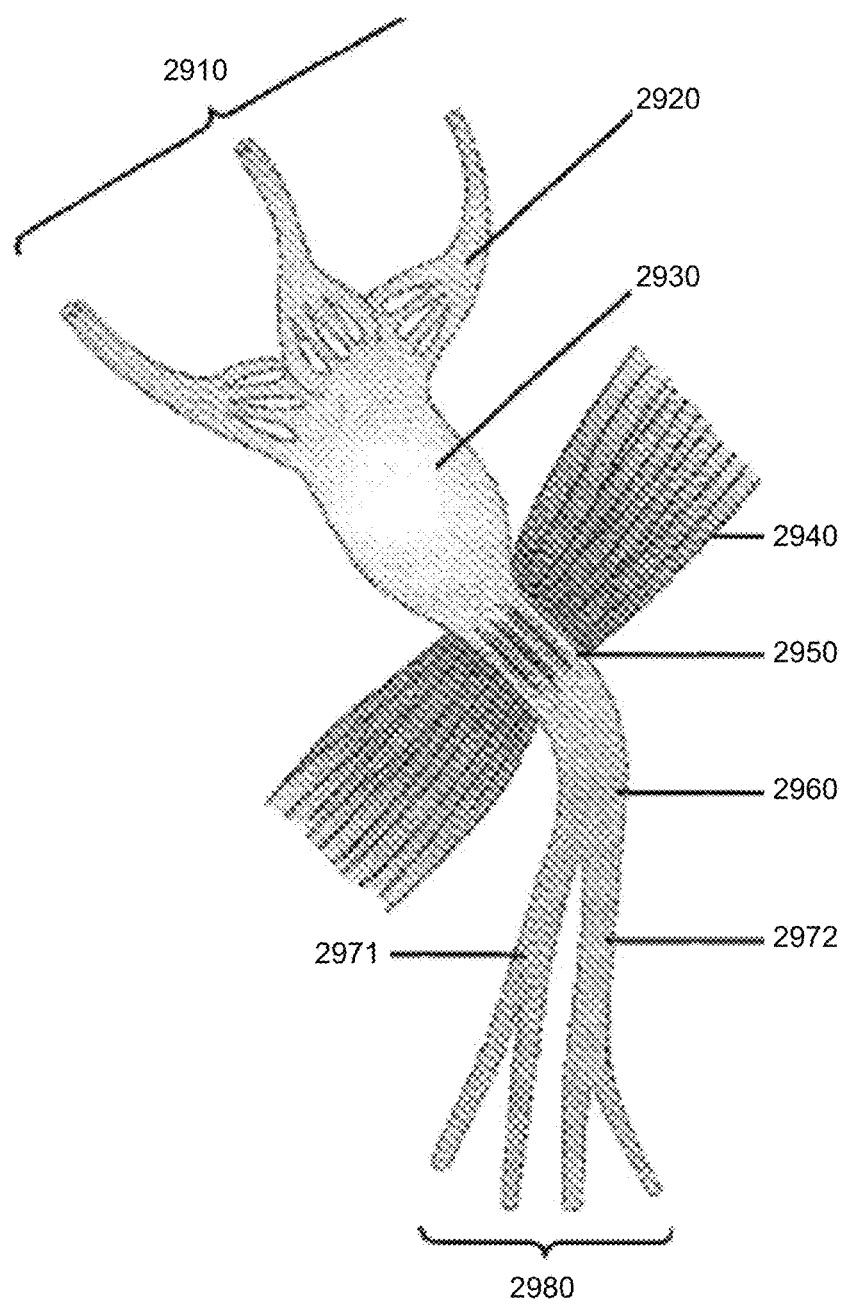
FIG. 29 is an exemplary diagram of the anatomy of the self-conducting system of a heart, in accordance with various embodiments.

FIG. 29 is an exemplary diagram 2900 of the anatomy of the self-conducting system of a heart, in accordance with various embodiments. The self-conducting system begins with S-A node (SAN) 2910. Conduction moves from SAN 2910 through transitional fibers 2920 to A-V node (AVN) 2930. Conduction then moves from AVN 2930 past atrioventricular fibrous tissue 2940 and through penetrating portion of A-V bundle (His bundle) 2950 to distal portion of A-V bundle 2960. From distal portion of A-V bundle 2960 conduction moves through right bundle branch 2971 and left bundle branch 2972 to ventricular septum 2960.

Figure 30:
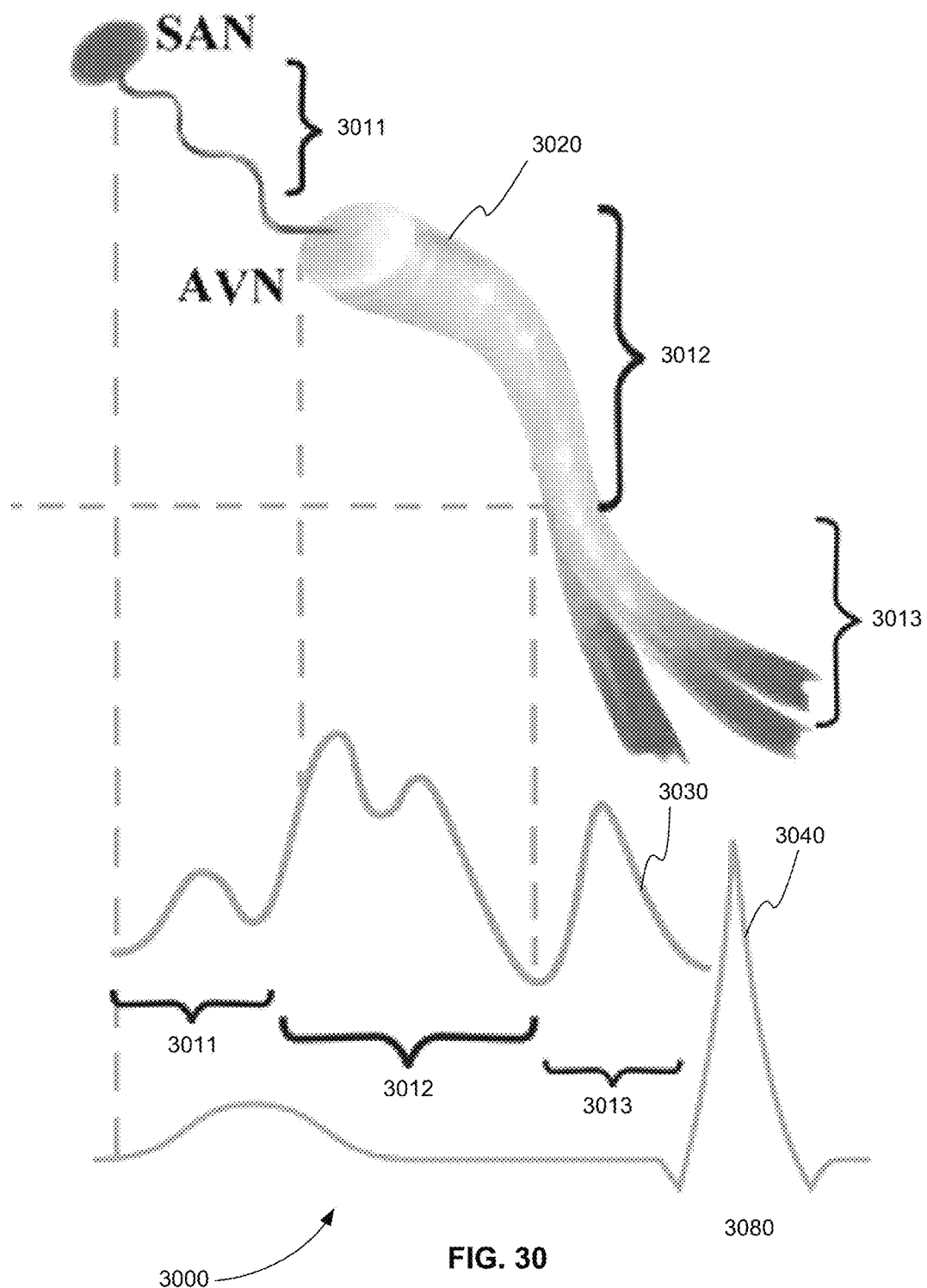
FIG. 30 is an exemplary diagram showing the anatomic sites that the PA, AH, and HV intervals represent and the corresponding PA, AH, and HV intervals in a saah ECG waveform and traditional ECG waveform, in accordance with various embodiments.

FIG. 30 is an exemplary diagram 3000 showing the anatomic sites that the PA, AH, and HV intervals represent and the corresponding PA, AH, and HV intervals in a saah ECG waveform and traditional ECG waveform, in accordance with various embodiments. PA interval 3011, AH interval 3012, and HV interval 3013 are depicted with respect to anatomic sites along self-conducting system 3020 of the heart. The same intervals, PA interval 3011, AH interval 3012, and HV interval 3013, are also shown with respect to saah ECG waveform 3030 and traditional ECG waveform 3040. FIG. 30 shows that processed or calculated information like PA interval 3011, AH interval 3012, HV interval 3013, and saah ECG waveform 3030 relate ECG signals more closely to the anatomy of self-conducting system 3020 than traditional ECG waveform 3040.

Figure 31:
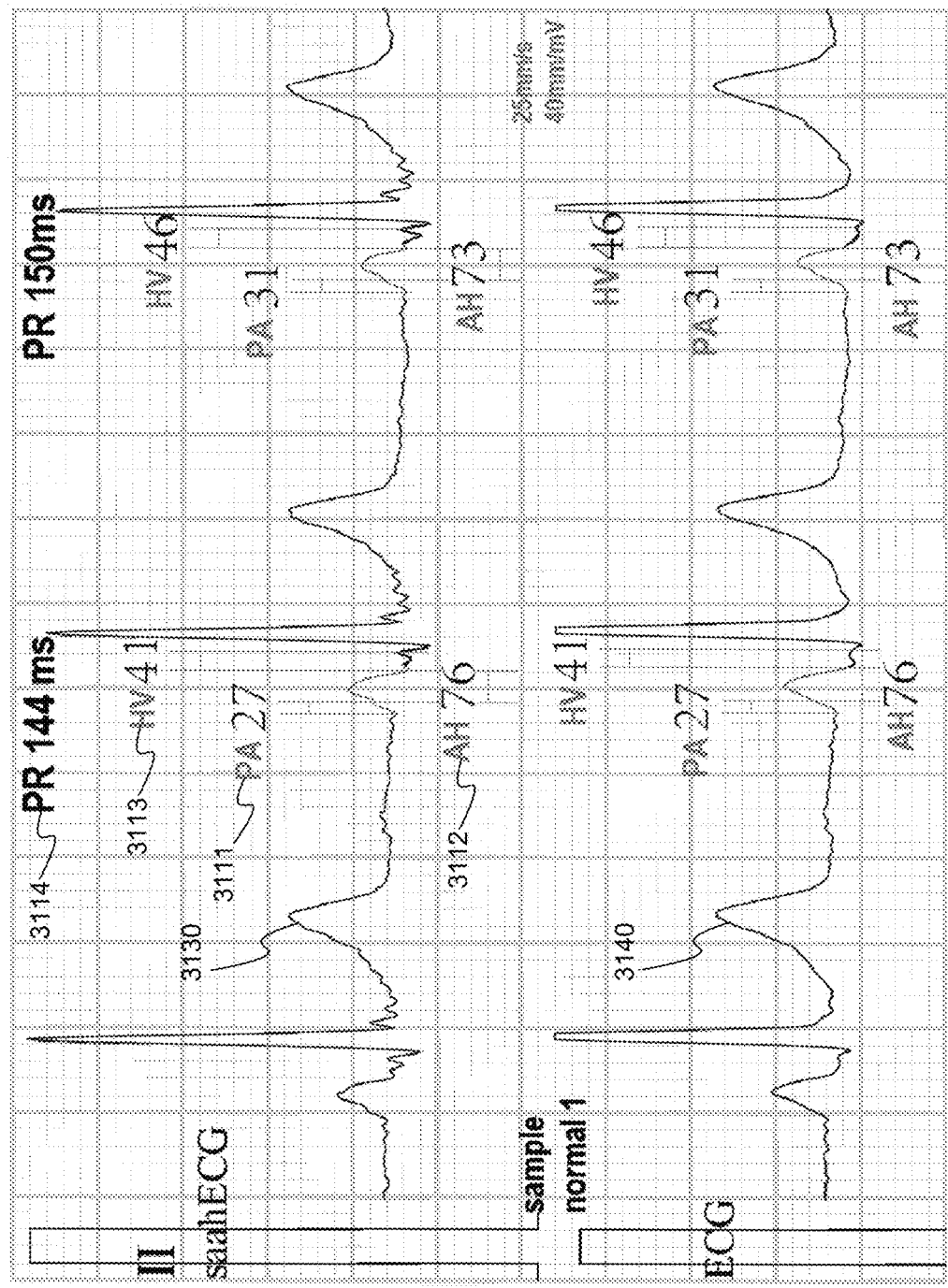
FIG. 31 is an exemplary comparison plot of a saah ECG waveform and a traditional ECG waveform with PA, AH, HV, and PR interval values obtained from aiECG processing for a patient with a normal heart, in accordance with various embodiments.

FIG. 31 is an exemplary comparison plot 3100 of a saah ECG waveform and a traditional ECG waveform with PA, AH, HV, and PR interval values obtained from aiECG processing for a patient with a normal heart, in accordance with various embodiments. Timing values for PA interval 3111, AH interval 3112, HV interval 3113 and PR interval 3114 are shown with respect to saah ECG waveform 3130 and aligned traditional ECG waveform 3140. As described above, PR interval 3114 refers to the time period that includes the P waveform and the PR segment of traditional ECG waveform 3140. FIG. 31 shows that processed or calculated information like the timing values for PA interval 3111, AH interval 3112, HV interval 3113, and PR interval 3113 and saah ECG waveform 3130 provide much more information than traditional ECG waveform 3140 on its own.

Figure 32:
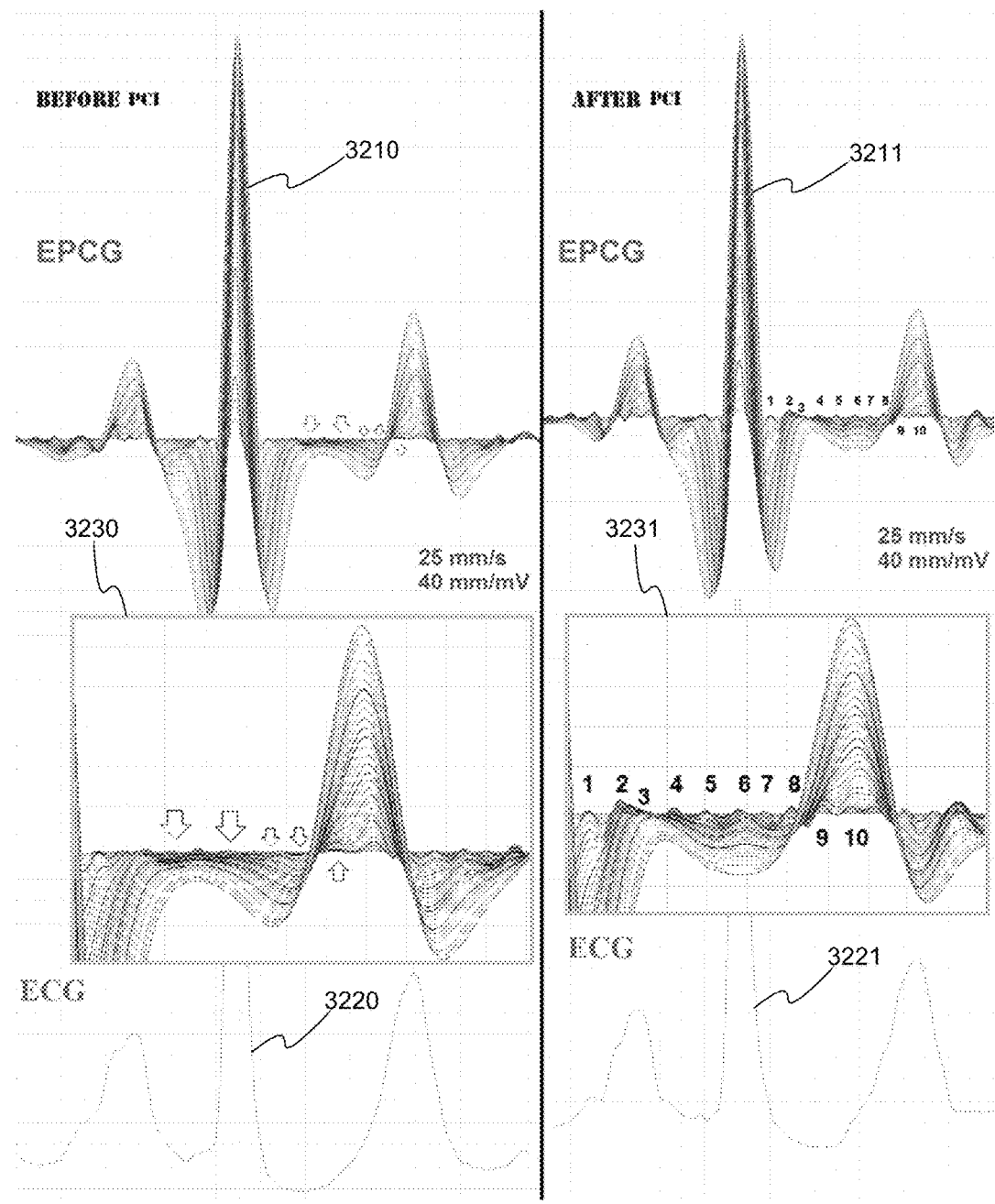
FIG. 32 is an exemplary comparison plot of a multi-domain ECG or electrophysiocardiogram (EPCG) waveform aligned with a traditional ECG waveform for a patient with acute coronary syndrome (ACS) before and after percutaneous coronary intervention (PCI), in accordance with various embodiments.

FIG. 32 is an exemplary comparison plot 3200 of a portion of a multi-domain ECG or electrophysiocardiogram (EPCG) waveform aligned with a portion of a traditional ECG waveforms for a patient with acute coronary syndrome (ACS) before and after percutaneous coronary intervention (PCI), in accordance with various embodiments. EPCG waveform 3210 is aligned with traditional ECG waveform 3220 for the patient with ACS before PCI treatment. EPCG waveform 3211 is aligned with traditional ECG waveform 3221 for the patient with ACS after PCI treatment. A comparison of magnified portions 3230 and 3231 of EPCG waveforms 3211 and 3211, respectively, shows that all small waveforms are not apparent in waveform portion 3210 before PCI treatment are back to normal after PCI treatment in waveform portion 3211. Similar information cannot be found in a comparison of traditional ECG waveforms 3220 and 3221.

Figure 33:
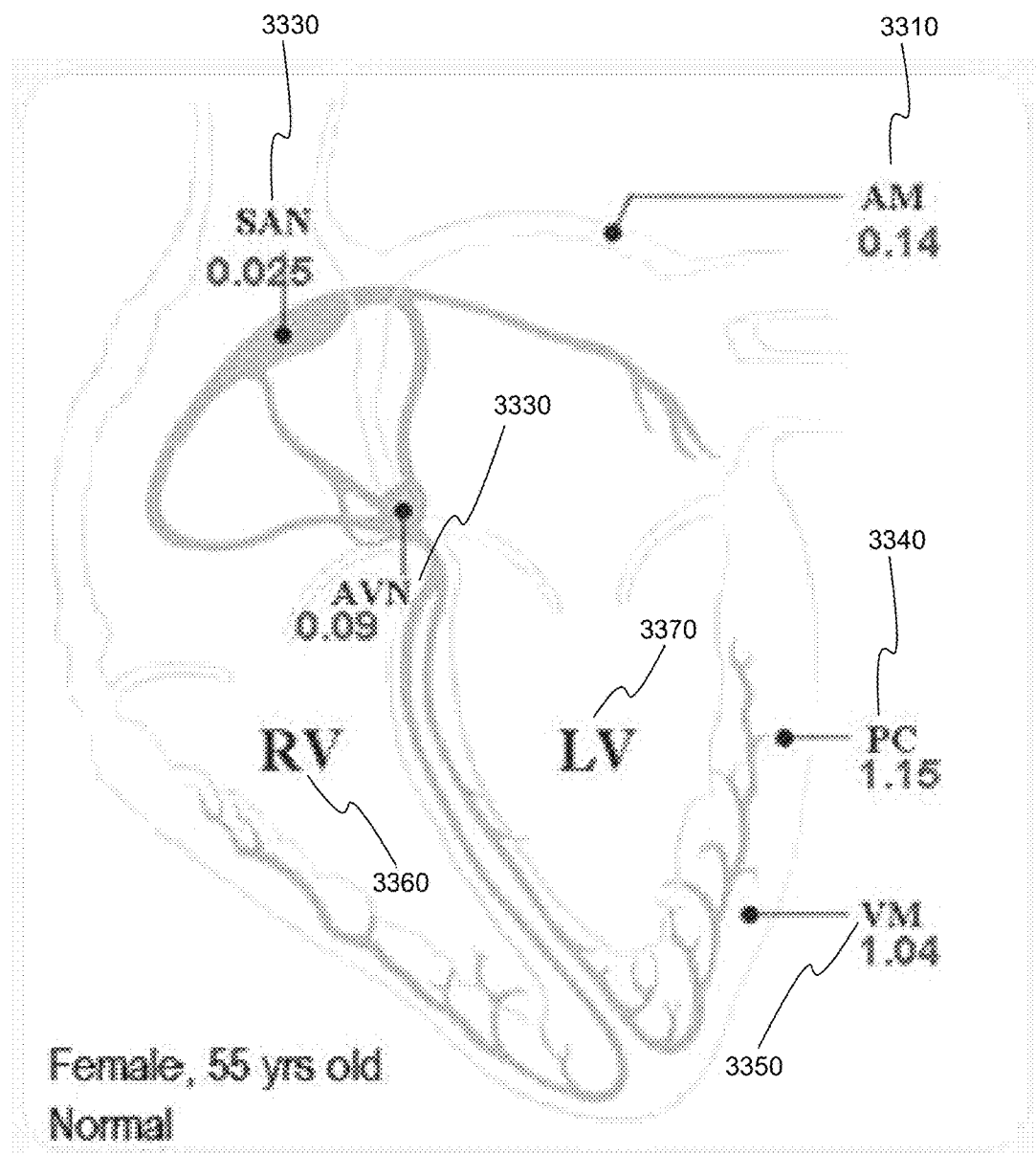
FIG. 33 is an exemplary diagram showing timing values of conduction calculated at various anatomic sites along the self-conduction system of a normal heart by further processing a traditional ECG waveform, in accordance with various embodiments.

FIG. 33 is an exemplary diagram 3300 showing timing values of conduction calculated at various anatomic sites along the self-conduction system of a normal heart by further processing a traditional ECG waveform, in accordance with various embodiments. For example, timing values are provided for the atrial myocardium (AM) 3310, the sino atrial node (SAN) 3320, the atrioventricular node (AVN) 3330, Purkinje's cell (PC) 3340, and the ventricular myocardium (VM) 3350. The right ventricle (RV) 3360 and the left ventricle (LV) 3370 are also labeled in diagram 3300.

Automated ECG Analysis and Diagnosis

As described above, to date the accuracy rate of automated ECG analysis and diagnosis systems has been a problem in clinical applications. There are at least three technical reasons for this. 1. The conventional ECG waveform is morphological and generally no consistent mapping points can be found. 2. Conventional ECG measurements have not provided information specific different parts of the heart muscle. 3. Automated ECG waveform analysis has generally resulted in a high number of false positives for both normal and abnormal populations. However, ECG remains one of the most extensively used clinical tools, despite the lack of accurate systems for automated ECG analysis and diagnosis. As a result, there is a significant need for such systems. Recent advancements have addressed the conventional ECG waveform measurement problem. Specifically, the systems of the '204 Patent and the '930 Patent have allowed the different frequency domain signals from different parts of the heart muscle to be measured.

Additional systems, however, are needed to further address the technical problems of analyzing the shape and form of these frequency domain signals and distinguishing disease conditions from false positives in normal and abnormal populations.

Conventional ECG Waveform Analysis Problems

Analysis of conventional ECG waveforms for clinical diagnosis has been limited by a number of problems for more than a century. (1) It has been difficult to correctly confirm the start point of the P wave. The reason for this is that the start point of the P wave is on "a parallel equipotential line," which needs to be determined. This has traditionally been determined through guessing. If the starting point of each heartbeat cannot be correctly identified, then all subsequent parameter measurements will be wrong. The normal value for the conduction time from the SA node (the starting point of the P wave) to the atrium is only around 30 ms. As a result, a small mistake in the location of the starting point can make a big difference in the measurement of this conduction time.

Figure 14:
FIG. 14 is an exemplary plot of a conventional ECG waveform showing how a small error in the starting point of the P wave can cause a large error in all subsequent time measurements, in accordance with various embodiments.

FIG. 14 is an exemplary plot 1400 of a conventional ECG waveform showing how a small error in the starting point of the P wave can cause a large error in all subsequent time measurements, in accordance with various embodiments. The starting point of P wave 1430 of conventional ECG waveform 1410 is somewhere on parallel equipotential line 1420. Each square of the grid of plot 1400 represents a time of 40 milliseconds (ms). Parallel equipotential line 1420 spans about one square of the grid of plot 1400. As a result, picking four different closely spaced points along parallel equipotential line 1420 produces starting point times that vary among 8 ms, 16 ms, 24 ms, and 32 ms within the one square of the grid of plot 1400. In other words, small differences in the selection of the starting point of P wave 1430 can mean large differences in the timing values used for P wave 1430. It can also affect all of the other components of ECG waveform 1410. This is because the starting point of P wave 1430 is also the starting point of the entire ECG waveform 1410.

(2) At the PR interval, it has been difficult to identify the specific PA, AH, or HV intervals within PR interval. When the PR interval is abnormal, in particular, it can only be estimated and cannot be measured. Also, often the end of the PR interval cannot be confirmed, as there is no equipotential and the starting point of QRS wave appears to be an upward arc angle.

Figure 15:
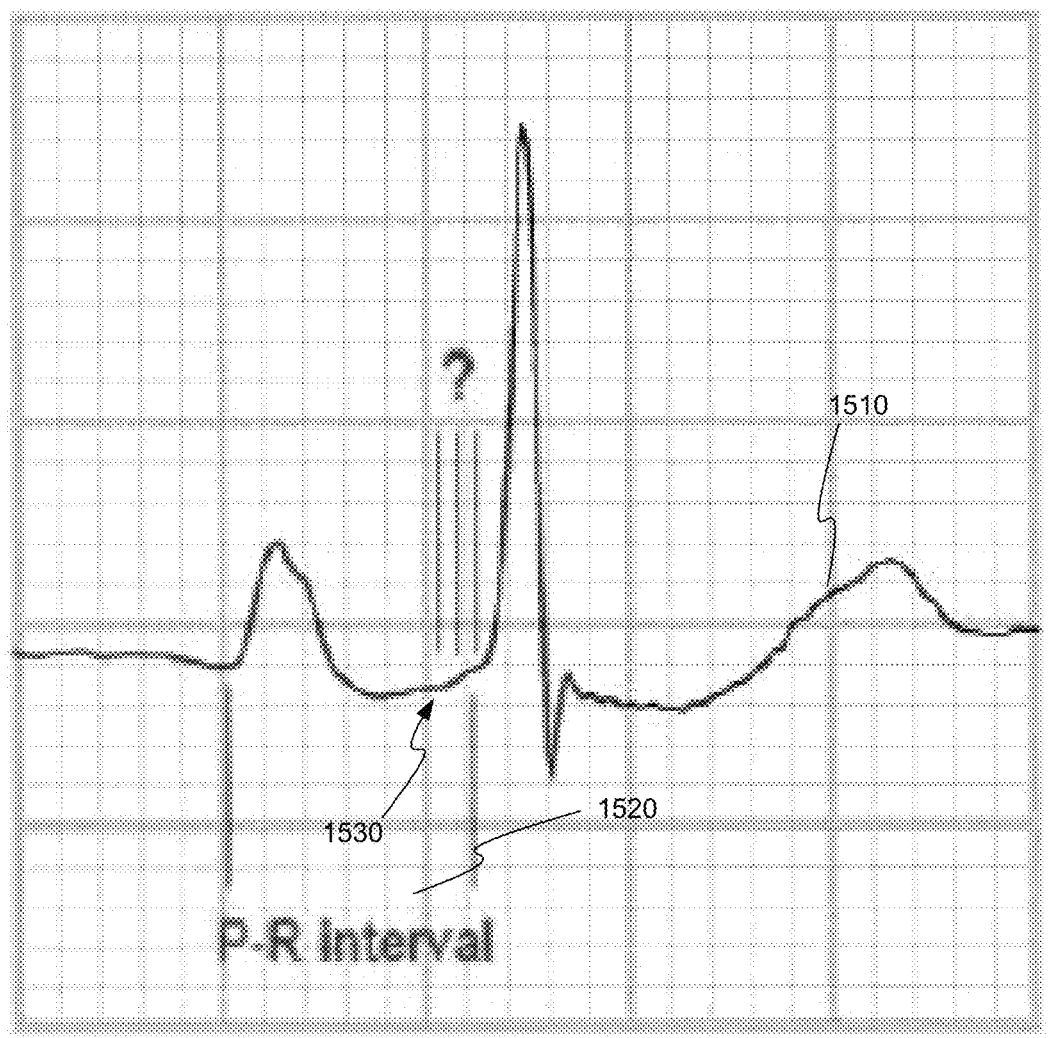
FIG. 15 is an exemplary plot of a conventional ECG waveform showing how the end of the PR interval cannot be confirmed due to an upward arc angle of the starting point of QRS wave, in accordance with various embodiments.

FIG. 15 is an exemplary plot 1500 of a conventional ECG waveform showing how the end of the PR interval cannot be confirmed due to an upward arc angle of the starting point of QRS wave, in accordance with various embodiments. The timing measurement of PR interval 1520 of conventional ECG waveform 1510 is a very important measurement since it the only measurement for the atrium. As described above, it is difficult to measure the starting point of the P wave, which is also the start of PR interval 1520. It turns out it is just as difficult if not more difficult to measure the ending point of PR interval 1520. This is due to changes to parallel equipotential line 1530 at the ending point of PR interval 1520 as shown in plot 1500. Parallel equipotential line 1530 is not parallel at all but rather is shaped like an upward arc angle. Therefore, it is very difficult to accurately map PR interval 1520. The standard value for PR interval 1520 is 120-200 ms, for example. In contrast, PR segment 220 of ideal conventional ECG waveform of FIG. 2 has a parallel equipotential line just before a downward arc angle to the QRS wave.

(3) It has been difficult to identify a difference between the ST segment of a normal person and the ST segment of an abnormal person. In other words, the ST segment appears to be exactly abnormal for normal people and exactly normal for abnormal people. Also, and the J point often disappears, making it impossible to determine. As a result, the standards for the ST segment often cannot be applied.

Figure 22:
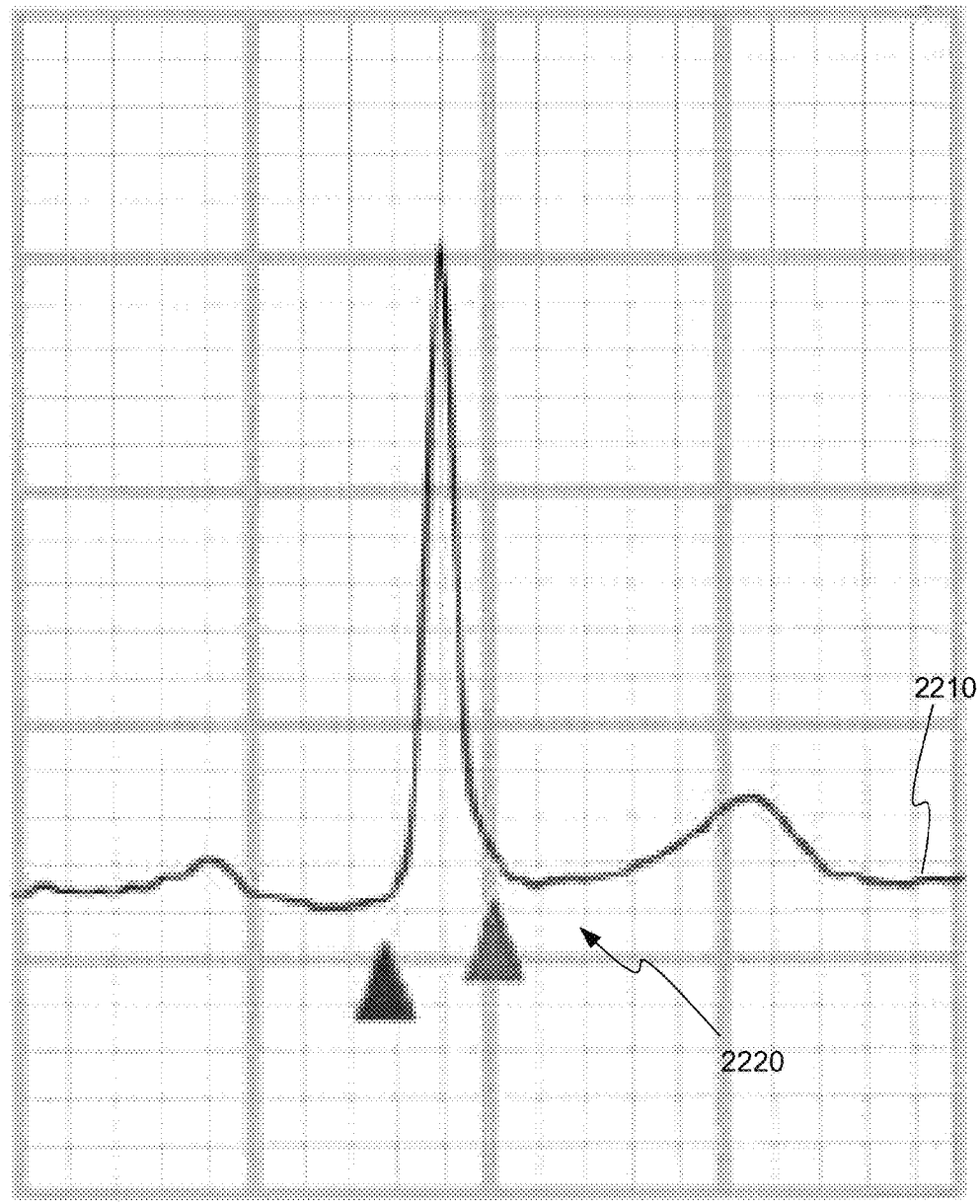
FIG. 22 is an exemplary plot of a conventional ECG waveform showing how the ST segment of a normal person can appear abnormal, in accordance with various embodiments.

FIG. 22 is an exemplary plot 2200 of a conventional ECG waveform showing how the ST segment of a normal person can appear abnormal, in accordance with various embodiments. Plot 2200 shows the conventional ECG waveform 2210 of a normal person. However, ST segment 2220 has lifted or arc shape. As a result, ST segment 2220 is difficult to measure. The normal morphological waveform is exactly like abnormal, while abnormal is exactly like normal.

(4) It has been difficult to identify the main peak of the T wave. Often it appears to be exactly abnormal (inverted) for normal people and exactly normal for abnormal people, making it almost impossible to determine.

Figure 23:
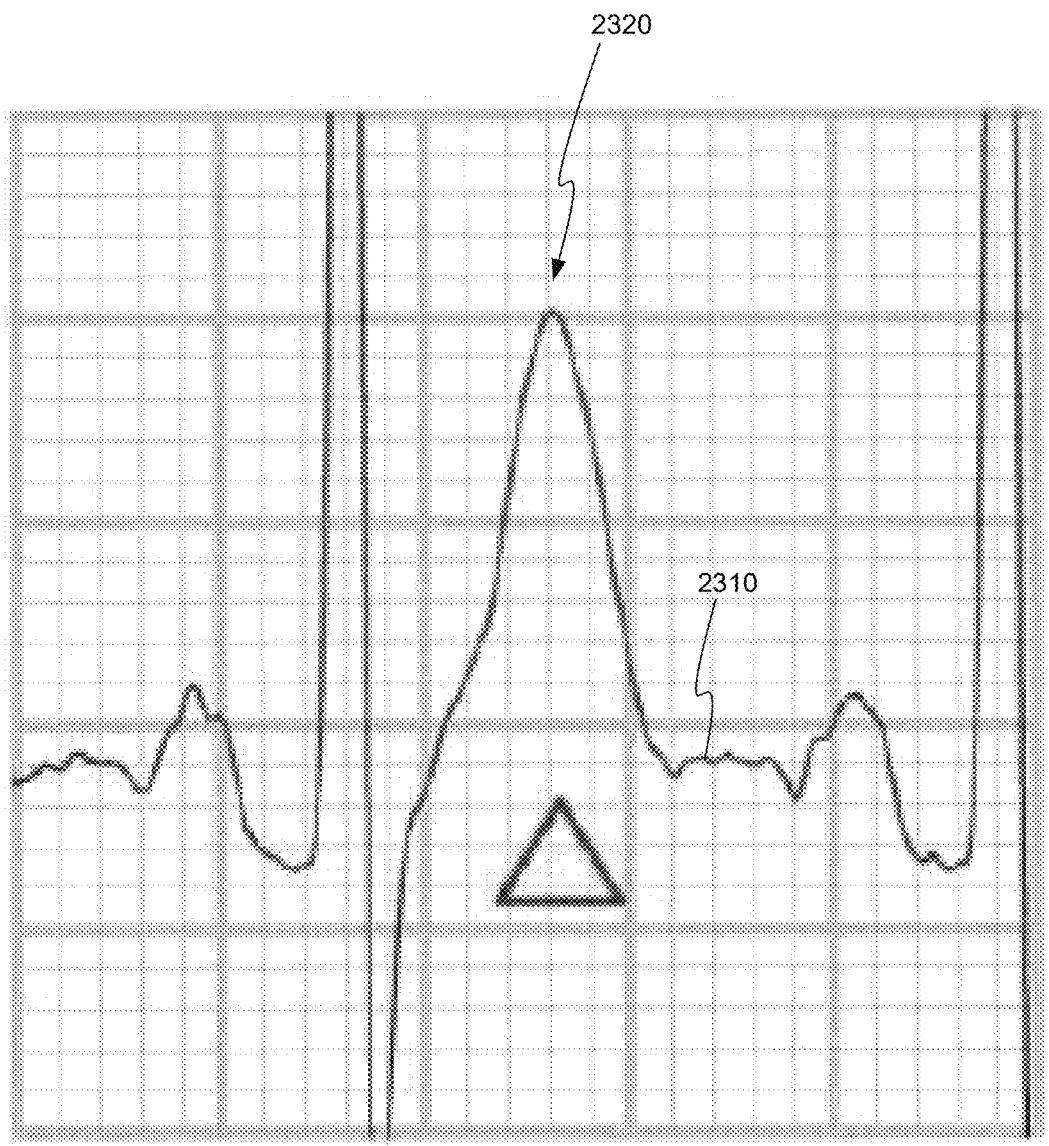
FIG. 23 is an exemplary plot of a conventional ECG waveform showing how the T wave of an abnormal person can appear normal, in accordance with various embodiments.

FIG. 23 is an exemplary plot 2300 of a conventional ECG waveform showing how the T wave of an abnormal person can appear normal, in accordance with various embodiments. Plot 2300 shows the conventional ECG waveform 2310 of an abnormal person. However, the T wave 2320 appears normal.

(5) It has been difficult to identify which section of an autonomic conduction system is blocked.

Figure 24:
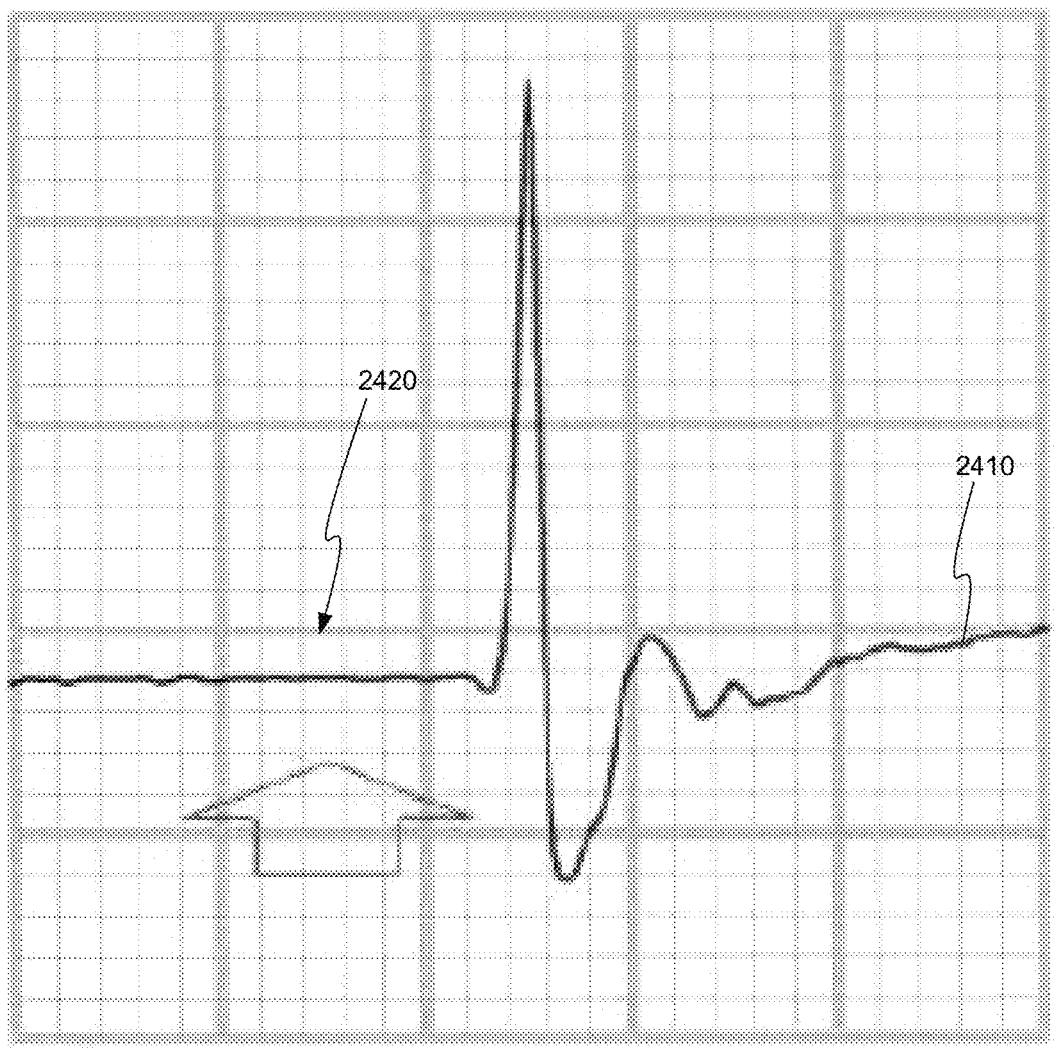
FIG. 24 is an exemplary plot of a conventional ECG waveform showing how the section of an autonomic conduction system cannot be determined from a conduction block, in accordance with various embodiments.

FIG. 24 is an exemplary plot 2400 of a conventional ECG waveform showing how the section of an autonomic conduction system cannot be determined from a conduction block, in accordance with various embodiments. In plot 2400, conduction in the PR interval 2420 of conventional ECG waveform 2410 is blocked. However, from conventional ECG waveform 2410 it is impossible to tell how the signal was conducted down through the conduction system.

(6) It has been difficult to identify the section of an autonomic conduction system that causes a QRS complex to widen or narrow.

Figure 25:
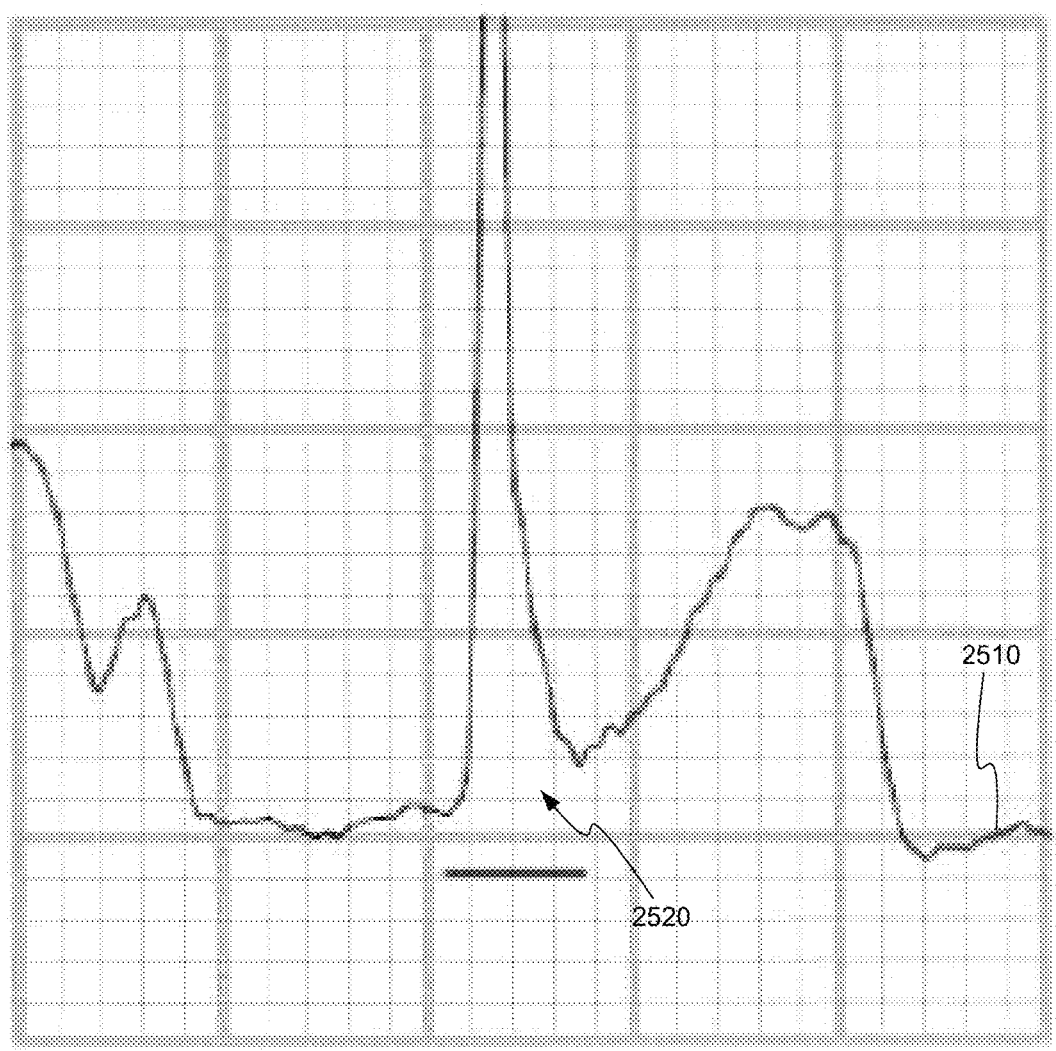
FIG. 25 is an exemplary plot of a conventional ECG waveform showing how the QRS complex is widened in the waveform, in accordance with various embodiments.

FIG. 25 is an exemplary plot 2500 of a conventional ECG waveform showing how the QRS complex is widened in the waveform, in accordance with various embodiments. In plot 2500, although QRS complex 2520 is widened in conventional ECG waveform 2510, it is not possible to determine if this is caused by the atrium or the ventricle.

(7) It has been difficult to identify atrial anatomical positions, such as SA node, AV node, Bundle of His, and Purkinje's, from a conventional ECG waveform, as described above.

Figure 26:
FIG. 26 is an exemplary plot 2600 of a conventional ECG waveform showing how the atrial anatomical positions are difficult to identify, in accordance with various embodiments.

FIG. 26 is an exemplary plot 2600 of a conventional ECG waveform showing how the atrial anatomical positions are difficult to identify, in accordance with various embodiments. In plot 2600, the entire PR interval 2620 of conventional ECG waveform 2610 is abnormal and cannot be measured. A calibration point cannot be mapped. For the patient in this case, the elevated ST segment also cannot be measured. Clinically, an elevated ST segment is also often measured for normal people.

(8) It has been difficult to identify when a premature ventricular beat occurs. It is almost impossible to determine the position of an ectopic premature beat, especially when the premature ventricular beat is accompanied with an aberrant conduction.

Figure 27:
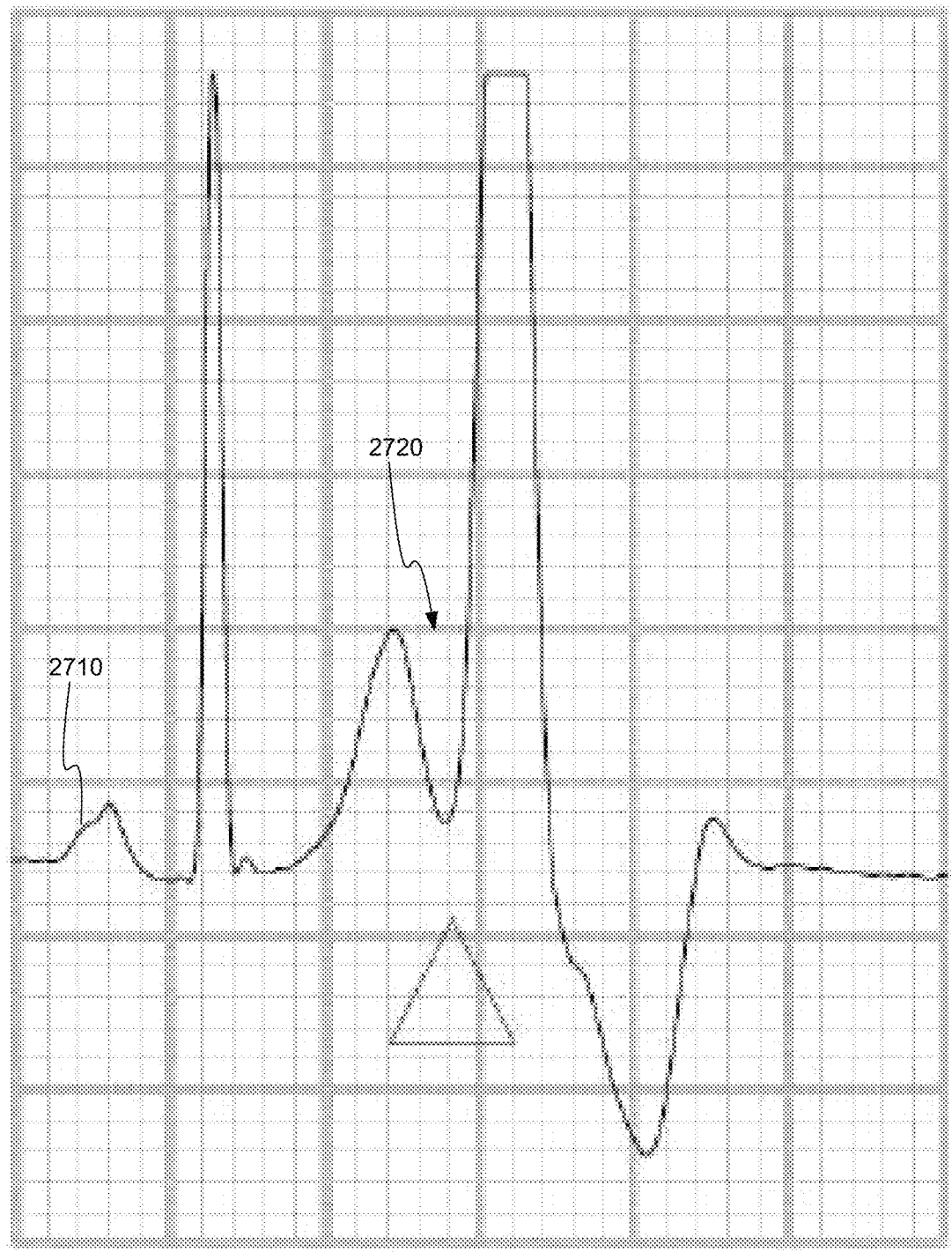
FIG. 27 is an exemplary plot of a conventional ECG waveform showing a premature ventricular beat, in accordance with various embodiments. In plot.

FIG. 27 is an exemplary plot 2700 of a conventional ECG waveform showing a premature ventricular beat, in accordance with various embodiments. In plot. In plot 2700, conventional ECG waveform 2710 includes premature ventricular beat 2720. When premature ventricular beat 2720 occurs, it is not possible to determine whether it is benign or malignant. Not all premature ventricular beats are malignant. In general, a conventional ECG waveform can only show that a premature ventricular beat or premature atrial contraction has occurred.

(9) It has been difficult to identify a malignant arrhythmia.

Figure 28:
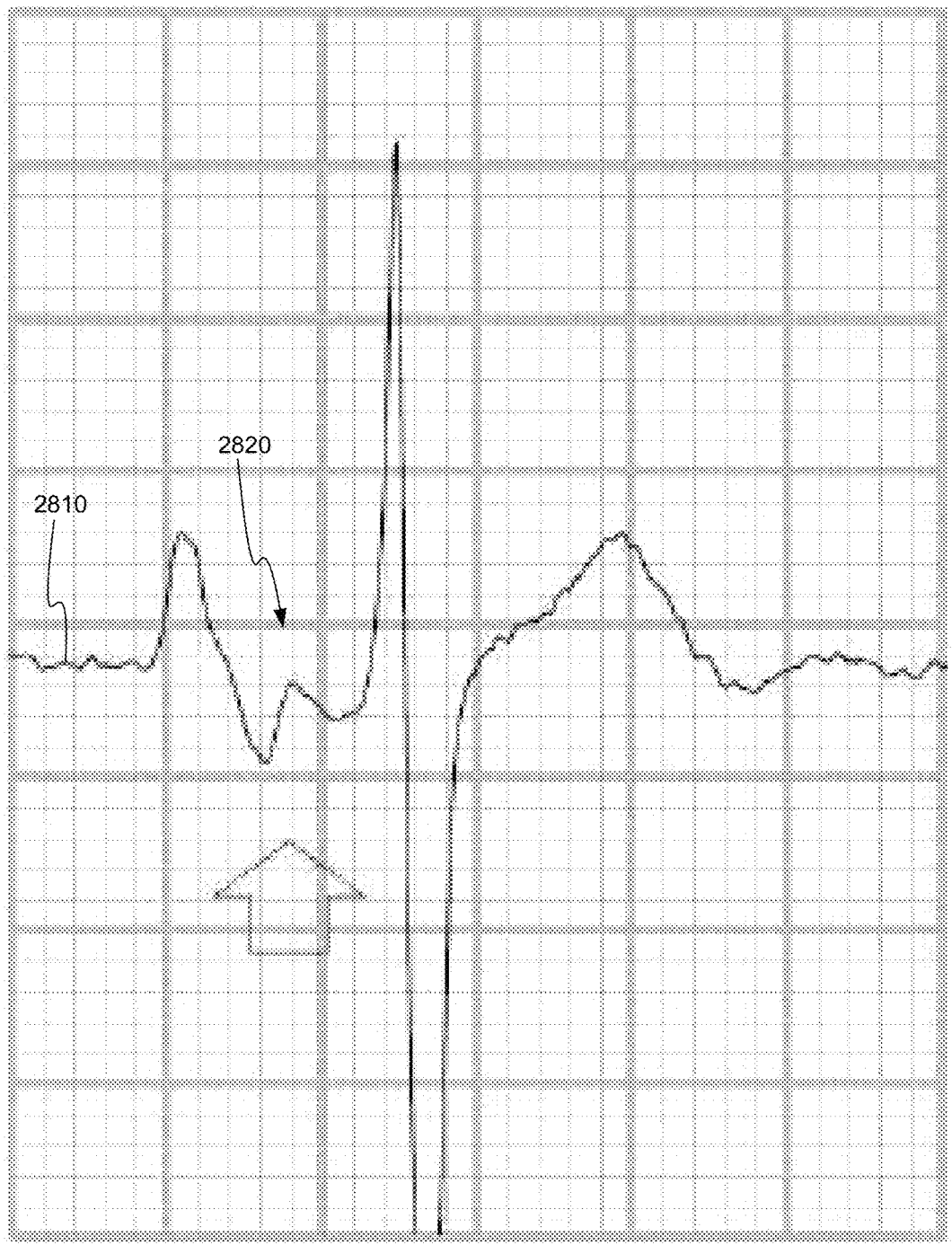
FIG. 28 is an exemplary plot of a conventional ECG waveform showing in atrial conduction block, in accordance with various embodiments.

FIG. 28 is an exemplary plot 2800 of a conventional ECG waveform showing in atrial conduction block, in accordance with various embodiments. In plot 2800, conventional ECG waveform 2810 includes conduction block 2820. However, it is not possible to determine the specific block location of conduction block 2820. The position can determine whether or not the block is malignant. For example, if it is below the His bundle, the block is malignant.

In summary, at an abnormal moment, signals of a conventional ECG waveform often shift positions, and the waveform is changed to a different shape, making it difficult or impossible to estimate. If a conventional ECG waveform is changed in such a way and human intelligence or experience is still relied on to diagnose, a large amount of accuracy is lost.

Automated ECG Analysis and Diagnosis Using AI

As described above, additional systems are needed to further address the technical problems of analyzing the shape and form of the frequency domain signals of a conventional ECG waveform and distinguishing disease conditions from false positives in normal and abnormal populations using the conventional ECG waveform.

In various embodiments, these technical problems are addressed by 1. applying artificial intelligence (AI) algorithms to characterize the shape and form of the frequency domain signals of a conventional ECG waveform; 2. comparing the characterized shape and form of the frequency domain signals to a database of characterized signals from normal and abnormal populations using human like AI algorithms and non-human like AI algorithms; and 3. annotating the conventional ECG waveform with diagnosis information based on the comparison.

Figure 34:
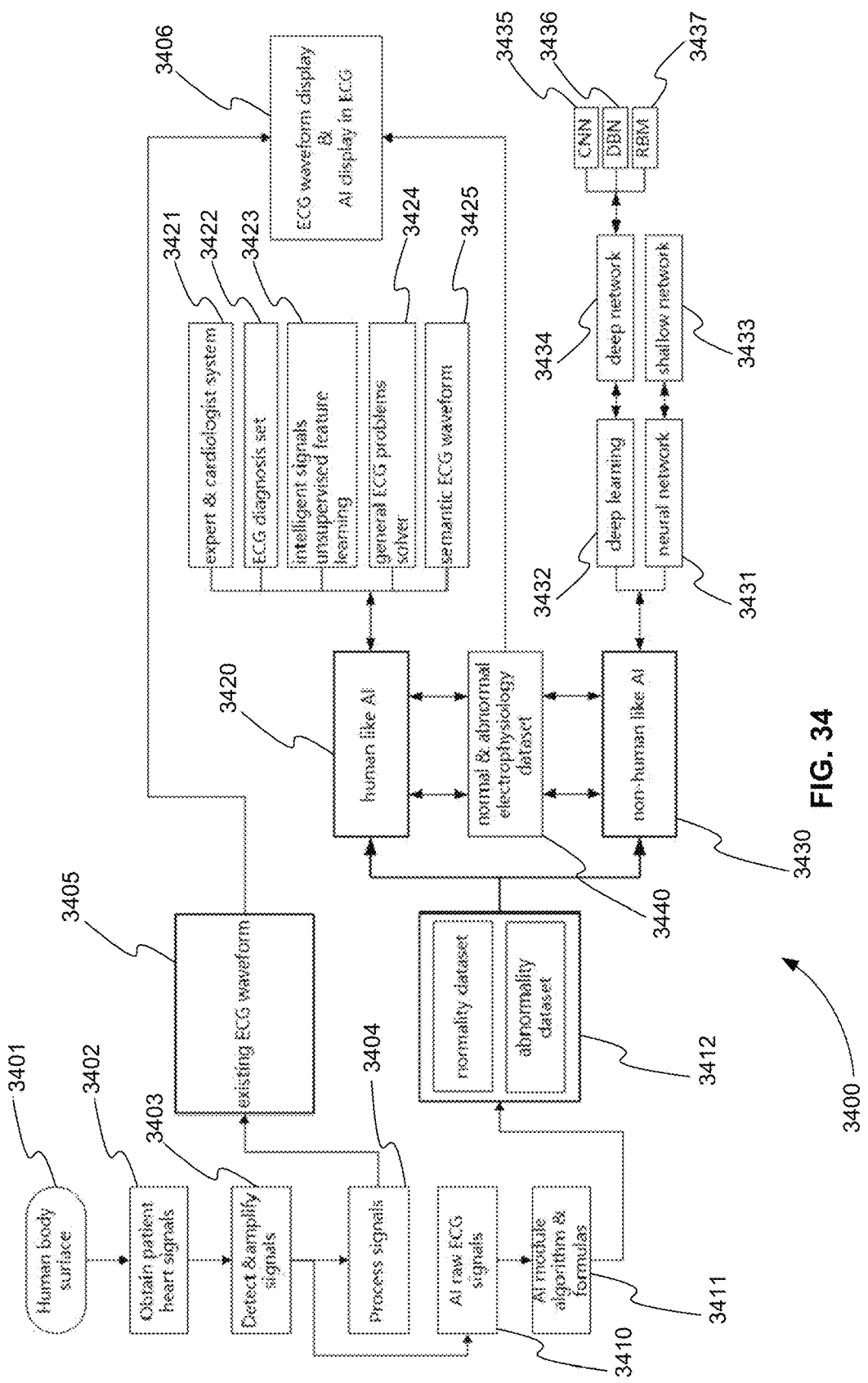
FIG. 34 is an exemplary block diagram of a system for automated ECG analysis and diagnosis using AI, in accordance with various embodiments.

FIG. 34 is an exemplary block diagram 3400 of a system for automated ECG analysis and diagnosis using AI, in accordance with various embodiments. In step 3401 of the system of FIG. 34, two or more electrodes are attached to the skin of a patient to obtain electrical signals from the heart muscle. In various alternative embodiments, the two or more electrodes may be attached directly and invasively to the heart muscle. The two or more electrodes are, for example, conventional ECG leads.

In step 3402, electrical heart signals are obtained from the two or more electrodes.

In step 3403, the electrical heart signals are detected and amplified.

In step 3404, the amplified signals are processed. For example, the signals from a number of different conventional ECG leads are combined.

In step 3405, the combined signals form a conventional ECG waveform.

In step 3406, the conventional ECG waveform is displayed or printed, for example.

In step 3410, the detected signals of step 3403 are obtained and processed to produce two or more frequency domain signals.

In step 3411, the two or more frequency domain signals are processed for characteristics of cardiac electrophysiological signals using one or more AI algorithms.

In step 3412, the cardiac electrophysiological characteristics of the two or more frequency domain signals are compared to databases of similar cardiac electrophysiological characteristics for normal and abnormal populations using the system of FIG. 34.

In step 3420, the cardiac electrophysiological characteristics of the two or more frequency domain signals are compared to the databases using human like AI algorithms. These human like AI algorithms can include, but are not limited to, an expert and cardiologist system 3421, an ECG diagnosis system 3422, an intelligent signals unsupervised feature learning system 3423, a general ECG problem solver 3424, and a semantic ECG waveform system 3425.

In step 3430, the cardiac electrophysiological characteristics of the two or more frequency domain signals are compared to the databases using non-human like AI algorithms. These human like AI algorithms can include, but are not limited to, a neural network algorithm 3431 and a deep learning algorithm 3432. The neural network algorithm 3431 can include a shallow network 3433. The deep learning algorithm 3432 can include a deep network 3434. This deep network 3434 can include, but is not limited to, a convolution all neural network (CNN) 3435, a deep belief net (DBN) 3436, or a restricted Boltzmann machine (RBM).

In step 3440, the results from steps 3420 and 3430 are combined to provide diagnosis information for the conventional ECG waveform.

In step 3406, this diagnosis information is displayed on the conventional ECG waveform.

The system of FIG. 34 provides a number of advantages over conventional automated analysis and diagnosis systems. First of all, it reduces medical and insurance expenses. As a result of the automated diagnosis information patients can avoid invasive and expensive examinations. Secondly, the quick and accurate diagnosis information allows prompt and accurate treatment. In other words, the shortened time for diagnosis allows treatment to occur without delay. Thirdly, the quick and accurate diagnosis helps train doctors more efficiently and can significantly reduce misdiagnosis rates. Fourthly, the quick and accurate diagnosis information can help in the research and development of new target drugs for cardiac treatments. Finally, the use of these AI algorithms in ECG makes these instruments intelligent systems.

In various embodiments, the diagnosis information presented in step 3406 can include, but is not limited to, diagnosis markers or more accurate timing information.

Automated Diagnosis Markers and Timing Information

Figure 35:
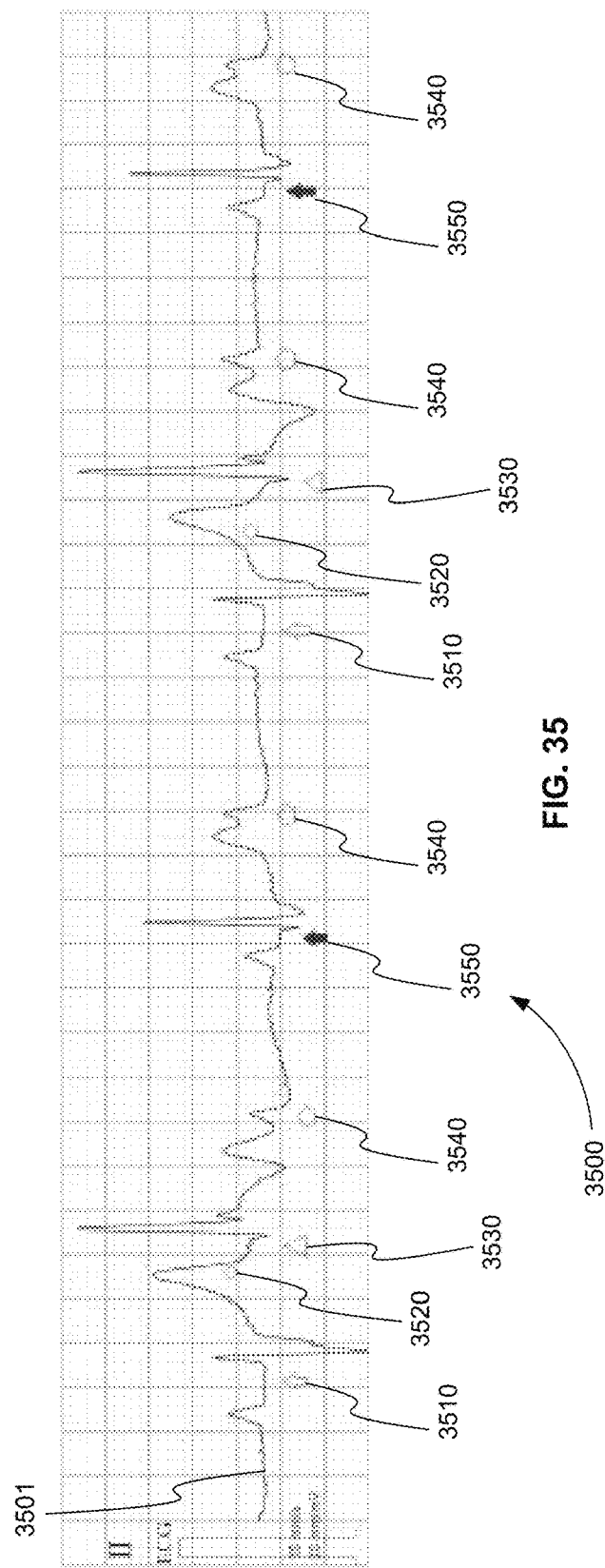
FIG. 35 is an exemplary plot of a conventional ECG waveform annotated with diagnosis marker information, in accordance with various embodiments.

FIG. 35 is an exemplary plot 3500 of a conventional ECG waveform annotated with diagnosis marker information, in accordance with various embodiments. In plot 3500, conventional ECG waveform 3501 is annotated with five different diagnosis markers or prompts. Unfilled arrow marker 3510 represents a specific conduction block position. Unfilled diamond marker 3520 represents a hidden P wave. Unfilled triangle marker 3530 represents a premature ventricular beat position. Unfilled pentagon marker 3540 represents a position where a heartbeat is not conducted. Filled arrow marker 3550 represents a normal heartbeat.

Figure 36:
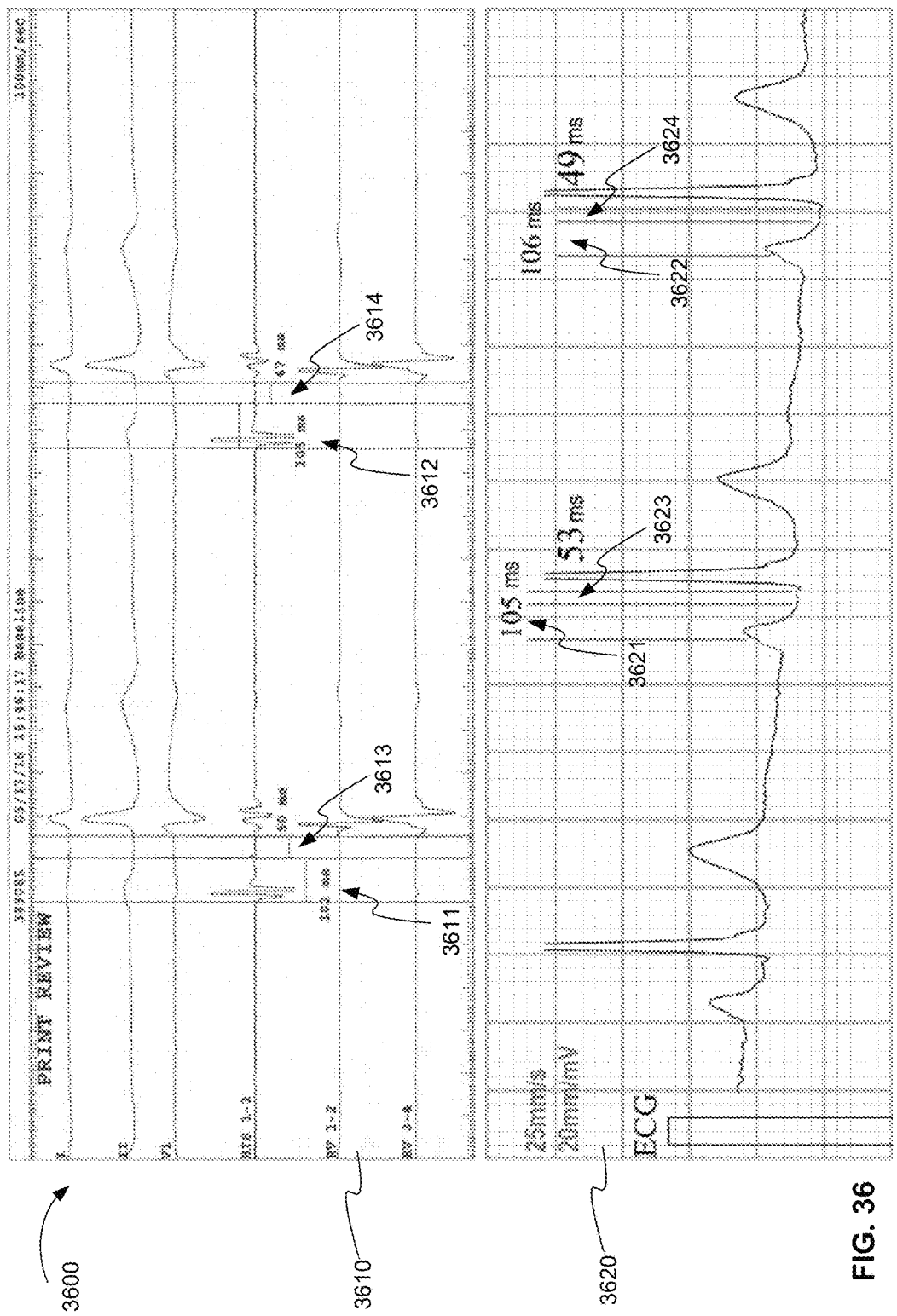
FIG. 36 is an exemplary comparison of timing information from a conventional ECG waveform and from an ECG waveform produced and annotated using an automated analysis and diagnosis system, in accordance with various embodiments.

FIG. 36 is an exemplary comparison 3600 of timing information from a conventional ECG waveform and from an ECG waveform produced and annotated using an automated analysis and diagnosis system, in accordance with various embodiments. Comparison 3600 includes timing information from conventional ECG waveform 3610 and timing information from ECG waveform 3620 produced and annotated using an automated analysis and diagnosis system.

Conventional ECG waveform 3610 measures first AH interval 3611 to be 102 ms and second AH interval 3612 to be 105 ms. In contrast, annotated ECG waveform 3620 measures first AH interval 3621 to be 105 ms and second AH interval 3622 to be 106 ms.

Similarly, conventional ECG waveform 3610 measures first HV interval 3613 to be 50 ms and second HV interval 3612 to be 47 ms. In contrast, annotated ECG waveform 3620 measures first HV interval 3623 to be 53 ms and second HV interval 3624 to be 49 ms.

Comparison 3600 shows that an automated analysis and diagnosis system can produce more accurate timing information than a conventional ECG system.

System for Identifying and Annotating Cardiac Electrophysiological Signals

The conventional ECG's P-QRS-T waveform records the normal atrial and ventricular muscles, which is composed of high frequency (HF), ultra high frequency (UHF), and super high frequency (SHF) signals. The heart is a micro-current organ. The atrium has two electrical channels, while the ventricle has multilayer channels. In conventional ECG systems the majority of the high frequency signals of the ECG waveform are convoluted with other signals. Besides the normal atrial muscle, there also exists a special conduction system. In addition to the normal Ventricular muscle, there are multilayer characteristic cellular groups. These specific signals are not accurately displayed in the conventional ECG P and T waves. This is the reason why the conventional ECG waveform has not evolved and has been difficult to change.

The reason why the conventional ECG waveform has not evolved is related to the developmental history of mathematics. Since its invention, ECG has only had an empirical formula, which is basically a guide, such as: III lead link is equal to II lead minus I lead. However, no mathematical formula proof for this formula exists. Galvani founded electrophysiology in 1791. Matteueci discovered heart electrical activity in 1842. In 1898, Waller proposed the electrocardiogram dipole distribution theory, in 1912 recorded the electrical waveform by electrocardiogram, and named this sinusoidal line the P-QRS-T. A conventional ECG system scans and records this sinusoidal wave.

Harmonics and Discontinuities

Since as early as the 17th century, however, there has been a huge controversy in the scientific-mathematical world. In the academic world, an argument arose between Fourier and Lagrange, which focused on whether the sine wave curve contained minute, harmonic frequency signals. It wasn't until 1898 (ECG theory proposed the same year) that Nobel Prize winner Albert Abraham Michelson successfully developed the harmonic analyzer. Using this method, the American mathematical physicist Josiah Willard Gibbs confirmed that a sinusoidal wave can contain a harmonic image, which was later called the Gibbs phenomenon. The pioneers of the traditional ECG did not mean to discover this confirmation of a great theory of mathematics and, until this day, this discovery has not been taken seriously. Harmonics are cycles. The signal can be the sum of many sine waves because the frequency of the ECG sine wave is different, and there are harmonic (wavelet or subwaveforms) signals between and within the P-QRS-T waveforms. For more than a century, scientists have been studying the ECG waveform, ignoring basic signal processing (mathematics) and ignoring the fact that sine waves are convolutions of multitudes of discontinuities.

In various embodiments, a complete set of signal processing systems have been developed to measure these subwaveforms and discontinuities. For example, the visual EPCG waveform has been confirmed within the P-QRS-T waveform. It contains many small subwaveforms (harmonics). These are located in the conventional ECG waveform in front of the P wave, in the P wave itself, after the P wave, to the right and left side of the QRS, in the ST segment, in the T wave, and after the T wave, for example. In other words, it has been confirmed that the conventional ECG periodic signal is composed of the sum of its harmonics.

ST Segment Harmonics and Discontinuity Points

Most recently and in various embodiments, new subwaveforms and discontinuity points have been discovered in relation to the ST segment. Exemplary ST segment 260 is shown in FIG. 2, for example. The ST segment is one of the least understood elements of a conventional ECG waveform.

Figure 39:
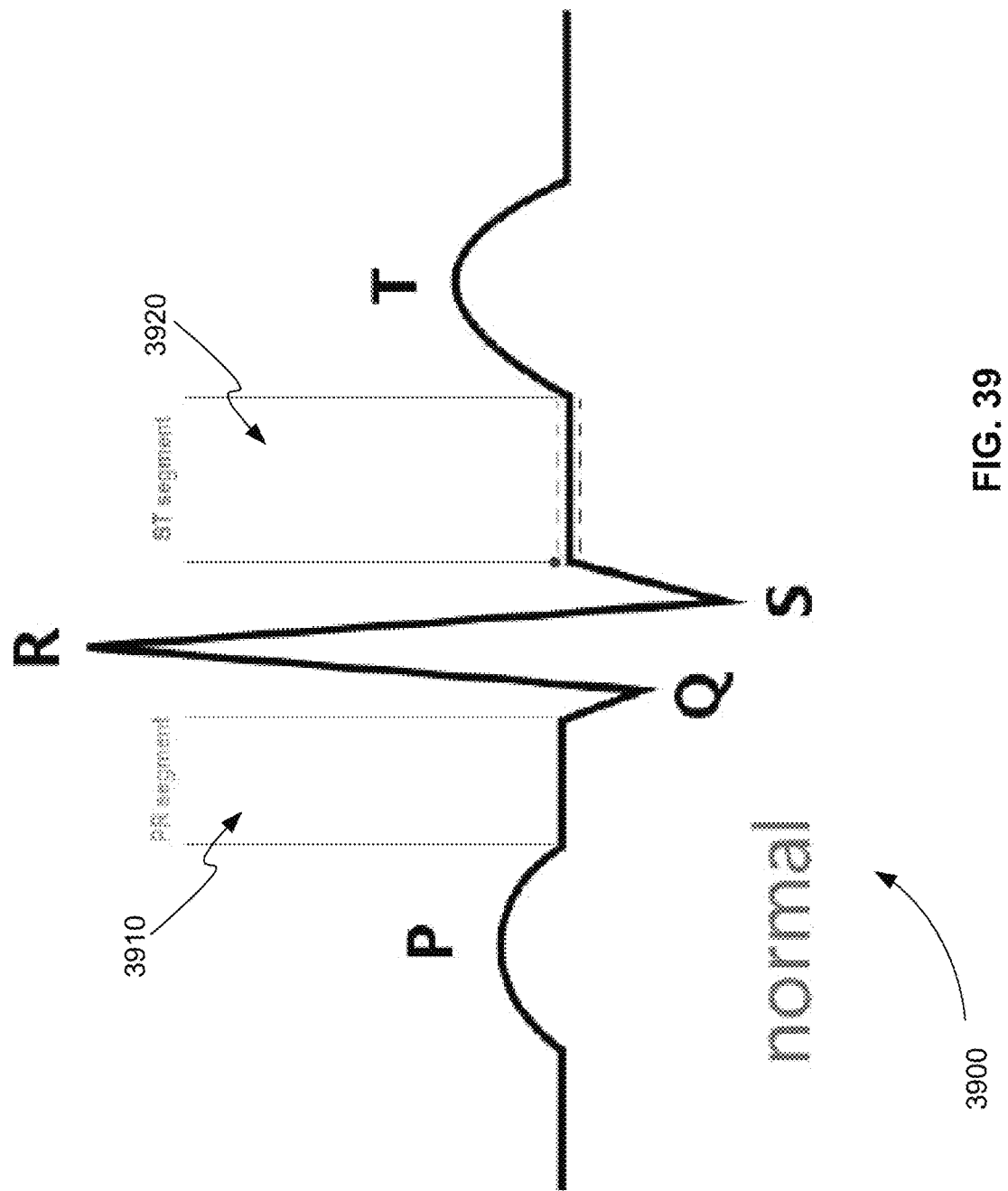
FIG. 39 is an exemplary ECG waveform plot showing the relative positions of the PR and ST segments for a normal heartbeat, in accordance with various embodiments.

FIG. 39 is an exemplary ECG waveform plot 3900 showing the relative positions of the PR and ST segments for a normal heartbeat, in accordance with various embodiments. In plot 3900, PR segment 3910 and ST segment 3920 have the same position vertically.

Conventionally, there is only one standard for accessing the ST segment: either elevation or descent.

Figure 40:
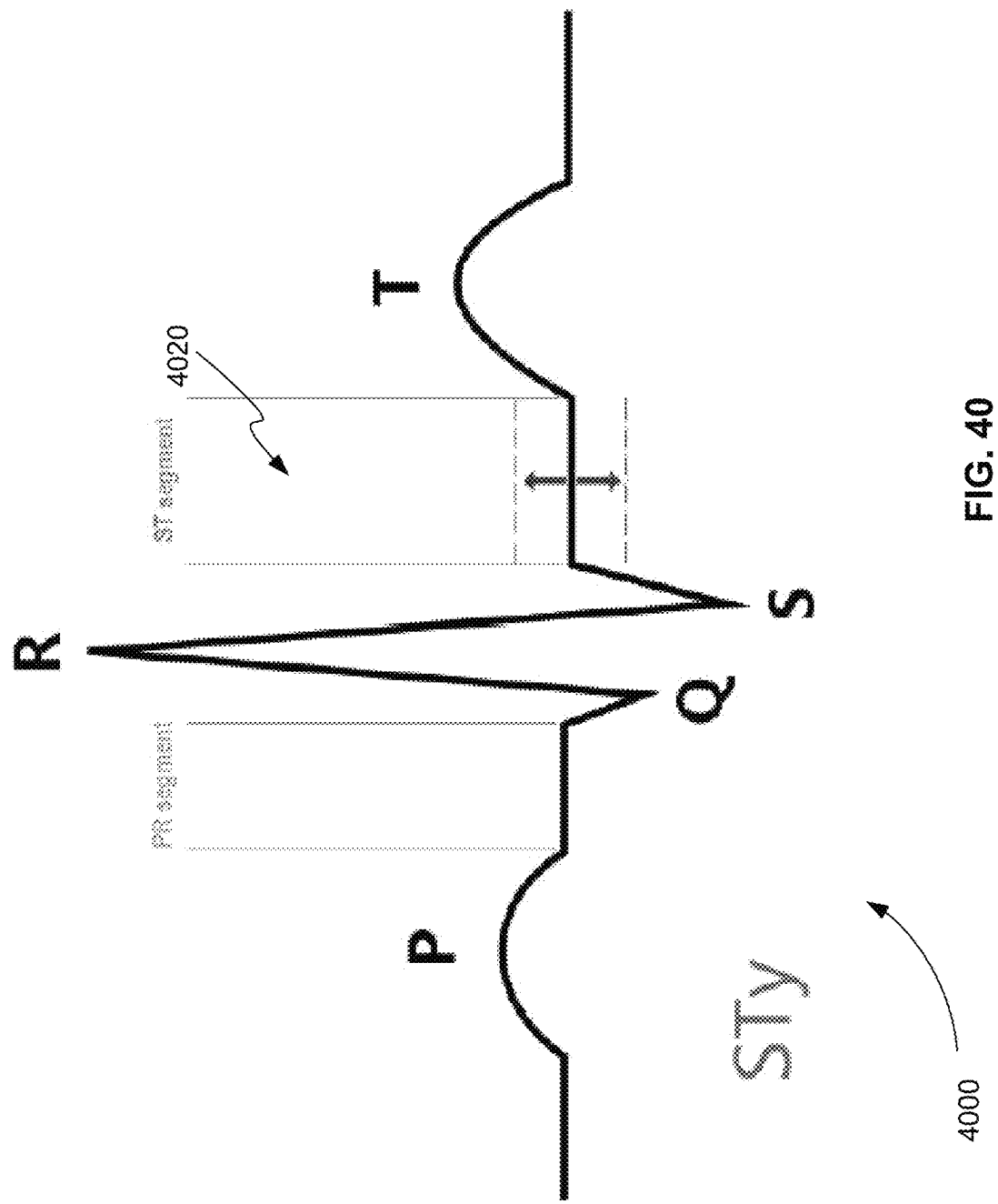
FIG. 40 is an exemplary ECG waveform plot showing how the ST segment can shift vertically due to abnormal conditions, in accordance with various embodiments.

FIG. 40 is an exemplary ECG waveform plot 4000 showing how the ST segment can shift vertically due to abnormal conditions, in accordance with various embodiments. In plot 4000, ST segment 4020 can elevate or descend vertically depending on the abnormal condition. This standard or rule can be referred to as STy.

According to the STy standard, one or more (mV) movements upward from the baseline x-axis (isoelectric line) equate to an elevation. Similarly, one or more mV movements downward from the baseline x-axis equate to descent or depression. The problem with this ST segment standard, is that 90% of normal data for healthy people usually shows an ST segment elevation. In addition, abnormal data for unhealthy people is usually not represented as a simple elevation or a descent.

Figure 41:
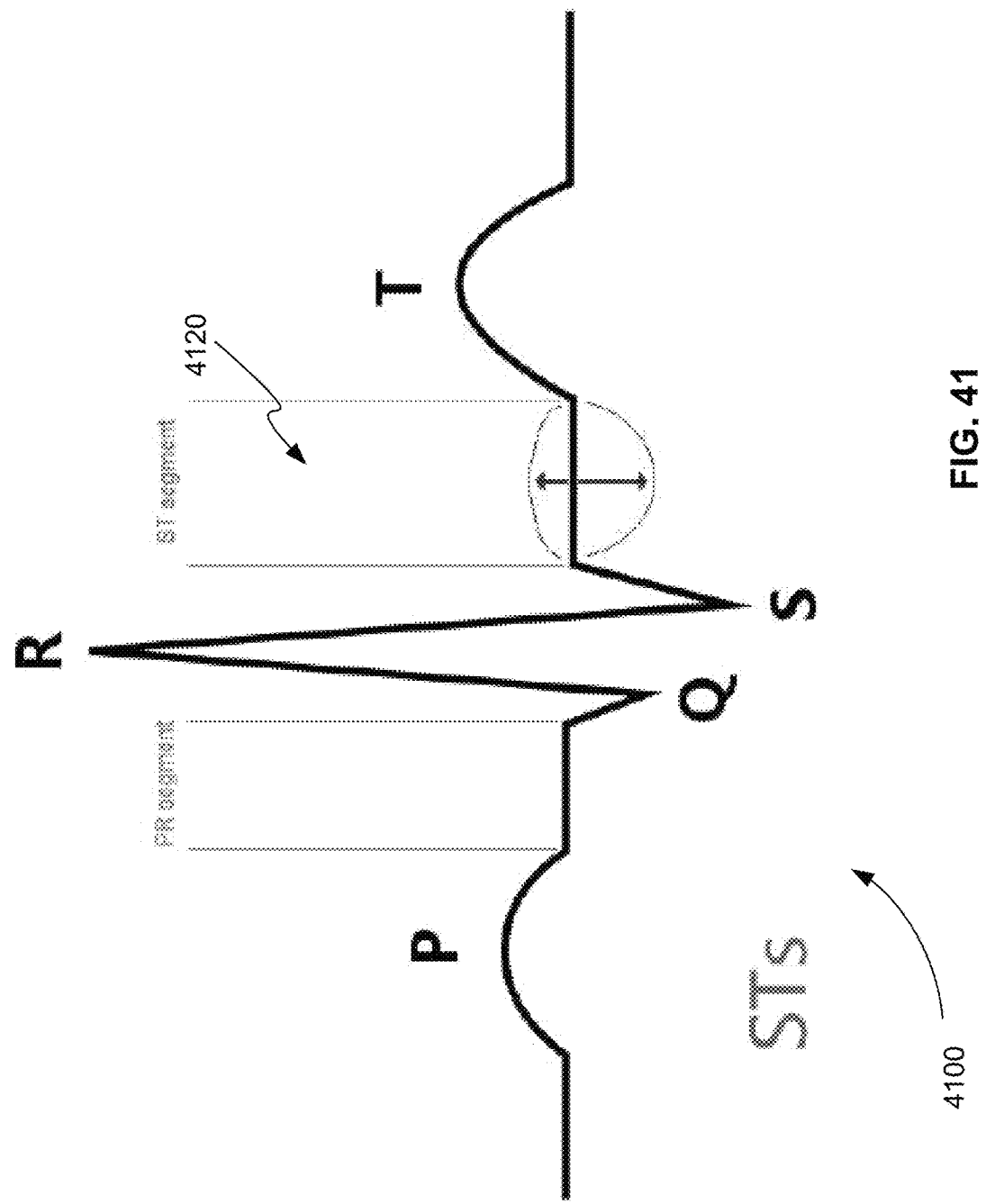
FIG. 41 is an exemplary ECG waveform plot showing how the ST segment can be deformed due to abnormal conditions, in accordance with various embodiments.

FIG. 41 is an exemplary ECG waveform plot 4100 showing how the ST segment can be deformed due to abnormal conditions, in accordance with various embodiments. In plot 4100, ST segment 4120 can be deformed so that it forms a concavity or convexity vertically, for example.

Figure 42:
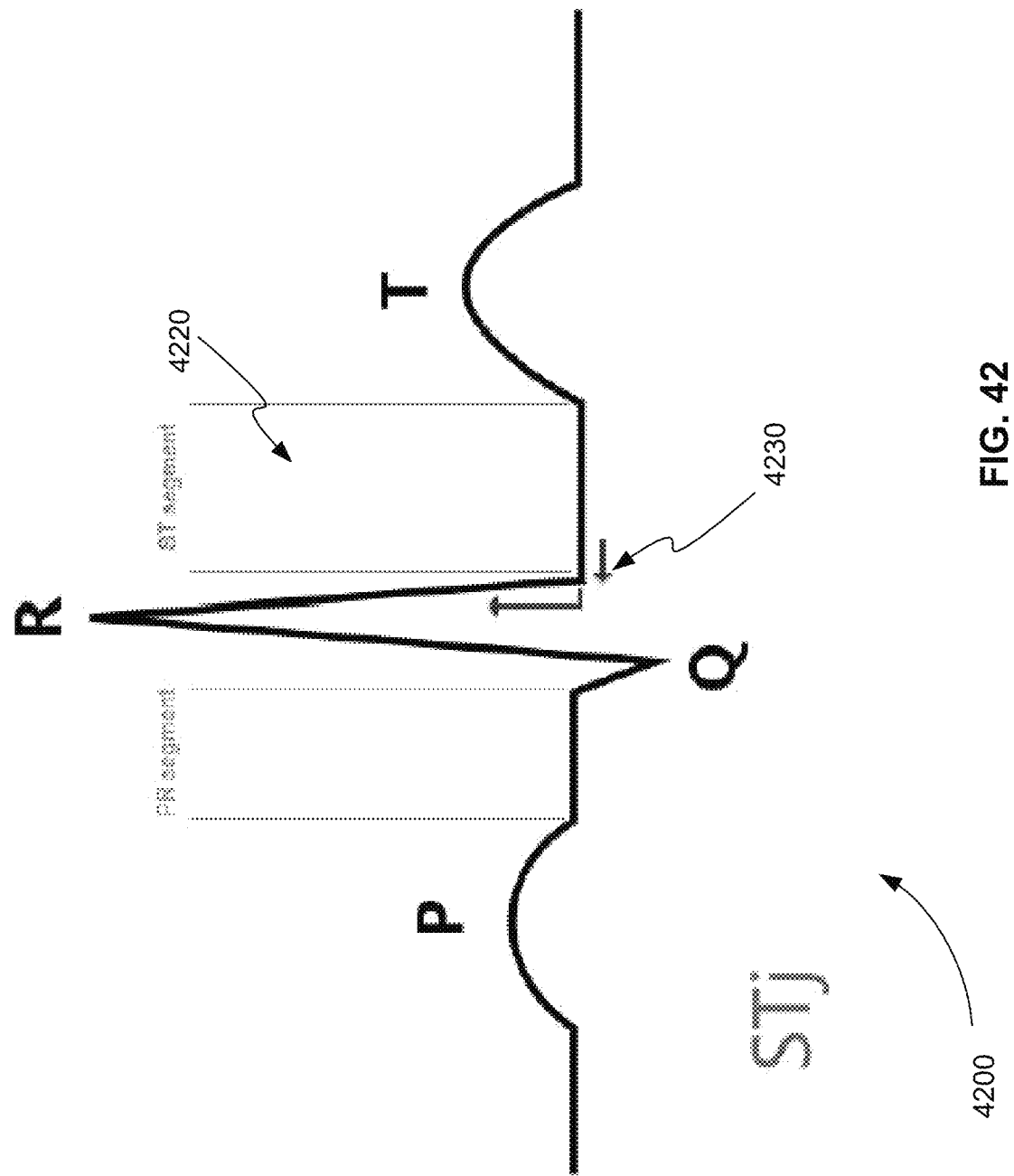
FIG. 42 is an exemplary ECG waveform plot showing how the vertical or horizontal movement of the end of an RS segment can affect the ST segment due to abnormal conditions, in accordance with various embodiments.

FIG. 42 is an exemplary ECG waveform plot 4200 showing how the vertical or horizontal movement of the end of the RS segment can affect the ST segment due to abnormal conditions, in accordance with various embodiments. In plot 4200, the movement of end 4230 of RS segment removes the difference between the S point and J point of ST segment 4220, for example.

Figure 43:
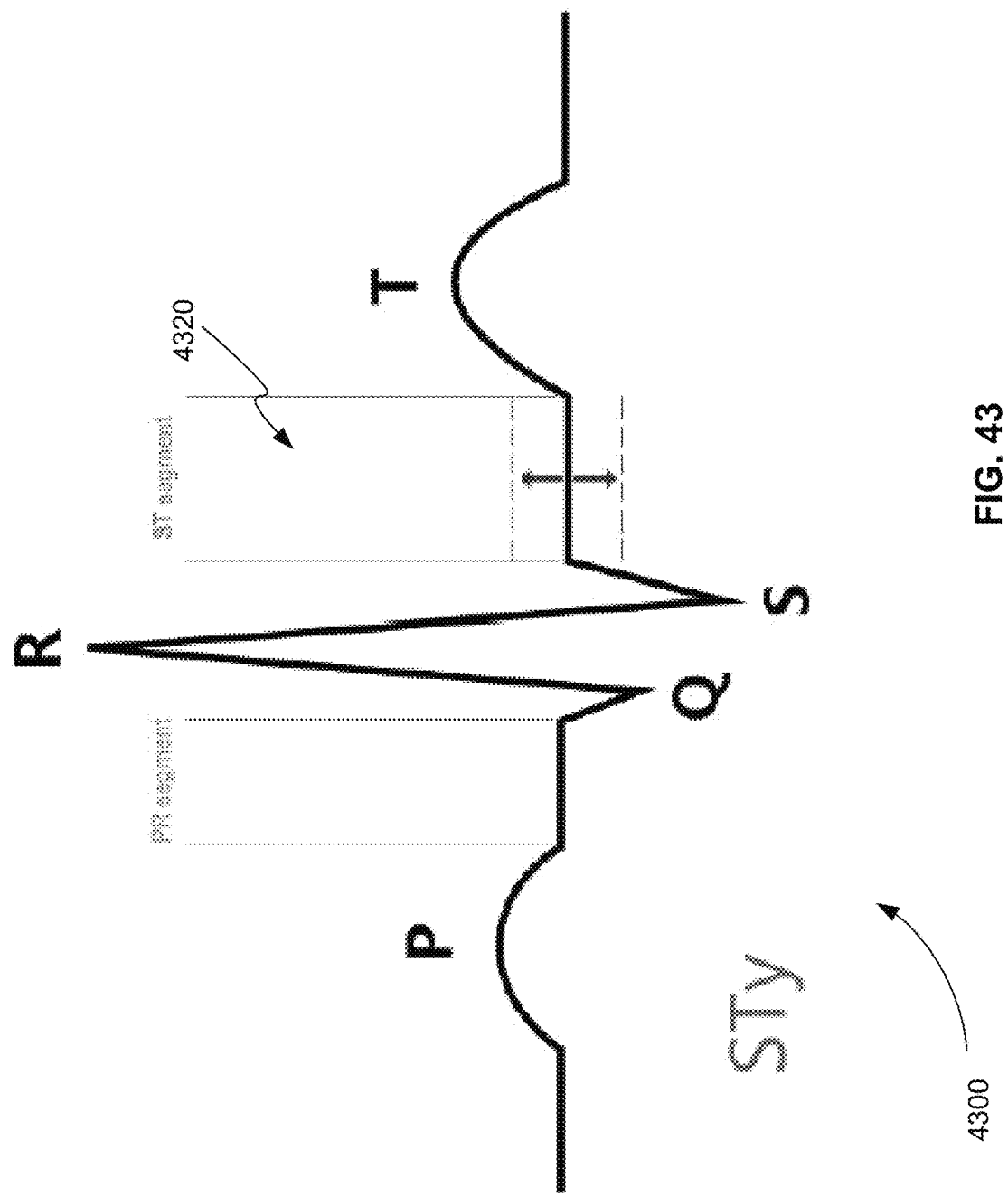
FIG. 43 is an exemplary ECG waveform plot showing how the ST segment can shift horizontally due to abnormal conditions, in accordance with various embodiments.

FIG. 43 is an exemplary ECG waveform plot 4300 showing how the ST segment can shift horizontally due to abnormal conditions, in accordance with various embodiments. In plot 4300, the length of ST segment 4320 can shorten or widen horizontally depending on the abnormal condition.

Figure 44:
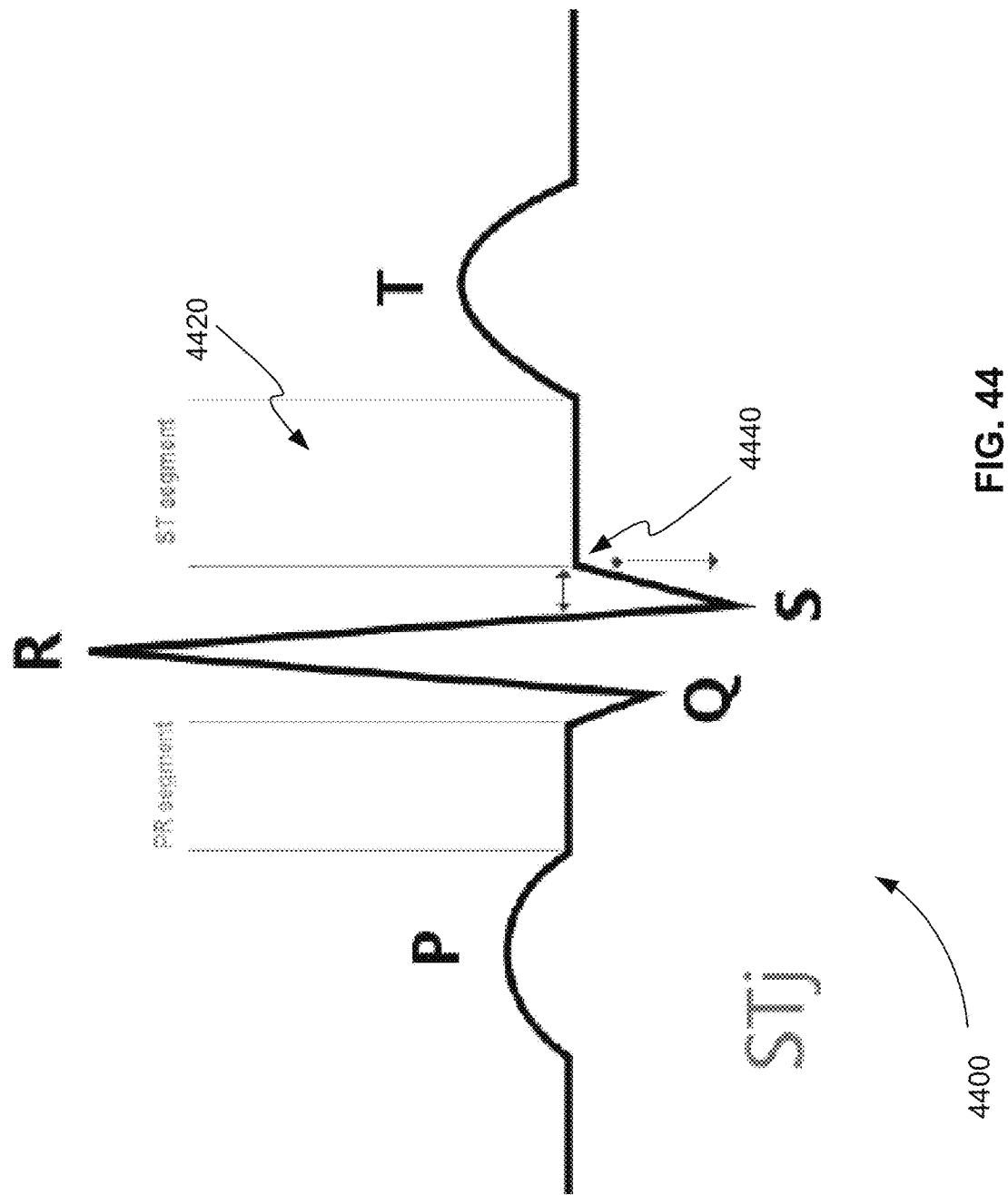
FIG. 44 is an exemplary ECG waveform plot showing how vertical or horizontal movement of the J point can affect the ST segment due to abnormal conditions, in accordance with various embodiments.

FIG. 44 is an exemplary ECG waveform plot 4400 showing how vertical or horizontal movement of the J point can affect the ST segment due to abnormal conditions, in accordance with various embodiments. In plot 4400, the movement of J point 4440 can change the length or slope of ST segment 4420, for example.

In various embodiments, new standards or rules are developed to assess the ST segment based on harmonic waveforms and points of discontinuity. These standards or rules are used in AI algorithms, for example.

In one embodiment, an STx standard is developed. A conventional ECG system cannot measure the sum of the ST segment and the T segment (x-axis time parameter). The STx standard measures the sum of the ST segment and the T segment. This sum is typically <380 ins. This STx standard is extremely important and can be compared to the borderlines between countries. It represents time value changes. The following are times changes which can occur. (1) The time value change may be >100 ms. (2) The time value change may be <40 ms. (3) The time value change may be =0 ms. (4) The ST-T segment may also be represented as a, negative curve (lower than the isoelectric line). (5) These time changes are all based on relation to the x-axis.

In another embodiment, an STa standard is developed. The "a" relates to amplitude, (1) The top peak of the T wave may be lower than the P wave's top peak, or the two waves are equal. (2) The starting point of the P wave is greater than the isoelectric line. (3) T wave terminal point is greater than the isoelectric line. (4) The T wave's time value is less than P wave's time value (reversed). All of these changes will cause the ST segment to deform.

In another embodiment, an Si's standard is developed. The "s" relates to the slope. This is only related to the terminal slope of the ST segment in relation to the initial slope of the T wave. The following are new pattern recognition rules. (1) This slope shrinks or shortens, (2) This slope is represented as the isoelectric line. (3) This slope is lower than the isoelectric line. (4) The ST slope is upside-down, but the T wave is normal. (5) This slope takes on an upward slope but looks convex instead of the traditional concave slope. (6) The ST segment slope completely disappears, and the T wave begins directly after the QRS segment (this happens very often), (7) The ST segment is completely horizontal with the isoelectric line; the two halves of the T wave are complete mirrors of each other in both angle and slope.

In another embodiment, an STj standard is developed. The "j" relates to the J-point. (1) The S point to the J-point time is increased. (2) S-point and J-point disappear; there is almost a 90° angle between the RS end and ST segment start. (3) The S-point and J-point are concealed within the RS segment; the J-point is above the isoelectric line. (4) The J-point falls below the isoelectric point, concealed deep into RS.

FIG. 45 is an exemplary comparison 4500 of two ECG waveform plots exhibiting ST segment changes that can be identified using the STy standard, in accordance with various embodiments. In plot 4510, the ST segment is identified as elevating according to the STy standard. In plot 4520, the ST segment is identified as descending according to the STy standard.

FIG. 46 is an exemplary comparison 4600 of two ECG waveform plots exhibiting ST segment changes that can be identified using the STx standard, in accordance with various embodiments. In plot 4610, the ST segment is identified as widened according to the STx standard. In plot 4620, the ST segment is identified as shortened according to the STx standard.

FIG. 47 is an exemplary comparison 4700 of two ECG waveform plots exhibiting ST segment changes that can be identified using the STs and STy standards (STs+STy), in accordance with various embodiments. In plot 4710, the ST segment is identified as a down-sloping depression according to the STs and STy standards (STs+STy). In plot 4720, the ST segment is identified as an up-sloping depression according to the STs and STy standards (STs+STy).

FIG. 48 is an exemplary comparison 4800 of two ECG waveform plots exhibiting ST segment changes that can be identified using the STy, and STx standards (STj+STy+STx), in accordance with various embodiments. In plot 4810, the ST segment is identified as a depression according to the STj, STy, and STx standards (STj+STy+STx). In plot 4820, the ST segment is identified as vanishing according to the STj, STy, and STx standards (STj+STy+STx) the STs and STy standards (STs+STy).

Figure 49:
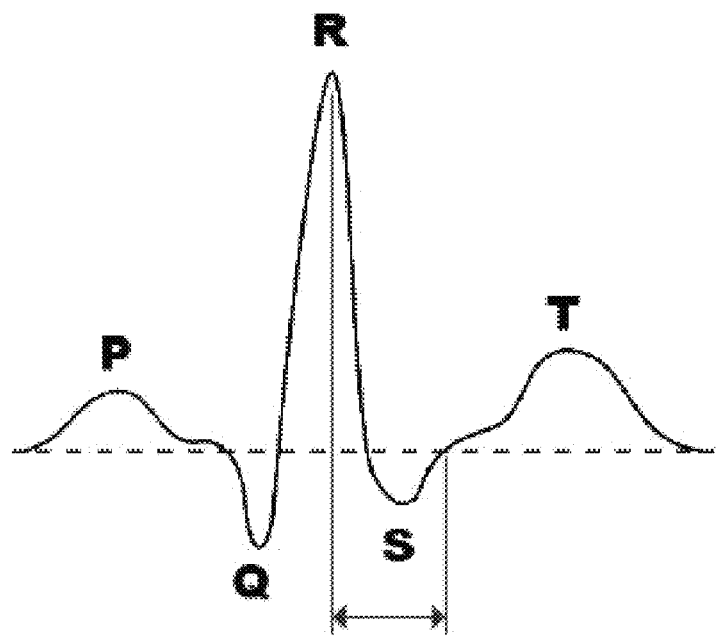
FIG. 49 is an exemplary ECG waveform plot of an ST segment change that can be identified using the STx and STj standards (STx+STj), in accordance with various embodiments.

FIG. 49 is an exemplary ECG waveform plot 4900 of an ST segment change that can be identified using the STx and STj standards (STx+STj), in accordance with various embodiments. In plot 4900, the ST segment is identified as having a widened RJ interval according to the STx and STj standards (STx+STj).

Analysis and Diagnosis System

The systems of the '204 Patent and the '930 Patent have used different signal processing methods to detect the harmonic signals and discontinuity points of a conventional ECG waveform. In various embodiments, artificial intelligence (AI) in conjunction with a database of normal and abnormal ECG data is used to detect the harmonic signals and discontinuity points of a conventional ECG waveform and to annotate cardiac electrophysiological signals in the ECG waveform as normal or abnormal.

Figure 37:
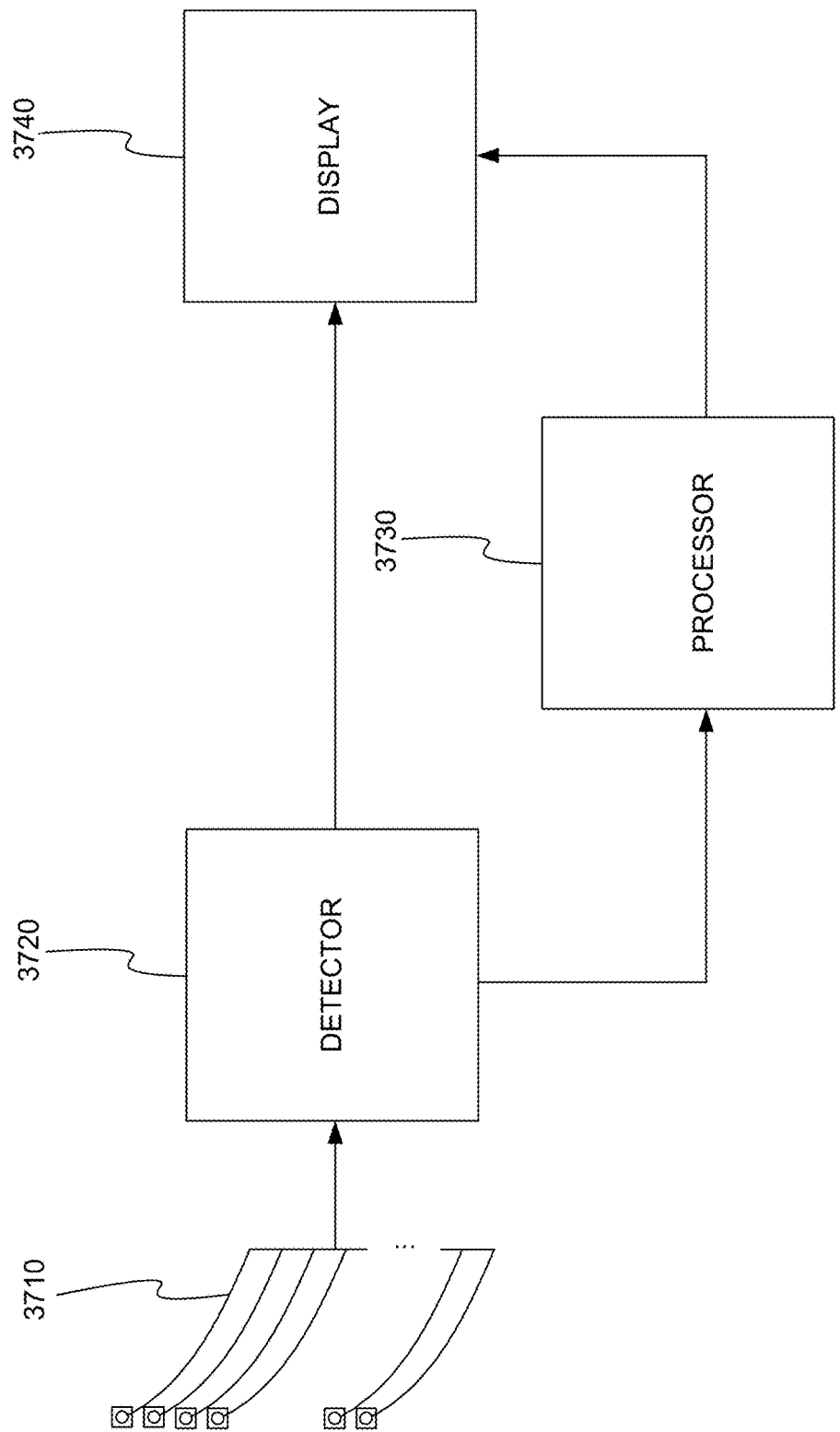
FIG. 37 is a block diagram of an ECG system for identifying and annotating cardiac electrophysiological signals in an ECG waveform as normal or abnormal during measurement of the ECG waveform, in accordance with various embodiments.

FIG. 37 is a block diagram 3700 of an ECG system for identifying and annotating cardiac electrophysiological signals in an ECG waveform as normal or abnormal during measurement of the ECG waveform, in accordance with various embodiments. Electrodes 3710 are attached to the skin of a patient in a noninvasive measurement, for example. In an alternative embodiment, electrodes 3710 are attached directly on the surface of a beating heart of a patient. Electrical signals produced by a beating heart are detected between pairs of electrodes 3710.

A voltage signal is detected between two electrodes 3710 by detector 3720. Detector 3720 also amplifies the voltage signal. Detector 3720 converts the electrical impulses to an ECG waveform for each heartbeat of the beating heart. Detector 3720 converts the voltage signal to a digital voltage signal using an analog to digital converter (A/D), for example. Detector 3720 provides the detected and amplified voltage signal from each pair of electrodes 3710 directly to display device 3740 to display the ECG waveform. The ECG waveform includes conventional P, Q, R, S, T, U, and J waveforms, for example. Detector 3720 also provides the detected and amplified voltage signal from each pair of electrodes 3710 directly to processor 3730.

Processor 3730 can be a separate electronic device that can include, but is not limited to, an application specific integrated circuit (ASIC), a field programmable gate array (FPGA), or a general purpose processor or computer, such as the system of FIG. 1. Processor 3730 can be software implemented on another processor of the ECG device, such as a processor of display device 3740. Processor 3730 can also include a remote server computer.

Processor 3730 receives the ECG waveform for at least one heartbeat from detector 3720. Processor 3730 converts the ECG waveform to a frequency domain waveform. Processor 3730 separates the frequency domain waveform into two or more different frequency domain waveforms. Processor 3730 converts the two or more different frequency domain waveforms into a plurality of time domain cardiac electrophysiological subwaveforms and discontinuity points between these subwaveforms of the ECG waveform.

Processor 3730 compares the plurality of subwaveforms and discontinuity points to a database (not shown) of subwaveforms and discontinuity points for cardiac electrophysiological signals of ECG waveforms for a plurality of known and normal and abnormal patients. Processor 3730 identifies at least one subwaveform or one or more discontinuity points of the plurality of subwaveforms and discontinuity points as a normal or abnormal electrophysiological signal of the ECG waveform based on the comparison.

Display device 3740 is an electronic display device, a printer, or any combination of the two. Display device 3740 displays the ECG waveform for the at least one heartbeat of the beating heart. Display device 3740 also displays one or more markers at the location of the at least one subwaveform or the one or more discontinuity points on the ECG waveform and identifies the one or more markers as a normal or abnormal cardiac electrophysiological signal. For example, FIGS. 35 and 36 show how one or more markers are displayed on ECG waveforms to indicate normal or abnormal cardiac electrophysiological signals. The one or more markers can be identified as a normal or abnormal cardiac electrophysiological signal using symbols, colors, or text, for example.

In various embodiments, processor 3730 converts the ECG waveform to a frequency domain waveform, separates the frequency domain waveform into two or more different frequency domain waveforms, and converts the two or more different frequency domain waveforms into a plurality of time domain cardiac electrophysiological subwaveforms and discontinuity points using an artificial intelligence algorithm. The artificial intelligence algorithm includes a multivariable calculus algorithm, for example.

In various embodiments, processor 3730 compares the plurality of subwaveforms and discontinuity points to a database of subwaveforms and discontinuity points using a human like artificial intelligence algorithm.

In various embodiments, the human like artificial intelligence algorithm includes an expert and cardiologist system. This system evaluates the comparison based on morphological rules developed from cardiologists. In other words, the shape differences are compared using rules based on pattern recognition and doctors' experiences.

In various embodiments, the human like artificial intelligence algorithm includes an ECG diagnosis system. This system evaluates the comparison based on morphological patterns and their correlation to specific diseases.

In various embodiments, the human like artificial intelligence algorithm includes an intelligent signals unsupervised feature learning system. This system evaluates the comparison based on morphological patterns learned over time by the system.

In various embodiments, the human like artificial intelligence algorithm includes a general ECG problem solver. This system evaluates the comparison based on one or more known conditions or conflicting conditions including, but not limited to, heart failure atrium fibrillation (AF), atrial conductor block, premature atrial contraction (PAC), premature ventricular contraction (PVC), atrial tachycardia, and ventricular tachycardia.

In various embodiments, the human like artificial intelligence algorithm includes a semantic ECG waveform system. This system evaluates the comparison based on additional signal processing rather than pattern recognition.

In various embodiments, processor 3730 compares the plurality of subwaveforms and discontinuity points to a database of subwaveforms and discontinuity points using a non-human like artificial intelligence algorithm.

In various embodiments, the human like artificial intelligence algorithm includes a neural network. The neural network can be a shallow network, for example.

In various embodiments, the human like artificial intelligence algorithm includes a deep learning algorithm. The deep learning algorithm can include a deep network, for example. The deep network can include, but is not limited to, convolution all neural network (CNN), a deep belief net (DBN), or a restricted Boltzmann machine (RBM).

Method for Identifying and Annotating Cardiac Electrophysiological Signals

Figure 38:
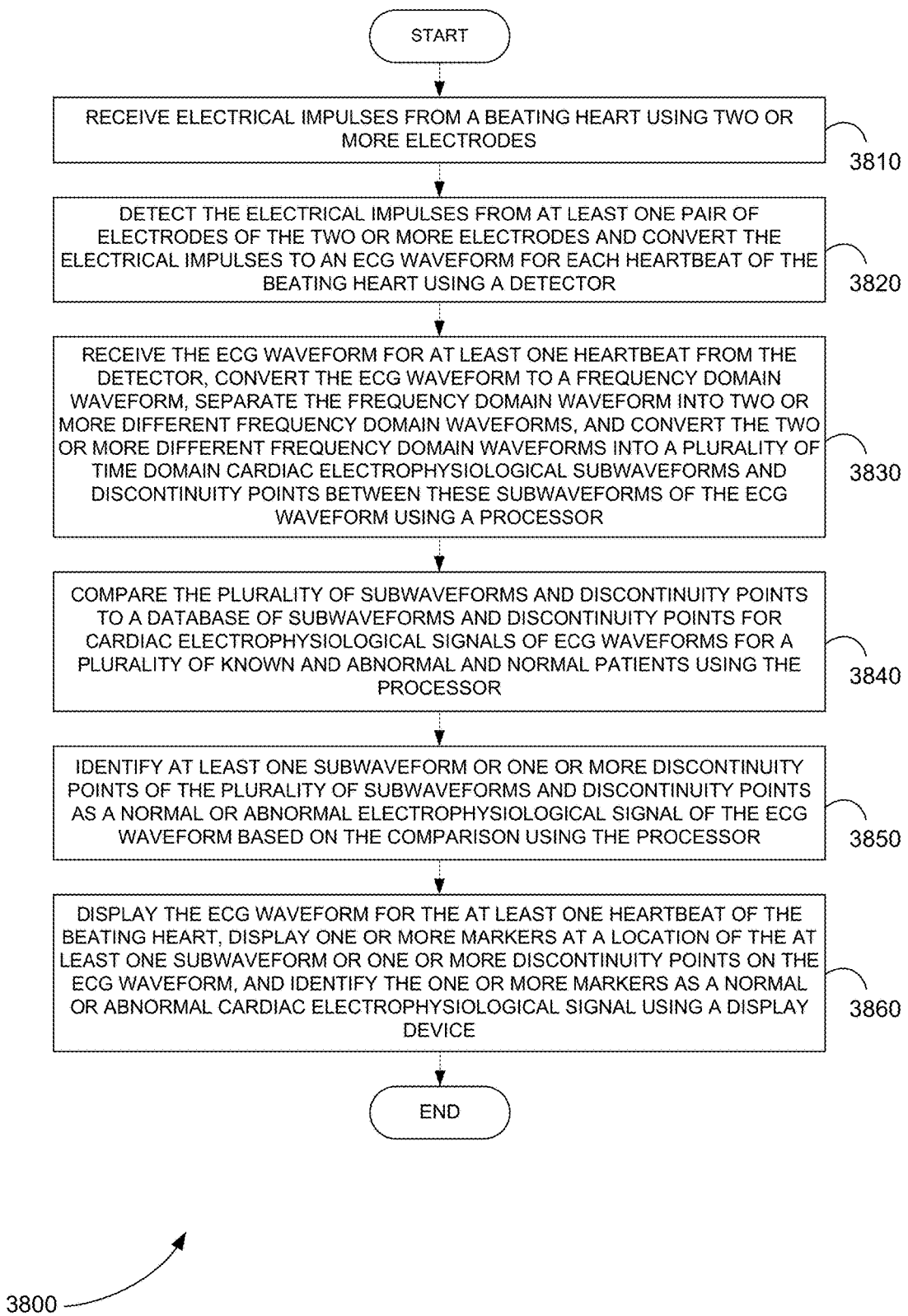
FIG. 38 is a flowchart showing a method for identifying and annotating cardiac electrophysiological signals in an ECG waveform as normal or abnormal during measurement of the ECG waveform, in accordance with various embodiments.

FIG. 38 is a flowchart showing a method 3800 for identifying and annotating cardiac electrophysiological signals in an ECG waveform as normal or abnormal during measurement of the ECG waveform, in accordance with various embodiments.

In step 3810 of method 3800, electrical impulses are received from a beating heart using two or more electrodes.

In step 3820, the electrical impulses are detected from at least one pair of electrodes of the two or more electrodes and converted to an ECG waveform for each heartbeat of the beating heart using a detector.

In step 3830, the ECG waveform for at least one heartbeat is received from the detector, the ECG waveform is converted to a frequency domain waveform, the frequency domain waveform is separated into two or more different frequency domain waveforms, and the two or more different frequency domain waveforms are converted into a plurality of time domain cardiac electrophysiological subwaveforms and discontinuity points between these subwaveforms of the ECG waveform using a processor.

In step 3840, the plurality of subwaveforms and discontinuity points are compared to a database of subwaveforms and discontinuity points for cardiac electrophysiological signals of ECG waveforms for a plurality of known and normal and abnormal patients using the processor.

In step 3850, at least one subwaveform or one or more discontinuity points of the plurality of subwaveforms and discontinuity points are identified as a normal or abnormal electrophysiological signal of the ECG waveform based on the comparison using the processor.

In step 3860, the ECG waveform for the at least one heartbeat of the beating heart is displayed, one or more markers at a location of the at least one subwaveform or one or more discontinuity points is displayed on the ECG waveform, and the one or more markers are identified as a normal or abnormal cardiac electrophysiological signal using a display device.

I-Point and J-Point Detection and Measurement

As described above, ECG waveforms are prone to certain issues such as deformation, instability, standard point loss, and so on. Consequently, conventional ECG instruments are unable to accurately measure ECG parameters, such as the P-R interval, Q-T interval, ST segment, QRS complex, P-J interval, J-T interval, and VAT. Furthermore, as for the data measured manually, a very small variation can result in a difference of tens of milliseconds. Clinically, only simple standards can be used at present.

As described above, the ECG systems of the '204 Patent and the '930 Patent have addressed the technical problem of accurately measuring the different frequency domain signals from different parts of the heart muscle. Additional methods, however, are needed to employ the ECG systems of the '204 Patent and the '930 Patent to accurately measure ECG parameters such as the P-R interval, Q-T interval, ST segment, QRS complex, P-J interval, J-T interval, and VAT so that these standards can be used in clinical practice.

In various embodiments, systems and methods are provided to accurately detect the I-point, which is the point in an ECG waveform that demarks the location of the electrical connection between atrium and ventricle. These systems and methods are also able to accurately detect the J-point, which is the starting point for repolarization of the ventricle. From accurate I-point and the J-point measurements, other ECG parameters such as the P-R interval, Q-T interval, ST segment, QRS complex, P-J interval, J-T interval, and VAT are accurately measured. Also, new parameters are developed and measured.

Figure 50:
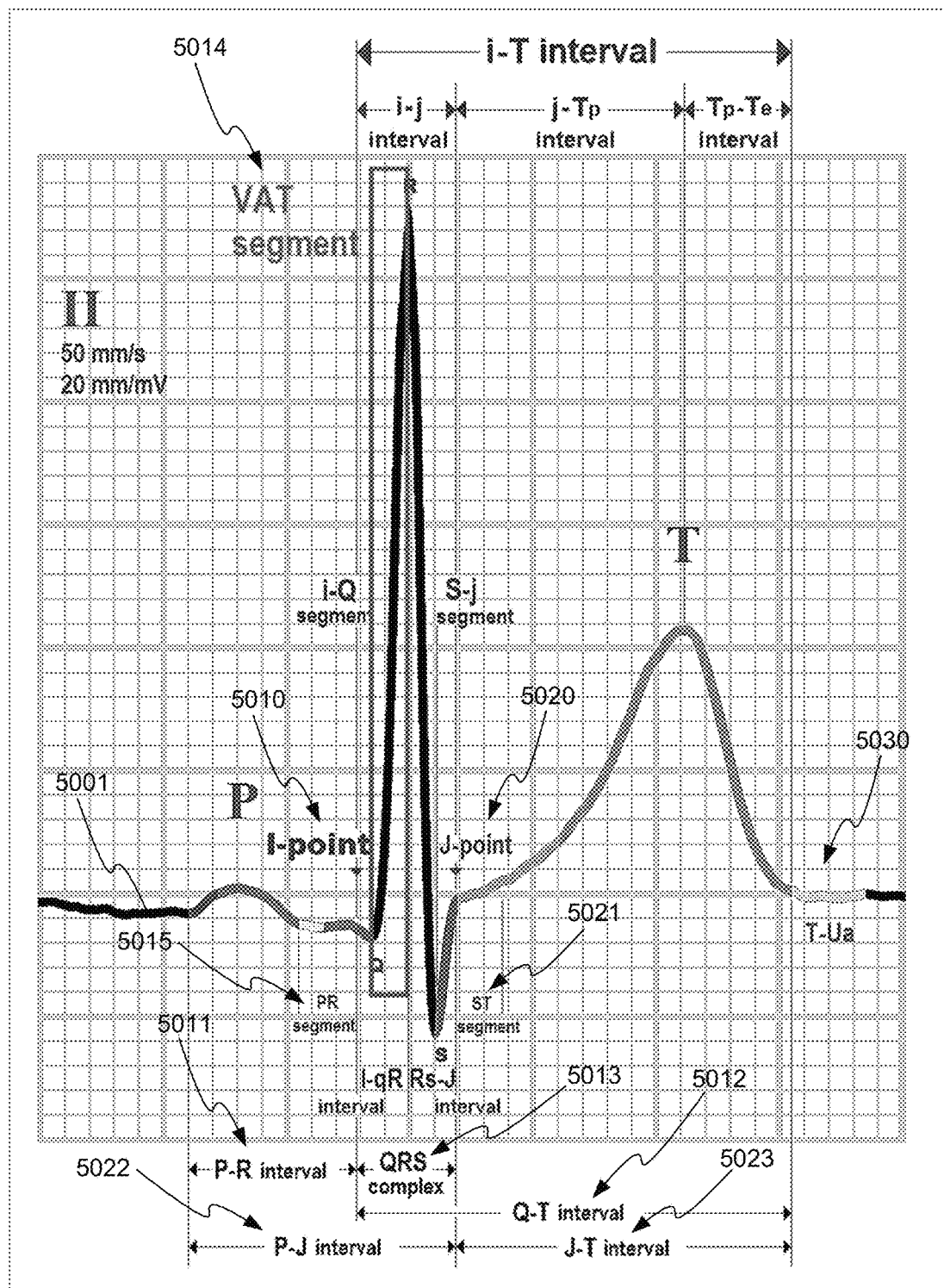
FIG. 50 is an exemplary plot of an ECG waveform showing the accurate detection and measurement of the I-point and J-point, in accordance with various embodiments.

FIG. 50 is an exemplary plot 5000 of an ECG waveform showing the accurate detection and measurement of the I-point and J-point, in accordance with various embodiments. In ECG waveform 5001, I-point 5010 and J-point 5020 are accurately detected and measured. From accurate I-point 5010 and the J-point 5020 measurements, other ECG parameters such as P-R interval 5011, Q-T interval 5012, ST segment 5021, QRS complex 5013, P-J interval 5022, J-T interval 5023, and ventricular activation (VAT) segment 5014 are accurately measured. I-point 5010 measurement is important to the following parameters: Q-T interval 5012, QRS complex 5013, VAT segment 5014, P-R interval 5011, and PR segment 5015. J-point 5020 measurement is important to the following parameters: ST segment 5021, P-J interval 5022, J-T interval 5023, and QRS complex 5013.

It is noted that the detection of the J-point and the I-point in most of the waveforms of traditional ECG are in an arc shape, from which it is hard to identify an accurate measurement point. As a result, even if a measurement itself is accurate, the result still cannot be utilized in clinical practice.

Figure 51:
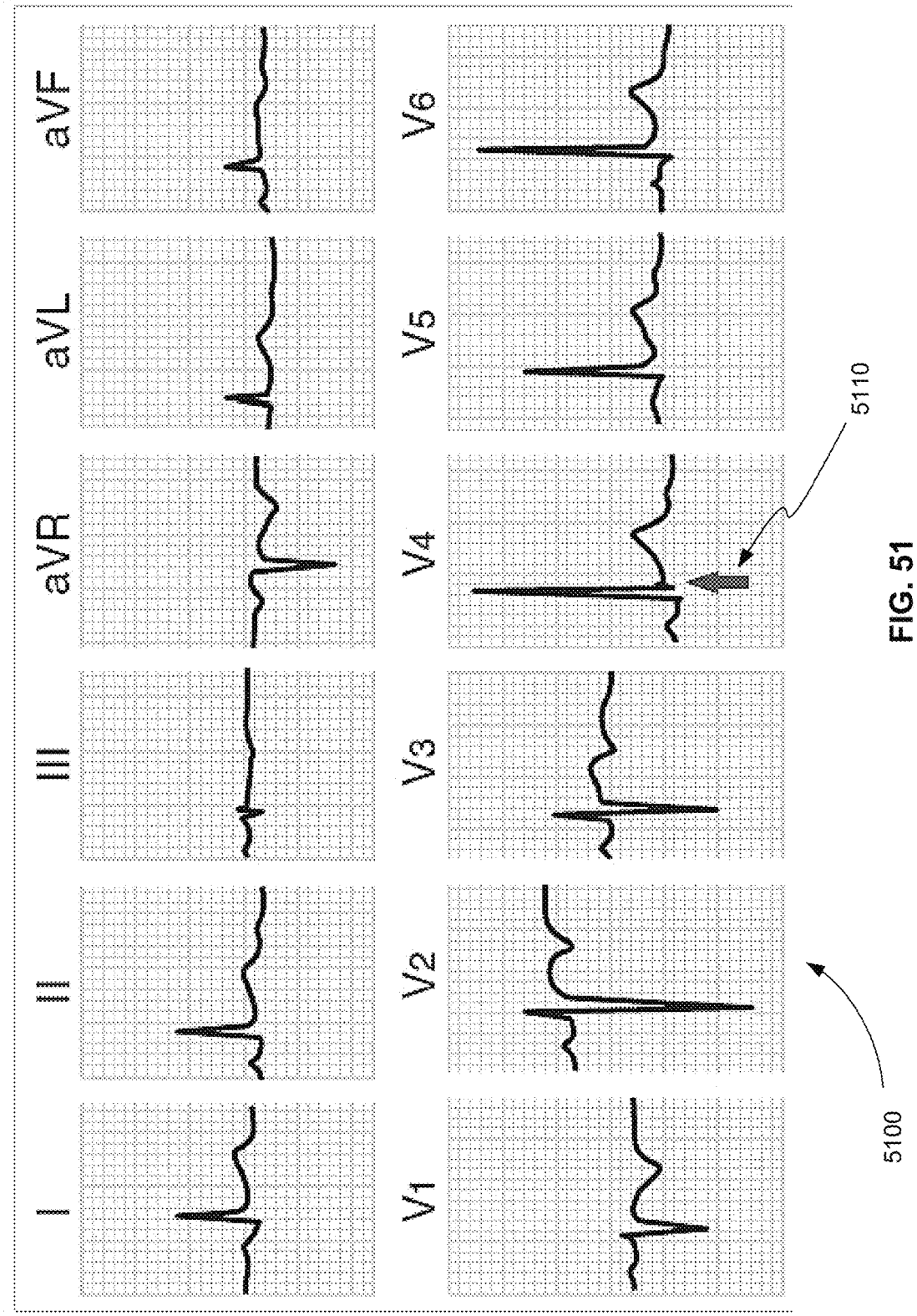
FIG. 51 is a series of plots of conventional ECG waveforms from different ECG leads showing that the J-point can only be detected from one lead, in accordance with various embodiments.

FIG. 51 is a series of plots 5100 of conventional ECG waveforms from different ECG leads showing that the J-point can only be detected from one lead, in accordance with various embodiments. For example, J-point 5110 is detected from lead $V_4$. However, as shown in FIG. 51, although J-point 5110 can be detected, it is not possible to accurately measure it even in lead $V_4$.

Figure 52:
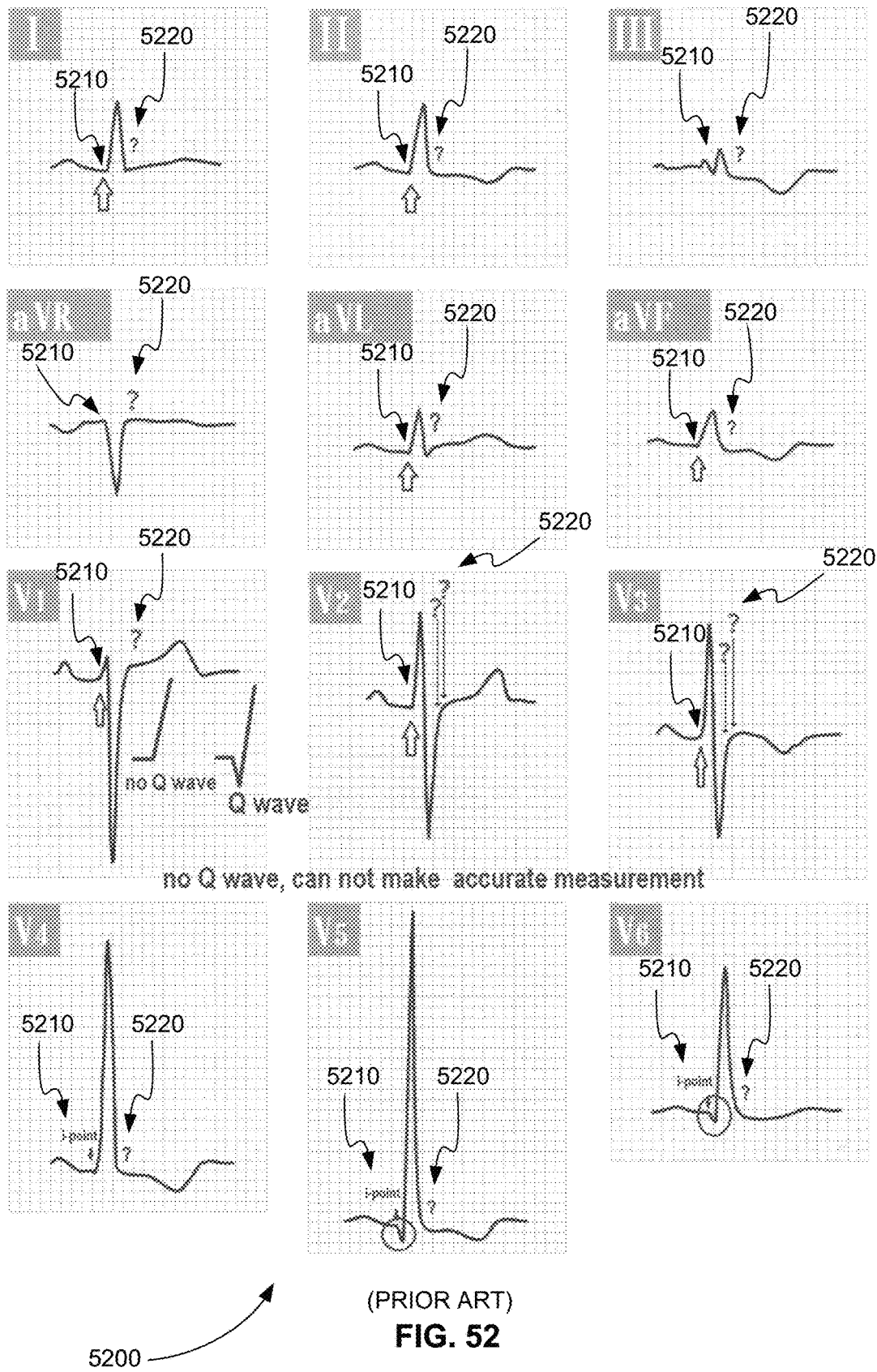
FIG. 52 is a series of plots of conventional ECG waveforms from different ECG leads showing that difficulty in measuring the I-point and the J-point, in accordance with various embodiments.

FIG. 52 is a series of plots 5200 of conventional ECG waveforms from different ECG leads showing that difficulty in measuring the I-point and the J-point, in accordance with various embodiments. For example, it is not possible to even detect I-point 5210 and J-point 5220 in leads I, II, III, aVR, aVL, aVF, $V_1$, $V_2$, and $V_3$. In leads $V_4$, $V_5$, and $V_6$, I-point 5210 can be detected but J-point 5220 cannot. Further, in these last three leads, although I-point 5210 can be detected, it is not possible to accurately measure it.

FIGS. 51 and 52 illustrate the biggest problem in the ECG field, namely inaccuracy. For example, the ST segment is still used in practice. It is a standard used for determining myocardial ischemia and myocardial infarction.

Figure 53:
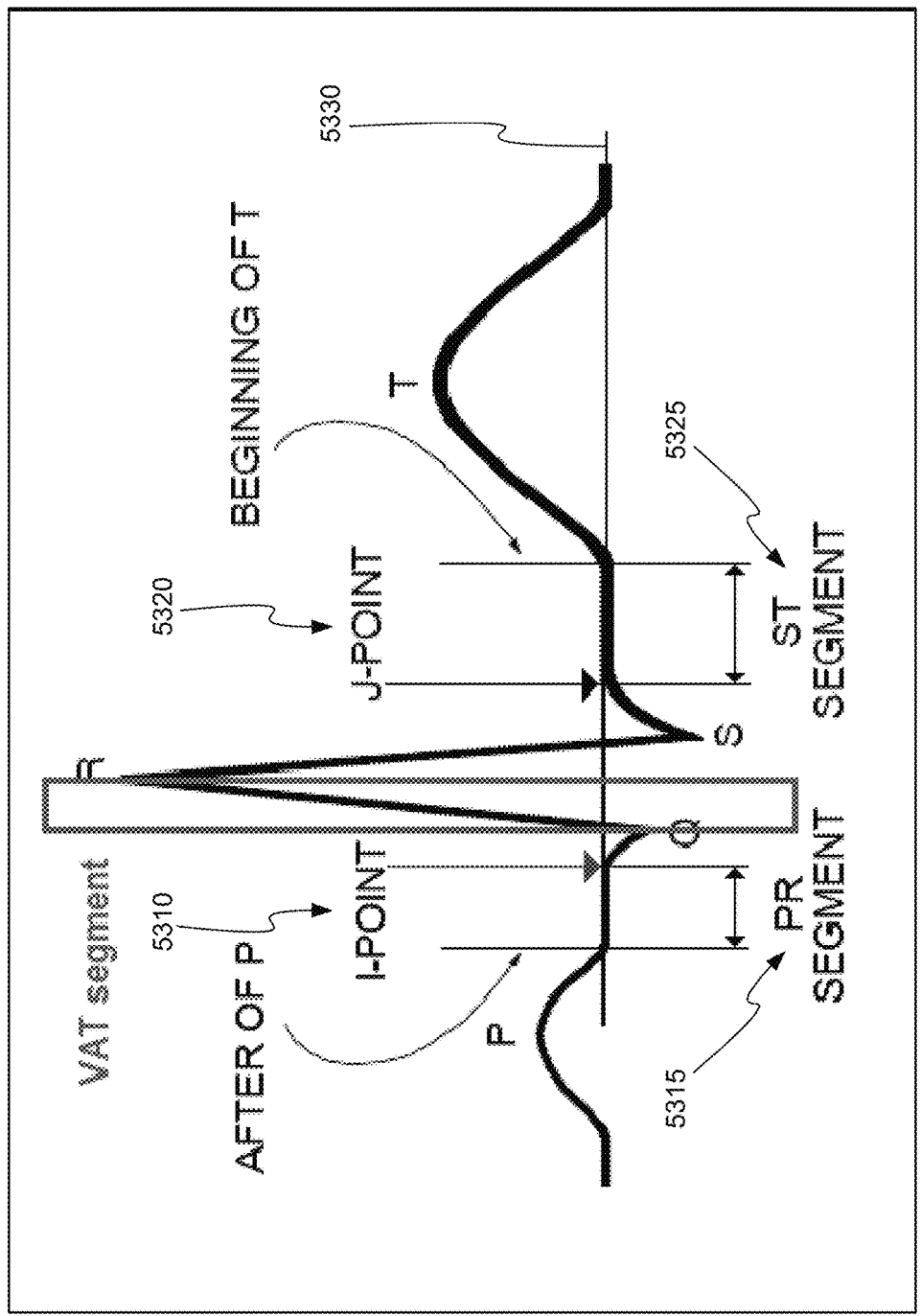
FIG. 53 is a plot of an ideal ECG waveform showing the importance of the I-point to the PR segment and the importance of the J-point to the ST segment, in accordance with various embodiments.

FIG. 53 is a plot 5300 of an ideal ECG waveform showing the importance of the I-point to the PR segment and the importance of the J-point to the ST segment, in accordance with various embodiments. For example, I-point 5310 is the ending point of PR segment 5315. Similarly, J-point 5320 is the starting point of ST segment 5325.

However, it is noted that in many patients, their ST segments do not show any elevation or depression, or show a slant line, or absence of the J point, and the like, which makes the ST segment unmeasurable.

Figure 54:
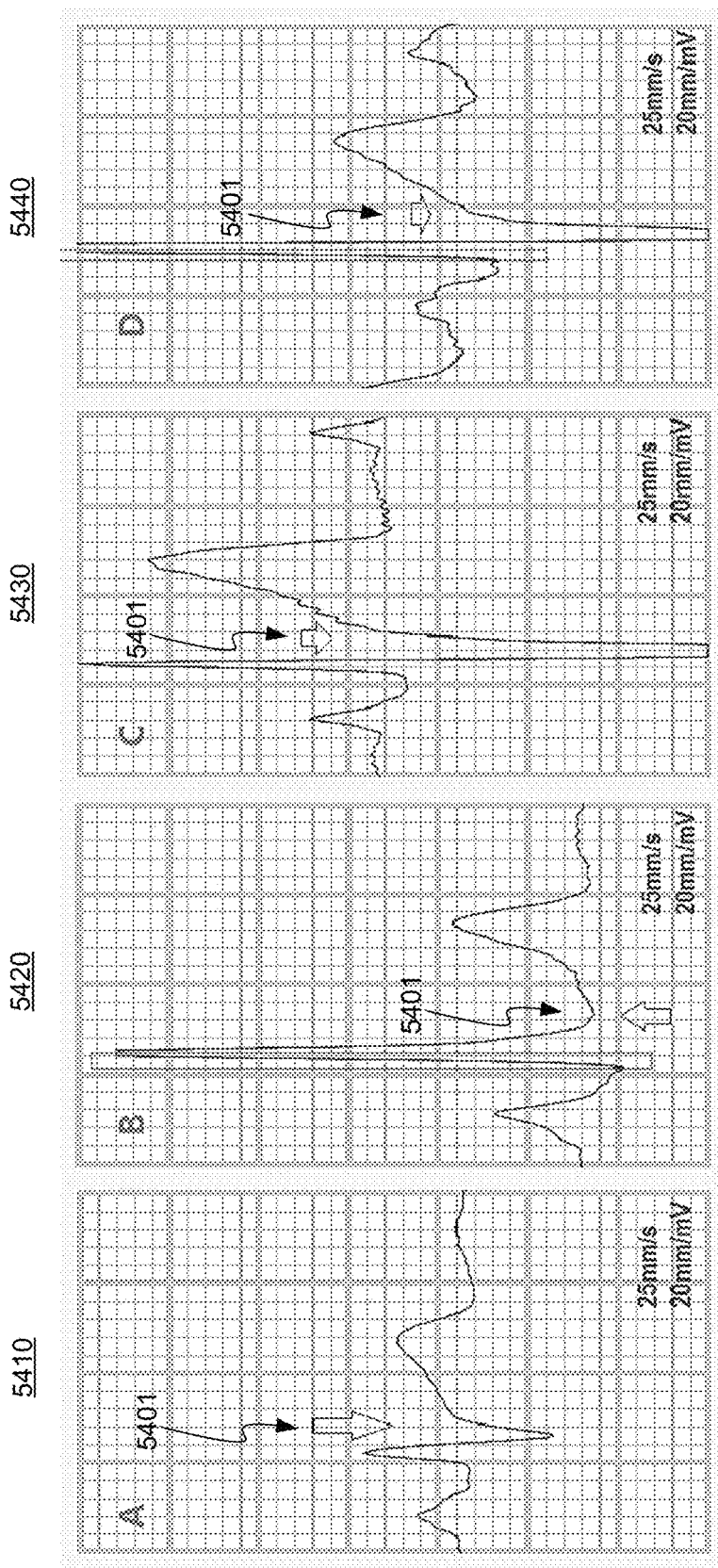
FIG. 54 is a series of plots of abnormal ECG waveforms showing the difficulty in determining the J-point and, therefore, the ST segment, in accordance with various embodiments.

FIG. 54 is a series of plots 5400 of abnormal ECG waveforms showing the difficulty in determining the J-point and, therefore, the ST segment, in accordance with various embodiments. Plots 5410, 5420, 5430, and 5440 all exhibit abnormal heart conditions. J-point 5401 is difficult to determine, making the ST segment unmeasurable.

Also, in many normal people, there may also be an elevation in the ST segment. In other words, in traditional ECG, normal results can be very similar to an abnormal condition; while in some cases, the measurement results of people with the condition are so close to that of a normal person; or sometimes, the ST segment cannot be measured, or the obtained measurement result is useless in a determination.

Figure 55:
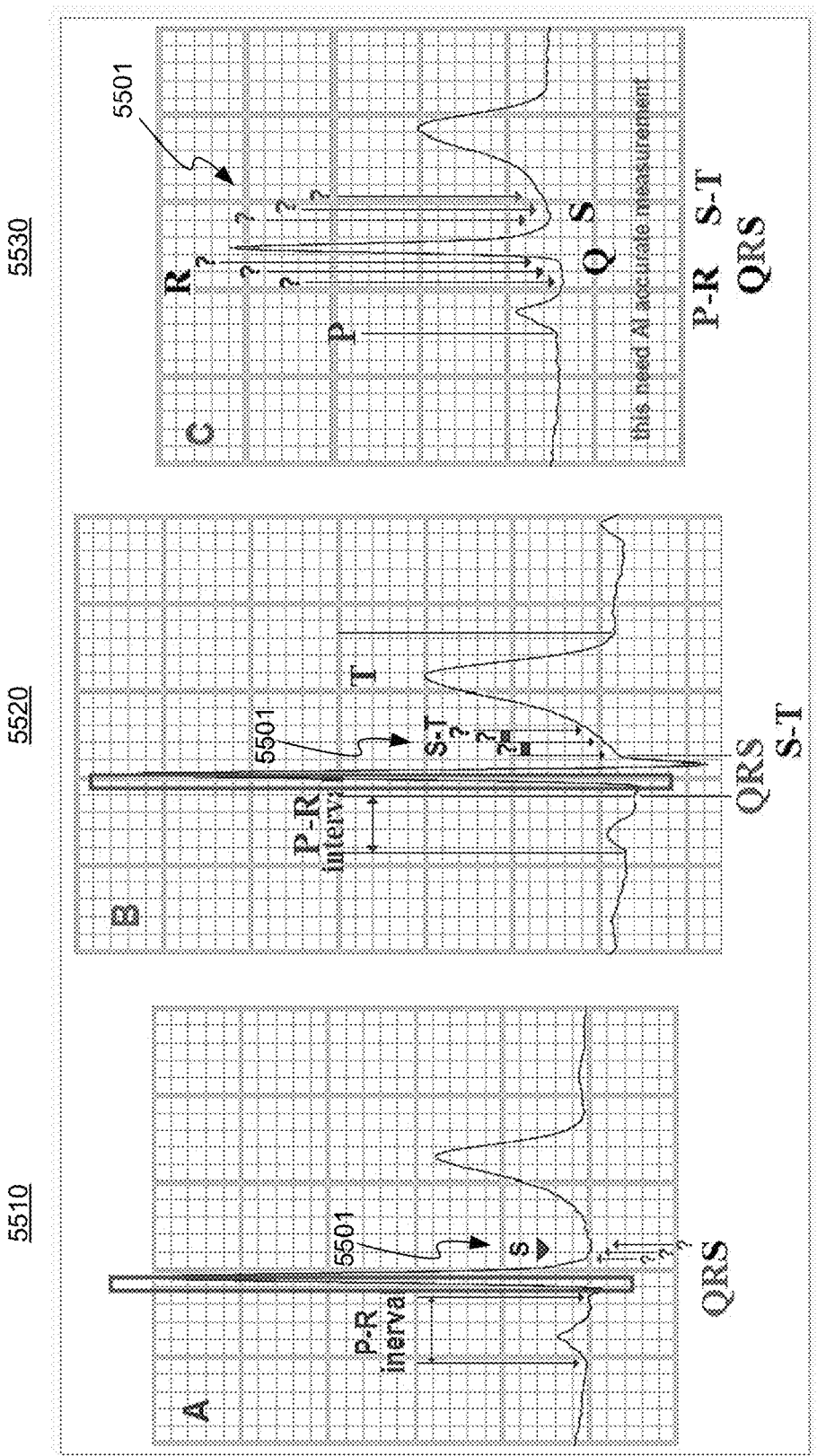
FIG. 55 is a series of plots of normal ECG waveforms showing the difficulty in determining the J-point and, therefore, the ST segment, in accordance with various embodiments.

FIG. 55 is a series of plots 5500 of normal ECG waveforms showing the difficulty in determining the J-point and, therefore, the ST segment, in accordance with various embodiments. Plots 5510, 5520, and 5530 all exhibit normal heart conditions. J-point 5501, however, is still difficult to determine, making the ST segment unmeasurable.

As a result, the clinical practice has been confused by the correlation between the traditional ECG and disease and the validity of a determination based thereon. There are some digitalized standards, but they either cannot be measured, or the measurement cannot be applied in clinical practice, and it becomes even more complex when the image is deformed. For example, there are ST segment elevations in both abnormal patients and normal people. In various embodiments, by way of I-point extension, even if the J-point is lost, it is possible the J-point position can still be determined. As a result, even in the case in which the J-point is lost, certain detection points for determination and analysis can still be acquired.

Since the invention of traditional ECG in 1903, on the left and right sides of the QRS there are always two semicircular sinusoidal waves, which are referred to as the P wave and T wave. There is a pulse wave, which is referred to as QRS wave group. Also, there is a half sinusoidal wave after the T wave, which is referred to as the U wave. It is noted that the foregoing waves are named in an alphabetic order based on the order of their appearances; for each heartbeat, the waves repeatedly appear in the following P→QRS→T→U.

As for J-point, it is the starting point of ST segment intersection from the ending point of ventricular depolarization to the starting point of ventricular repolarization. This intersection point is the beginning of ST segment, which is critical for determining the elevation or depression of the ST segment. In this regard, it is reasonable to first determine and establish the J-point. However, it is noted that the J point may be completely lost in many people with abnormal conditions, as shown in FIGS. 51 and 54. On the other hand, it is also lost in many normal people, as shown in FIG. 55. Accordingly, it is the weakest part in the traditional ECG.

The cardiac conduction system is the control center for cardiac electrical activity and an important portion for impulse conduction. Its special tissue structure and cell type determine that its cardiac electrical pacing and conduction functions are different from normal myocardia. In addition, it is closely related to the initiation and development of a variety types of arrhythmia. In this regard, it is important and necessary to study the cardiac conduction system.

It is noted that the traditional ECG signal acquisition range is from 0 to 150 Hz; and about 95% of the image signal convolution is actually ordinary atrial and ventricular myoelectric signals. Accordingly, many delicate electrical signals have been buried under those high frequency and ultra-high frequency signals. As a result, the I-point and J-point in most traditional ECG are not clearly shown, which causes the problem that certain standard digital parameters cannot be applied clinically.

Therefore, currently, the field lacks a digitalized uniform standard to verify whether a determination based on morphological waveforms is correct. It frequently occurs that for the same ECG image, different people can get different determination results, or a lot of different determinations can be derived therefrom.

Concerning the relationship between the positions of I-point and J-point in each heartbeat, it is noted that these two detection points are the most important determination points for QRS complex. The points Q and S of QRS interval in an accurate image should show sharp angles. In addition, on each of the left and right sides of QS, there is a reverse line reaching a parallel axis of the X axis. And, after the end of P wave, there is an equipotential line parallel to the X axis. The intersection of the distance between the ending point of the equipotential line and the q' point is the I-point. It has the following features: the line between the I-point and point q' is in a direction downward from the X axis. Moreover, there is another equipotential line parallel to the X axis before the starting point of the T wave, the intersection of the distance between the starting point of the equipotential line and the point s' is the J-point. It has the following features: the line between point s' and J-point is in a direction upward towards the X axis. The relationship between the positions of I-point and J-point in each heartbeat is illustrated in FIG. 53, for example.

Referring to FIG. 53, I-point 5310 is the starting point of the QRS complex, and at the same time, I-point 5310 is also the ending point of PR segment 5315 and P-R interval, that is to say, the starting point of the Q-T interval and the VAT segment. J-point 5320 is located at the intersection of equipotential line 5330 after the QRS interval and the starting point of ST segment 5325.

J-point 5320 is also the starting point of ST segment 5325 and the ending point of the QRS complex. It is the same in both the atrium and ventricle that the starting point P wave is the starting point of each heartbeat, and after P wave there is an equipotential line 5330. The portion from the ending point of P wave to I-point 5310 is referred to as PR segment 5315. The portion from the starting point of P wave to the ending point of PR segment 5315 (I-point 5310) is referred to as the PR interval. They have extraordinary significance in cardiac physiology and pathology.

In most of the traditional ECGs, a signal loss causes an arc-shaped portion. In a traditional ECG, the clear position of the I-point and J-point are rarely determined, as shown in FIGS. 51, 52, 54, and 55. The accuracy of most of the traditional ECGs is not high enough and cannot be measured. However, to provide a gold standard for ECG, these points cannot be ignored. In particular, because the I-point is the entrance of the connection between the atrium and the ventricle, it is critically important.

In various embodiments, the I-point is considered in the atrium, while the J-point is in the ventricle. It is noted that the process of a heartbeat is in the order from the atrium to the ventricle, and in the alphabetic order, the letter before J is I. Accordingly, the atrium point is named as I-point. Also, most normal people have this point. In many people, especially with abnormal conditions, the J-point is not detectable.

In various embodiments, 50,000 normal subjects were selected in normal physical examinations, and ECG waveforms were found using the systems of the present application. 95% of the normal people were found to have an I-point, and 89% of the normal people were found to have a J-point.

Figure 56:
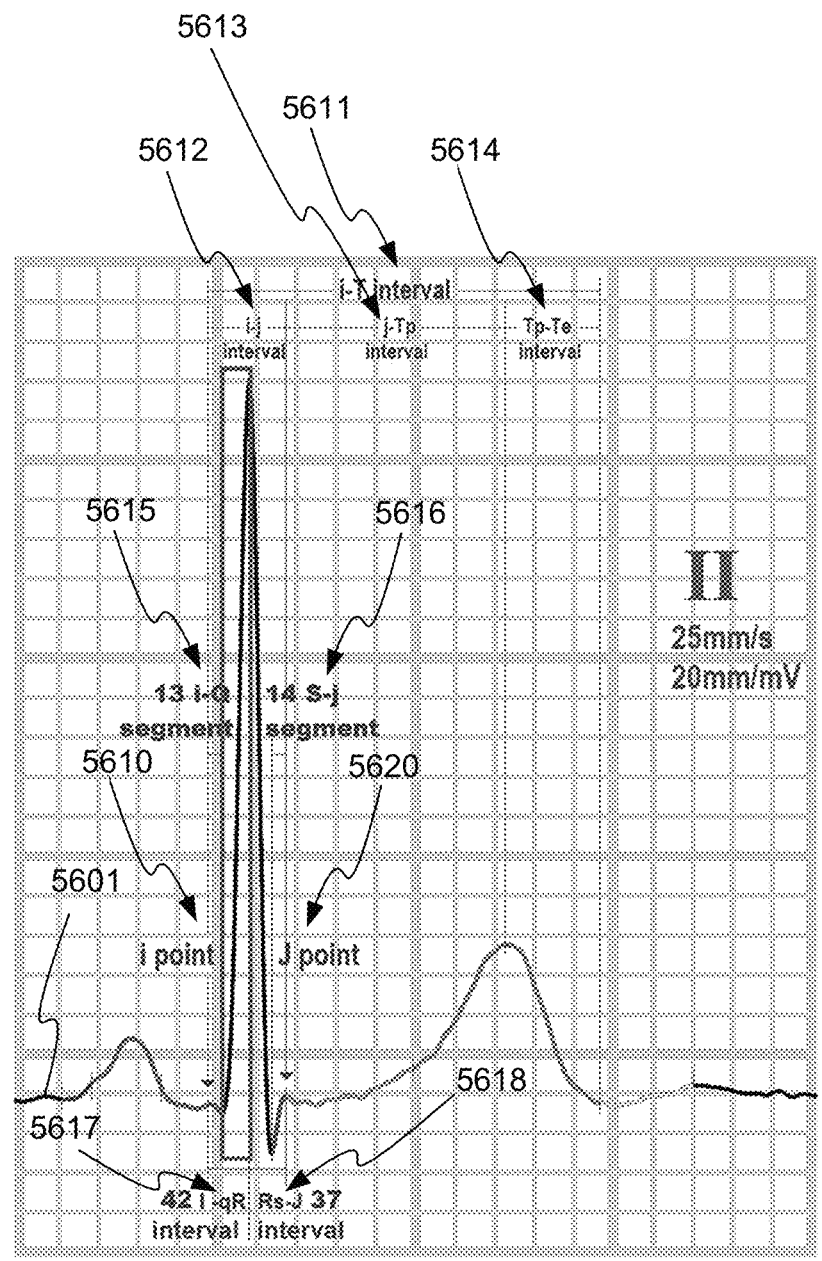
FIG. 56 is a plot showing an ECG waveform for a normal subject using the systems of the present application, in accordance with various embodiments.

FIG. 56 is a plot 5600 showing an ECG waveform for a normal subject using the systems of the present application, in accordance with various embodiments. In ECG waveform 5601 for the normal subject, an I-point 5610 and a J-point 5620 were detected and measured. Note that the high-precision ECG instrument of various embodiments has a sampling rate of 50,000/s.

The I-point has a very important physiological significance and clinical application value. From the point of view of anatomy, it is the connection portion between the ends of left and right bundles and the starting point of the Purkinje's fibrous network. After the I-point, there is the Purkinje's network, while before the J-point, it is the ending portion of the Purkinje's fibrous network. It is noted that the I-point and the J-point are a pair of key points that should be presented at the same time.

The I-point is the starting point of Purkinje's, and the starting point of an instantaneous vector. Hence, it is the only way from Purkinje's fibrous network 360° towards the entire endocardial wall of the heart. On the other hand, the J-point is located in the connection portion from the ending point of Purkinje's network to the starting point of ST segment. Hence, it is the only way from Purkinje's fibrous network towards the depth of endocardium.

In various embodiments, once the I-point is accurately positioned, new I-point related parameters are detected and measured. Referring to FIG. 56, these new parameters include I-T interval 5611, I-J interval 5612, J-Tp interval 5613, Tp-Te 5614, I-Q segment 5615, S-J segment 5616, I-qR interval 5617, and Rs-J interval 5618.

I-J interval 5612 extends from the starting point of the QRS wave group to J-point 5620, with 0-1 phase. Ventricular depolarization QR ascending branch reaches ventricular septal and apical parts, while the RS descending branch reaches the front part of the ventricular wall.

Figure 57:
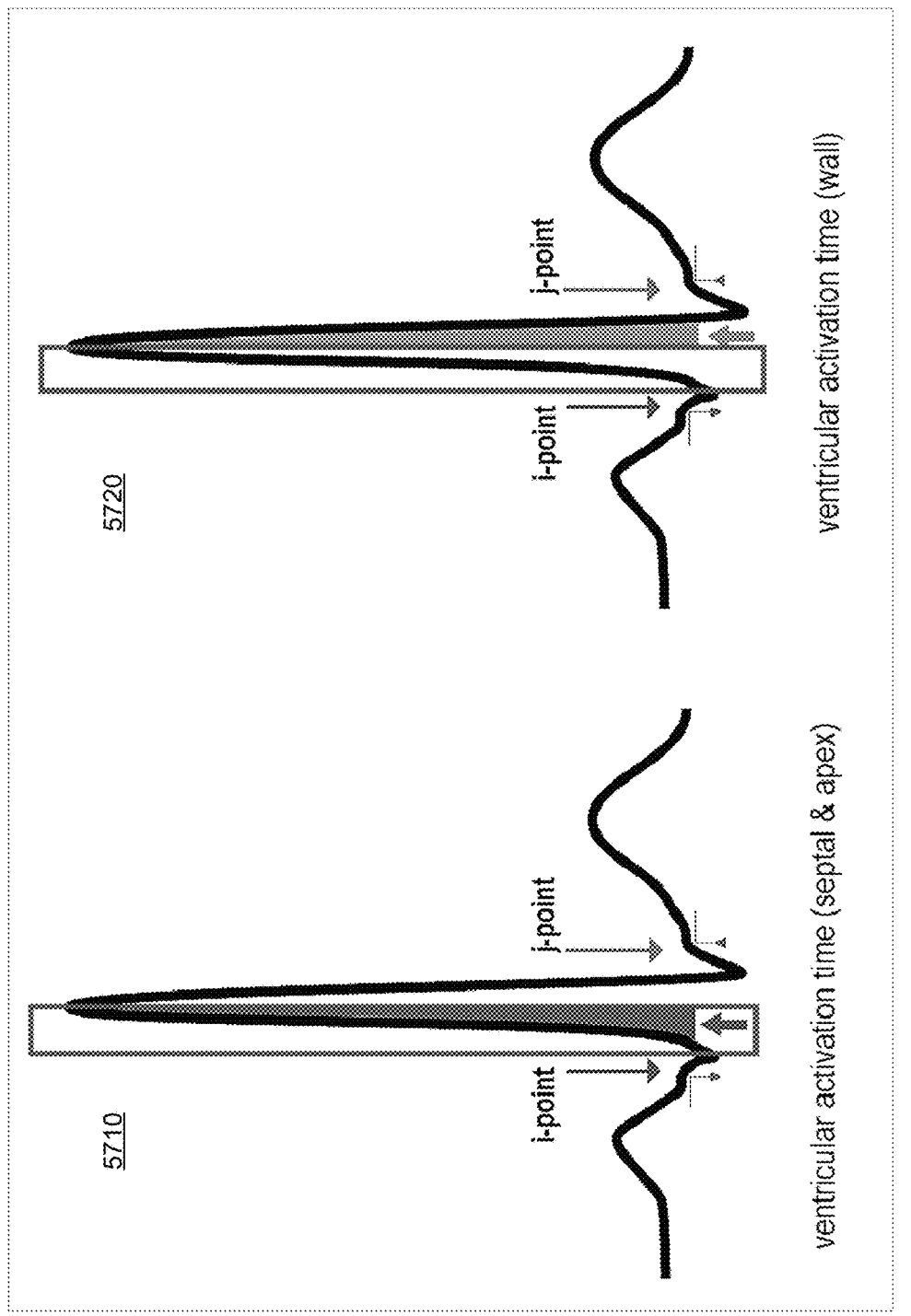
FIG. 57 is a series of plots of an ECG waveform showing depolarization of the ventricular septal and apical parts and the ventricular wall, in accordance with various embodiments.

FIG. 57 is a series of plots 5700 of an ECG waveform showing depolarization of the ventricular septal and apical parts and the ventricular wall, in accordance with various embodiments. Plot 5710 depicts depolarization of the ventricular septal and apical parts. Plot 5720 depicts depolarization of the ventricular wall.

Returning to FIG. 56, J-Tp interval 5613 depicts repolarization of the ventricular. J-Tp interval 5613 extends from J-point 5620 to the highest peak of the T wave. It has 2 phases, from ventricular repolarization to the front and middle portions of the ventricular wall.

Tp-Te 5614 extends from the highest peak of T wave to the end of T wave. It has 3 phases, from ventricular repolarization to the posterior part of the ventricular wall.

The entire I-T interval 5611 is equal to that of Q-T interval. However, I-T interval 5611 is able to distinguish various stages of ventricular contraction. I-J interval 5612 is the early stage of ventricular contraction. J-Tp interval 5613 is the mid-stage of ventricular contraction. Tp-Te 5614 is the late stage of ventricular contraction. As a result, within the entire I-T interval 5611, data analysis is carried out; and according to the specific anatomical location, certain important analysis and determination on local cardiac information can be conducted, especially for the atrioventricular junctions.

Referring to FIG. 50, T-Ua interval 5030 represents ventricular myocyte M cell APD and partial Purkinje's cell repolarization.

Returning to FIG. 56, I-Q segment 5615 is at the junction of the left and right bundles and the starting point of the Purkinje's. S-J segment 5616 is at the junction of the Purkinje's end and the endocardium. Hence the foregoing two data are very important. Their locations are equivalent to the intersections of complex highways. It is noted that the traditional ECG cannot detect this pair of data, because the images of the I-point and J-point are unclear, and most of the waveforms are shown as arcs. As a result, this pair of data cannot be detected. Therefore, their measurement requires an ECG instrument with very, very high precision.

I-qR interval 5617 is equivalent to the I-Q segment plus the VAT segment, yet I-qR interval has a correction formula. It is able to distinguish between left and right ventricles, so different data can be obtained from left and right ventricles. The VAT segment extends from the peak of the Q wave to the peak of the R wave.

The data for Rs-J interval 5618 interval is very complex, and accordingly, its normal value needs to be further studied in the clinical.

These new parameters have critical functions in clinical applications. They are the parameters concerning the connection part between atrium and ventricle and specific locations in ventricle. They not only can detect the starting and ending parts of the Purkinje's, but also can identify and diagnose the cause of certain primary and secondary diseases, in other word, whether the disease is caused by a primary lesion in atrium or a primary lesion in ventricle. In particular, for many coronary artery disease (CAD), myocardial infarction (MI) or CAD/MI patients, their traditional ECG result show no change in ST-T, this technique can show abnormal changes in atrial parts.

It is even more important for patients with Non-ST-elevation myocardial infarction (NSTEMI), or patients with non-coronary artery stenosis diffusive small blood vessel obstruction ischemia, hypertrophic cardiomyopathy, and heart failure disease, etc. In the case when a traditional ECG detection image does not show any change, both the established standard parameters and the new parameters and new detection points disclosed in the present application can be detected, which will bring in novel, effective, and convenient applications to clinical practice.

Normal ventricular activation (VAT) is a complex process that is dependent on interactions between the physiology and anatomy of both the specialized ventricular conducting system and the ventricular myocardium.

VAT is the product of two temporally overlapping events—endocardial activation and transmural activation. Endocardial activation is guided by the anatomic distribution and physiology of the His-Purkinje system. The broadly dispersed ramifications of this treelike (fractal) system and the rapid conduction within it result in the near-simultaneous activation of multiple endocardial sites and the depolarization of most of the endocardial surfaces of both ventricles within several milliseconds. The sequence of ventricular endocardial activation is dependent upon the fanlike distribution of the left bundle branch system across the endocardium.

Earliest activity begins in three sites: (1) the anterior paraseptal wall of the left ventricle, (2) the posterior paraseptal wall of the left ventricle, and (3) the center of the left side of the septum. These loci correspond to the sites of insertion of the fascicles of the left bundle branch. Septal activation begins on the left side and spreads across the septum from left to right and from apex to base. Wave fronts sweep from these initial sites of activation in anterior and inferior and then superior directions to activate the anterior and lateral walls of the left ventricle. The posterobasal areas of the left ventricle are the last to be activated.

Excitation of the right ventricle begins near the insertion point of the right bundle branch near the base of the anterior papillary muscle and spreads to the free wall. The final areas to be activated are the pulmonary conus and the posterobasal areas. Thus, in both ventricles, the overall endocardial excitation pattern begins on septal surfaces and sweeps down toward the apex and then around the free walls to the posterior and basal regions in an apex-to-base direction. The activation fronts then move from endocardium to epicardium. Excitation of the endocardium begins at sites of Purkinje-ventricular muscle junctions and proceeds by muscle cell to muscle cell conduction in an oblique direction toward the epicardium.

Normal QRS Complex

The sequence of endocardial and transmural activation results in the characteristic waveforms of the QRS complex. QRS patterns are described by the sequence of waves constituting the complex. An initial negative deflection is called the Q wave, the first positive wave is the R wave, and the first negative wave after a positive wave is the S wave. A second upright wave following an S wave is an R' as in R' wave. Tall waves are denoted by uppercase letters and smaller ones by low-ercase letters. A monophasic negative complex is referred to as a QS complex. Thus, for example, the overall QRS complex may be described as qRS if it consists of an initial small negative wave (the q wave) followed by a tall upright one (the R wave) and a deep negative one (an S wave). In an RSr' complex, initial tall R and S waves are followed by a small positive wave (the r' wave). In each case, the deflection must cross the baseline to be designated a discrete wave; changes in waveform direction that do not cross the baseline result in notches. Early QRS Patterns.

The complex pattern of activation described earlier can be simplified into two vectors, the first representing septal activation and the second representing left ventricular free wall activation. Initial activation of the interventricular septum cor-responds to a vector oriented from left to right in the frontal plane and anteriorly in the horizontal plane, corresponding to the anatomic position of the septum within the chest. This vector produces an initial positive wave in leads with axes directed to the right (lead aVR) or anteriorly (lead V1). Leads with axes directed to the left (leads I, aVL, V5, and V6) will register initial negative waves known as septal q waves. These initial forces are normally of low amplitude and are brief (less than 30 milliseconds in duration). The absence of these septal q waves, with QS complexes evident in the right precordial leads or seen as initial R waves in leads I, V5, and V6, typically is a normal variant and not associated with any cardiac disease.

Mid- and Late QRS Patterns

Subsequent parts of the QRS complex reflect activation of the free walls of the left and right ventricles. Because right ventricular muscle mass is considerably smaller than that of the left ventricle, it contributes little to normal QRS complexes. Thus the normal QRS can be considered to represent only septal and left ventricular activity, with little meaningful oversimplification. The complex interrelationships among cardiac position, conduction system function, and ventricular geometry result in a wide range of normal QRS patterns in the limb leads. The QRS pattern in leads II, III, and aVF may be predominantly upright with qR complexes, or these leads may show rS or RS patterns. Lead I may record an isoelectric RS pattern or a predominantly upright qR pattern.

The wide range of QRS patterns, especially in the inferior leads, can be interpreted by referring to the hexaxial reference system. The normal mean QRS axis in adults lies between −30 degrees and +90 degrees. If the mean axis is near 90 degrees, the QRS complex in leads II, III, and aVF will be predominantly upright, with qR complexes; lead I will record an isoelectric RS pattern because the heart vector lies perpendicular to the lead axis. If the mean axis is near 0 degrees, the patterns will be reversed; leads I and aVL will register predominantly upright qR pattern, and leads II, III, and aVF will show rS or RS patterns.

Mean QRS axes more positive than +90 degrees (usually with an rS pattern in lead I) represent right axis deviation. Axes between +90 and +120 degrees are referred to as moderate and those between +120 and +180 degrees are referred to as marked right axis deviation. Axes more negative than −30 degrees (with an rS pattern in lead II) represent left axis deviation, with axes between −30 and −45 degrees called moderate and those between −45 and −90 degrees called marked left axis deviation. Mean QRS axes of approximately −80 to −90 degrees are sometimes referred to as superior axis deviation and have been reported in cases of severe chronic obstructive lung disease.

Mean axes lying between −90 degrees and −180 degrees (or, equivalently, between +180 degrees and +270 degrees) are referred to as extreme axis deviations or, alternatively, as right superior axis deviations. The term indeterminate axis is applied when all six extremity leads show biphasic (QR or RS) patterns, indicating a mean axis that is perpendicular to the frontal plane. This finding can occur as a normal variant or may be seen in a variety of pathologic conditions. Normal QRS patterns in the precordial leads follow an orderly progression from right (V1) to left (V6).

In leads V1 and V2, leftward and posterior activation of the left ventricular free wall generates S waves following the initial r waves generated by septal activation (an rS pattern). These S waves are produced by the spread of activation in the free wall to the left and posteriorly, with generation of a heart vector directed away from the axes of these leads. Patterns in the midprecordial leads V3 and V4 reflect the activation front in the ventricular free wall. It first approaches the exploring electrode and then moves leftward and posteriorly to more remote regions of the left ventricle and away from the exploring electrode. In leads V3 and V4, this generates an R or r wave as it moves toward the electrode, followed by an S wave as it moves away from the electrode to produce rS or RS complexes.

As the exploring electrode moves laterally to the left, the R wave becomes more dominant and the S wave becomes smaller (or is totally lost) because of the longer time period during which the activation front moves toward the positive end of the electrode. In the leftmost leads (i.e., leads V5 and V6), the normal pattern also includes the septal q wave, to produce a qR or qRs pattern. Thus, in the precordial leads, the QRS complex usually is characterized by a consistent progression from an rS complex in the right precordial leads to an RS pattern in the midprecordial leads, and to a qR pattern in the left precordial leads. The site at which the pattern changes from an rS to an Rs configuration—the lead in which an isoelectric RS pattern is present—is known as the transition zone and normally occurs in lead V3 or V4. An altered location of the transition zone may occur for a variety of reasons; transition zones that are shifted to the right to lead V2 are early transitions, and those that are shifted leftward to V5 or V6 are delayed transitions.

Normal variability in QRS amplitudes, axes, and duration QRS are related to demographic and physiologic factors. QRS amplitudes are greater in men than in women, with higher amplitudes in African Americans than in those of other races. In addition, the location of the mitral papillary muscles in relation to the septum affects the duration and frontal plane axis, and left ventricular mass (within the normal range) affects both QRS amplitude and duration. Higher-than-normal amplitudes are characteristic of chamber hypertrophy and conduction defects, as discussed later on. Low-amplitude QRS complexes—that is, complexes with overall amplitudes of less than 0.5 mV in all frontal plane leads and less than 1.0 mV in the precordial leads—may occur as a normal variant or as a result of cardiac (e.g., multiple infarctions, infiltrative cardiomyopathies, myocarditis) or extracardiac (e.g., pericardial effusion, chronic obstructive pulmonary disease, pneumothorax) conditions.

QRS Duration

The upper normal value for QRS duration traditionally is set at less than 120 milliseconds (and often at less than 110 milliseconds), measured in the lead with the widest QRS complex. Women, on average, have somewhat shorter QRS durations than men (by approximately 5 to 8 milliseconds).

The Intrinsicoid Deflection.

An additional feature of the QRS complex is the intrinsicoid deflection. An electrode overlying the ventricular free wall will record a rising R wave as transmural activation proceeds toward it. Once the activation front reaches the epicardium, the full thickness of the wall under the electrode will be in an active state. At that moment, the electrode will register negative potentials as activation proceeds in remote cardiac areas. The sudden reversal of potential produces a sharp downslope—the intrinsicoid deflection—that approximates the timing of activation of the epicardium under the electrode. The term ventricular activation time (VAT) is sometimes used with reference to the surface ECG.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

I-Point Detection and Measurement System

The systems of the '204 Patent and the '930 Patent have used different signal processing methods to detect the harmonic signals and discontinuity points of a conventional ECG waveform. In various embodiments, artificial intelligence (AI) in conjunction with a database of normal and abnormal ECG data is used to measure and annotate the I-point of an ECG waveform during measurement of the ECG waveform.

Returning to FIG. 37, electrodes 3710 are attached to the skin of a patient in a noninvasive measurement, for example. In an alternative embodiment, electrodes 3710 are attached directly on the surface of a beating heart of a patient. Electrical signals produced by a beating heart are detected between pairs of electrodes 3710.

A voltage signal is detected between two electrodes 3710 by detector 3720. Detector 3720 also amplifies the voltage signal. Detector 3720 converts the electrical impulses to an ECG waveform for each heartbeat of the beating heart. Detector 3720 converts the voltage signal to a digital voltage signal using an analog to digital converter (A/D), for example. Detector 3720 provides the detected and amplified voltage signal from each pair of electrodes 3710 directly to display device 3740 to display the ECG waveform. The ECG waveform includes conventional P, Q, R, S, T, U, and J waveforms, for example. Detector 3720 also provides the detected and amplified voltage signal from each pair of electrodes 3710 directly to processor 3730.

Processor 3730 can be a separate electronic device that can include, but is not limited to, an application specific integrated circuit (ASIC), a field programmable gate array (FPGA), or a general-purpose processor or computer, such as the system of FIG. 1. Processor 3730 can be software implemented on another processor of the ECG device, such as a processor of display device 3740. Processor 3730 can also include a remote server computer.

Processor 3730 receives the ECG waveform for at least one heartbeat from detector 3720. Processor 3730 converts the ECG waveform to a frequency domain waveform. Processor 3730 separates the frequency domain waveform into two or more different frequency domain waveforms. Processor 3730 converts the two or more different frequency domain waveforms into a plurality of time domain cardiac electrophysiological subwaveforms and discontinuity points between these subwaveforms of the ECG waveform.

Processor 3730 compares the plurality of subwaveforms and discontinuity points to a database (not shown) of subwaveforms and discontinuity points for cardiac electrophysiological signals of ECG waveforms for a plurality of known and normal and abnormal patients. Processor 3730 identifies a discontinuity point of the plurality of subwaveforms and discontinuity points as an I-point of the ECG waveform based on the comparison.

Display device 3740 is an electronic display device, a printer, or any combination of the two. Display device 3740 displays the ECG waveform for the at least one heartbeat of the beating heart. Display device 3740 also displays a marker at a location of the discontinuity point on the ECG waveform and identifies the marker as the I-point.

In various embodiments, processor 3730 further identifies a second discontinuity point of the plurality of subwaveforms and discontinuity points as a J-point of the ECG waveform based on the comparison. Display device 3740 further displays a second marker at a location of the second discontinuity point on the ECG waveform and identifies the second marker as the J-point.

In various embodiments, display device 3740 further displays a marker between the first marker and the second marker on the ECG waveform and identifies the marker as the I-J interval.

In various embodiments, processor 3730 further identifies a third discontinuity point of the plurality of subwaveforms and discontinuity points as an endpoint of a T wave (Te) of the ECG waveform based on the comparison. Display device 3740 further displays a third marker at a location of the third discontinuity point on the ECG waveform and identifies the third marker as the endpoint of a T wave (Te).

In various embodiments, display device 3740 further displays a marker between the first marker and the third marker on the ECG waveform and identifies the marker as the I-T interval.

In various embodiments, processor 3730 further identifies a fourth discontinuity point of the plurality of subwaveforms and discontinuity points as a peak of a T wave (Tp) of the ECG waveform based on the comparison. Display device 3740 further displays a fourth marker at a location of the fourth discontinuity point on the ECG waveform and identifies the fourth marker as the peak of a T wave (Tp).

In various embodiments, display device 3740 further displays a marker between the second marker and the fourth marker on the ECG waveform and identifies the marker as the J-Tp interval.

In various embodiments, display device 3740 further displays a marker between the fourth marker and the third marker on the ECG waveform and identifies the marker as the Tp-Te interval.

In various embodiments, processor 3730 further identifies a fifth discontinuity point of the plurality of subwaveforms and discontinuity points as a start point of a T wave (Ts) of the ECG waveform based on the comparison. Display device 3740 further displays a fifth marker at a location of the fifth discontinuity point on the ECG waveform and identifies the fifth marker as the start point of a T wave (Ts).

In various embodiments, display device 3740 further displays a marker between the second marker and the fifth marker on the ECG waveform and identifies the marker as the S-T segment.

In various embodiments, display device 3740 further displays a marker between the second marker and the third marker on the ECG waveform and identifies the marker as the S-T interval.

In various embodiments, processor 3730 further identifies a third discontinuity point of the plurality of subwaveforms and discontinuity points as a peak of a Q wave (Q) of the ECG waveform based on the comparison. Display device 3740 further displays a third marker at a location of the third discontinuity point on the ECG waveform and identifies the third marker as the peak of a Q wave (Q).

In various embodiments, display device 3740 further displays a marker between the first marker and the third marker on the ECG waveform and identifies the marker as the I-Q segment.

In various embodiments, processor 3730 further identifies a fourth discontinuity point of the plurality of subwaveforms and discontinuity points as a peak of a R wave (R) of the ECG waveform based on the comparison. Display device 3740 further displays a fourth marker at a location of the fourth discontinuity point on the ECG waveform and identifies the fourth marker as the peak of a R wave (R).

In various embodiments, display device 3740 further displays a marker between the first marker and the fourth marker on the ECG waveform and identifies the marker as the I-qR interval.

In various embodiments, display device 3740 further displays a marker between the fourth marker and the second marker on the ECG waveform and identifies the marker as the Rs-J interval.

In various embodiments, processor 3730 further identifies a fifth discontinuity point of the plurality of subwaveforms and discontinuity points as a peak of an S wave (S) of the ECG waveform based on the comparison. Display device 3740 further displays a fifth marker at a location of the fifth discontinuity point on the ECG waveform and identifies the fifth marker as the peak of an S wave (S).

In various embodiments, display device 3740 further displays a marker between the fifth marker and the second marker on the ECG waveform and identifies the marker as the S-J segment.

Method for Measuring and Annotating the I-point

Figure 58:
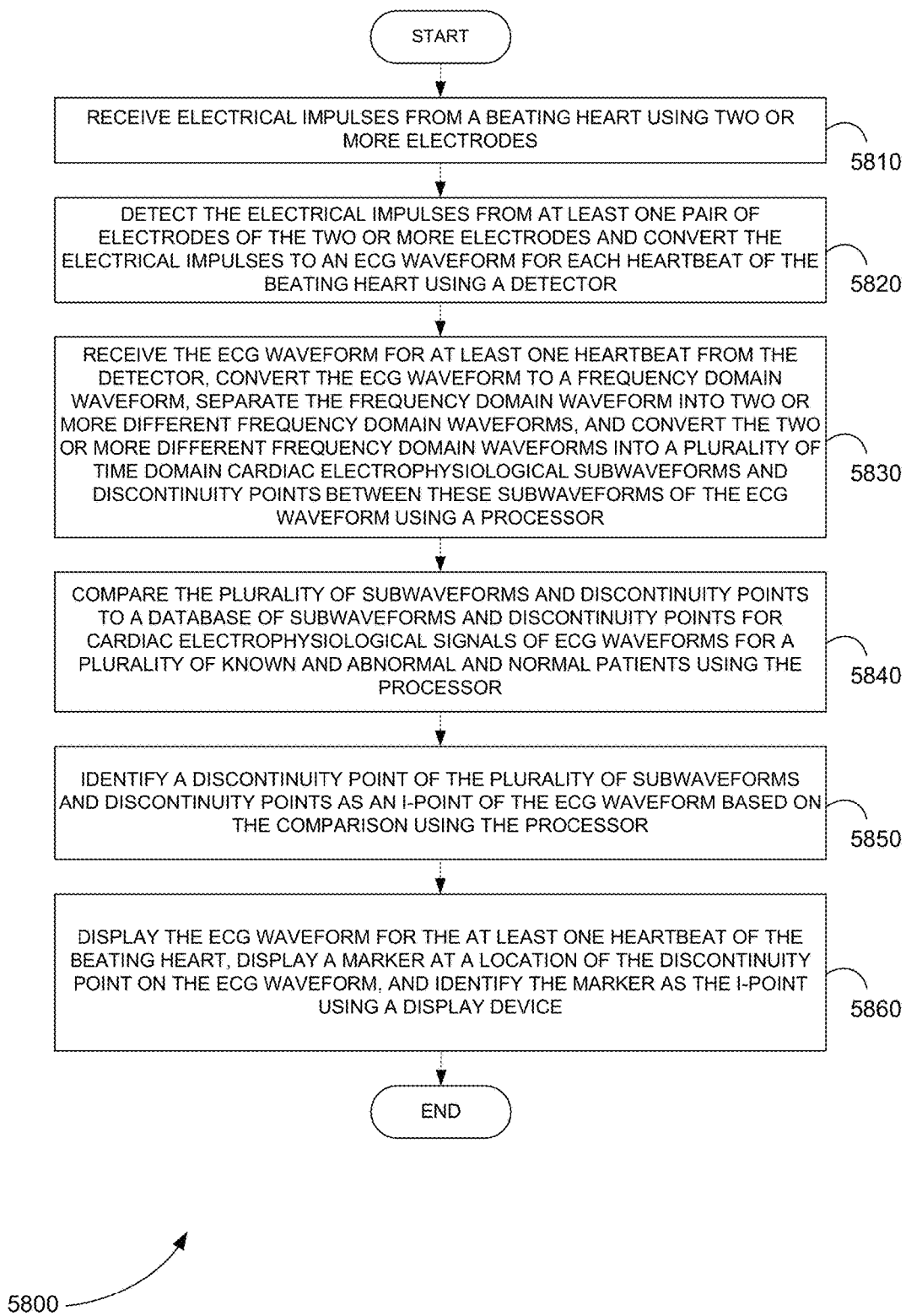
FIG. 58 is a flowchart showing a method for measuring and annotating the I-point of an ECG waveform during measurement of the ECG waveform, in accordance with various embodiments.

FIG. 58 is a flowchart showing a method 5800 for measuring and annotating the I-point of an ECG waveform during measurement of the ECG waveform, in accordance with various embodiments.

In step 5810 of method 5800, electrical impulses are received from a beating heart using two or more electrodes.

In step 5820, the electrical impulses are detected from at least one pair of electrodes of the two or more electrodes and converted to an ECG waveform for each heartbeat of the beating heart using a detector.

In step 5830, the ECG waveform for at least one heartbeat is received from the detector, the ECG waveform is converted to a frequency domain waveform, the frequency domain waveform is separated into two or more different frequency domain waveforms, and the two or more different frequency domain waveforms are converted into a plurality of time domain cardiac electrophysiological subwaveforms and discontinuity points between these subwaveforms of the ECG waveform using a processor.

In step 5840, the plurality of subwaveforms and discontinuity points are compared to a database of subwaveforms and discontinuity points for cardiac electrophysiological signals of ECG waveforms for a plurality of known and normal and abnormal patients using the processor.

In step 5850, a discontinuity point of the plurality of subwaveforms and discontinuity points is identified as an I-point of the ECG waveform based on the comparison using the processor.

In step 5860, the ECG waveform for the at least one heartbeat of the beating heart is displayed, a marker at a location of the discontinuity point is displayed on the ECG waveform, and the marker is identified as the I-point using a display device.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A noninvasive electrocardiography (ECG) system for measuring and annotating the I-point of an ECG waveform during measurement of the ECG waveform, comprising:
    two or more electrodes adapted to be located near a beating heart of a patient and attached to the skin of the patient that receive electrical impulses from the beating heart;
    a detector that detects the electrical impulses from at least one pair of electrodes of the two or more electrodes and converts the electrical impulses to an ECG waveform for each heartbeat of the beating heart;
    a processor that
        receives the ECG waveform for at least one heartbeat from the detector, converts the ECG waveform to a frequency domain waveform, separates the frequency domain waveform into two or more different frequency domain waveforms, and converts the two or more different frequency domain waveforms into a plurality of time domain cardiac electrophysiological subwaveforms and discontinuity points between these subwaveforms of the ECG waveform,
        compares the plurality of subwaveforms and discontinuity points to a database of subwaveforms and discontinuity points for cardiac electrophysiological signals of ECG waveforms for a plurality of known and normal and abnormal patients, and
        identifies a discontinuity point of the plurality of subwaveforms and discontinuity points as an I-point of the ECG waveform based on the comparison; and
    a display device that displays the ECG waveform for the at least one heartbeat of the beating heart, displays a first marker at a location of the discontinuity point on the ECG waveform, and identifies the first marker as the I-point.

2. The ECG system of claim 1, wherein the processor further identifies a second discontinuity point of the plurality of subwaveforms and discontinuity points as a J-point of the ECG waveform based on the comparison and the display device further displays a second marker at a location of the second discontinuity point on the ECG waveform and identifies the second marker as the J-point.

3. The ECG system of claim 2, wherein the display device further displays a marker between the first marker and the second marker on the ECG waveform and identifies the marker as the I-J interval.

4. The ECG system of claim 2, wherein the processor further identifies a third discontinuity point of the plurality of subwaveforms and discontinuity points as an endpoint of a T wave (Te) of the ECG waveform based on the comparison and the display device further displays a third marker at a location of the third discontinuity point on the ECG waveform and identifies the third marker as the endpoint of a T wave (Te).

5. The ECG system of claim 4, wherein the display device further displays a marker between the first marker and the third marker on the ECG waveform and identifies the marker as the I-T interval.

6. The ECG system of claim 4, wherein the processor further identifies a fourth discontinuity point of the plurality of subwaveforms and discontinuity points as a peak of a T wave (Tp) of the ECG waveform based on the comparison and the display device further displays a fourth marker at a location of the fourth discontinuity point on the ECG waveform and identifies the fourth marker as the peak of a T wave (Tp).

7. The ECG system of claim 6, wherein the display device further displays a marker between the second marker and the fourth marker on the ECG waveform and identifies the marker as the J-Tp interval.

8. The ECG system of claim 6, wherein the display device further displays a marker between the fourth marker and the third marker on the ECG waveform and identifies the marker as the Tp-Te interval.

9. The ECG system of claim 6, wherein the processor further identifies a fifth discontinuity point of the plurality of subwaveforms and discontinuity points as a start point of a T wave (Ts) of the ECG waveform based on the comparison and the display device further displays a fifth marker at a location of the fifth discontinuity point on the ECG waveform and identifies the fifth marker as the start point of a T wave (Ts).

10. The ECG system of claim 9, wherein the display device further displays a marker between the second marker and the fifth marker on the ECG waveform and identifies the marker as the S-T segment.

11. The ECG system of claim 9, wherein the display device further displays a marker between the second marker and the third marker on the ECG waveform and identifies the marker as the S-T interval.

12. The ECG system of claim 2, wherein the processor further identifies a third discontinuity point of the plurality of subwaveforms and discontinuity points as a peak of a Q wave (Q) of the ECG waveform based on the comparison and the display device further displays a third marker at a location of the third discontinuity point on the ECG waveform and identifies the third marker as the peak of a Q wave (Q).

13. The ECG system of claim 12, wherein the display device further displays a marker between the first marker and the third marker on the ECG waveform and identifies the marker as the I-Q segment.

14. The ECG system of claim 12, wherein the processor further identifies a fourth discontinuity point of the plurality of subwaveforms and discontinuity points as a peak of a R wave (R) of the ECG waveform based on the comparison and the display device further displays a fourth marker at a location of the fourth discontinuity point on the ECG waveform and identifies the fourth marker as the peak of a R wave (R).

15. The ECG system of claim 14, wherein the display device further displays a marker between the first marker and the fourth marker on the ECG waveform and identifies the marker as the I-qR interval.

16. The ECG system of claim 14, wherein the display device further displays a marker between the fourth marker and the second marker on the ECG waveform and identifies the marker as the Rs-J interval.

17. The ECG system of claim 14, wherein the processor further identifies a fifth discontinuity point of the plurality of subwaveforms and discontinuity points as a peak of an S wave (S) of the ECG waveform based on the comparison and the display device further displays a fifth marker at a location of the fifth discontinuity point on the ECG waveform and identifies the fifth marker as the peak of an S wave (S).

18. The ECG system of claim 17, wherein the display device further displays a marker between the fifth marker and the second marker on the ECG waveform and identifies the marker as the S-J segment.

19. A method for detecting and annotating the I-point of an electrocardiography (ECG) waveform during measurement of the ECG waveform, comprising:
receiving electrical impulses from a beating heart using two or more electrodes;
detecting the electrical impulses from at least one pair of electrodes of the two or more electrodes and converting the electrical impulses to an ECG waveform for each heartbeat of the beating heart using a detector;
receiving the ECG waveform for at least one heartbeat from the detector, converting the ECG waveform to a frequency domain waveform, separating the frequency domain waveform into two or more different frequency domain waveforms, and converting the two or more different frequency domain waveforms into a plurality of time domain cardiac electrophysiological subwaveforms and discontinuity points between these subwaveforms of the ECG waveform using a processor;
comparing the plurality of subwaveforms and discontinuity points to a database of subwaveforms and discontinuity points for cardiac electrophysiological signals of ECG waveforms for a plurality of known and normal and abnormal patients using the processor;
identifying a discontinuity point of the plurality of subwaveforms and discontinuity points as an I-point of the ECG waveform based on the comparison using the processor; and
displaying the ECG waveform for the at least one heartbeat of the beating heart, displaying a marker at a location of the discontinuity point on the ECG waveform, and identifying the markers as the I-point using a display device.

20. An invasive electrocardiography (ECG) system for measuring and annotating the I-point of an ECG waveform during measurement of the ECG waveform, comprising:
two or more electrodes placed directly on the surface of a beating heart of a patient that receive electrical impulses from the beating heart;
a detector that detects the electrical impulses from at least one pair of electrodes of the two or more electrodes and converts the electrical impulses to an ECG waveform for each heartbeat of the beating heart;
a processor that
receives the ECG waveform for at least one heartbeat from the detector, converts the ECG waveform to a frequency domain waveform, separates the frequency domain waveform into two or more different frequency domain waveforms, and converts the two or more different frequency domain waveforms into a plurality of time domain cardiac electrophysiological subwaveforms and discontinuity points between these subwaveforms of the ECG waveform,
compares the plurality of subwaveforms and discontinuity points to a database of subwaveforms and discontinuity points for cardiac electrophysiological signals of ECG waveforms for a plurality of known and normal and abnormal patients, and
identifies a discontinuity point of the plurality of subwaveforms and discontinuity points as an I-point of the ECG waveform based on the comparison; and a display device that displays the ECG waveform for the at least one heartbeat of the beating heart, displays a marker at a location of the discontinuity point on the ECG waveform, and identifies the marker as the I-point.

* * * * *